(12) United States Patent
Lingappa et al.

(10) Patent No.: US 7,638,269 B2
(45) Date of Patent: Dec. 29, 2009

(54) VIRAL CAPSID ASSEMBLY INTERMEDIATES AND METHODS OF PRODUCTION

(75) Inventors: Jaisri R. Lingappa, Seattle, WA (US); Kevin C. Klein, Seattle, WA (US); Vishwanath R. Lingappa, San Francisco, CA (US)

(73) Assignees: The Regents of the University of California CA (US); The University of Washington WA (US)

( * ) Notice: Subject to any disclaimer, the term of this patent is extended or adjusted under 35 U.S.C. 154(b) by 515 days.

(21) Appl. No.: 10/243,509

(22) Filed: Sep. 13, 2002

(65) Prior Publication Data

US 2003/0153066 A1 Aug. 14, 2003

Related U.S. Application Data

(63) Continuation-in-part of application No. 10/040,206, filed on Jan. 2, 2002, now abandoned, which is a continuation-in-part of application No. 09/020,144, filed on Feb. 6, 1998, now Pat. No. 6,593,103.

(60) Provisional application No. 60/039,309, filed on Feb. 7, 1997.

(51) Int. Cl.
*C12Q 1/00* (2006.01)
*C12Q 1/68* (2006.01)
*G01N 33/53* (2006.01)
*C12P 21/06* (2006.01)

(52) U.S. Cl. .................. 435/4; 435/6; 435/7.1; 435/69.1

(58) Field of Classification Search ............... 424/204.1, 424/207.1, 208.1; 435/5, 7.1, 69.1
See application file for complete search history.

(56) References Cited

U.S. PATENT DOCUMENTS 5,324,637 A 6/1994 Thompson et al.

OTHER PUBLICATIONS

Morikawa et al. Complete inhibition of human immunodeficiency virus Gag myristoylation is necessary for inhibition of particle budding. Journal of Biological Chemistry (Feb. 2, 1996) vol. 271, No. 5, pp. 2868-2873.*
Sakalian et al. Synthesis and assembly of retrovirus Gag precursors into immature capsids in vitro. Journal of Virology (Jun. 1996) vol. 70, No. 6, pp. 3706-3715.*
Lee et al. Inhibition of wild-type HIV-1 virus production by a matrix deficient Gag mutant. Virology (Apr. 1995) vol. 208, No. 2, pp. 808-811.*
Ou et al. Preferred translation of human hepatitis B virus polymerase from core protein- but not from precore protein-specific transcript. Journal of Virology (1990) vol. 64, No. 9, pp. 4578-4581.*
Santolini et al. Biosynthesis and biochemical properties of the hepatitis C virus core protein. Journal of Virology (1994) vol. 68, No. 6, pp. 3631-3641.*
Plamenberg A.C In vitro synthesis and assembly of Picornaviral capsid intermediate structures. Journal of Virology (1982) vol. 44, pp. 900-906.*
Weinheimer et al. Autoproteolysis of Herpes Simplex virus type 1 protease release an active catalytic domain found in intermediate capsid particles. Journal of Virology (1993) vol. 67, pp. 5813-5822.*
Cao et al. Protein conformer selection by ligand binding observed with crystallography, Protein Science, 1998, vol. 7, pp. 72-78.*
Bisbal et al., *J. Biol. Chem*. 270 (22): 13308-133 17 (1995).
Carmichael, *Nature* 418:379-380 (2002).
Erickson and Blobel, *Methods Enzymol* 96:38-50 (1983).
Goncavales et al., *J. Biol. Chem*. 277: 3206-3205 (2002).
Hegde et al. *Molecular Cell* 2:85-89 (1998).
Merrick, W.C., *Methods Enzymol*. 101:606-615 (1983).
Morris et al., *Nature Biotechnology* 19:1173-1176 (2001).
Novina et al., *Nature Medicine* 8:681-686 (2002).
Platt et al. *PNAS* 91:4594-4598 (1994).
Rose et al., *Nucleic Acids Research* 26:1628-1635 (1998).
Royer, M., et al., *Virology* 184:417-422 (1991).
Rutkowski et al. *PNAS* 98:7823-7828 (2001).
Spearman et. al., *J. Virology* 70 (11): 8187-8194 (1996).
Spearman, P. et al., *J. Virol*. 68:3232-3242 (1994).
Weldon, Jr., et al., *J Virol* 72: 3098-106 (1998).
Willison et al., *Cell* 57:621-632 (1989).
Wills et al., *J. Virol* 65:3804-3812 (1991).
Degar et al. "Inactivation of the Human Immunodeficiency Virus by Hypericin: Evidence for Photochemical Alterations of p24 and a Block in Uncoating" *AIDS Research & Human Retroviruses* 8(11):1929-1936 (1992).
Fäcke et al. "A Large Deletion in the Matrix Domain of the Human Immunodeficiency Virus gag Gene Redirects Virus Particle Assembly from the Plasma Membrane to the Endoplasmic Reticulum" *J of Virology* 67(8):4972-4980 (1993).
Flores et al. "Akt-Mediated Survival of Oligodendrocytes Induced by Neuregulins" *J of Neuroscience* 20(20):7622-7630 (2000).
Geballe et al. "Variable inhibition of cell-free translation by HIV-1 transcript leader sequences" *Nucleic Acids Research* 20(16):4291-4297 (1992).
Gelderblom et al. "Assembly and morphology of HIV: potential effect of structure on viral function" *AIDS* 5:617-638 (1991).
Gheysen et al. "Assembly and Release of HIV-1 Precursor PR55$^{gag}$ Virus-like Particles from Recombinant Baculovirus-Infected Insect Cells" *Cell* 59:103-112 (1989).
Glass et al. "A Sequence Related to the Human Gonadoliberin Precursor Near the N-termini of HIV and SIV gag Polyproteins" *J. Theor. Biol*. 150:489-496 (1991).

(Continued)

Primary Examiner—J S Parkin
Assistant Examiner—Louise Humphrey
(74) Attorney, Agent, or Firm—Stacy Landry; Quine Intellectual Property Law Group

(57) ABSTRACT

A cell-free method for translation and assembly of viral capsid and capsid intermediates is disclosed. Also disclosed are novel capsid assembly intermediates and novel host proteins which bind to such assembly intermediates. The invention also includes a screening method for compounds that alter viral capsid assembly, and a method of treating viral infection using compounds which inhibit the capsid assembly pathway.

8 Claims, 28 Drawing Sheets

OTHER PUBLICATIONS

Görlich et al. "A protein of the endoplasmic reticulum involved early in polypeptide translocation" *Nature* 357:47-52 (1992).

Göttlinger et al. "Role of capsid precursor processing and myristoylation in morphogenesis and infectivity of human immunodeficiency virus type 1" *Proc. Natl. Acad. Sci. USA* 86:5781-5785 (1989).

Hockley et al. "comparative morphology of Gag protein structures produced by mutants of the *gag* gene of human immunodeficiency virus type 1" *J. of General Virology* 75:2985-2997 (1994).

Isada, Carlos M. "New developments in long-term treatment of HIV: The honeymoon is over" *Cleve. Clin. J. Med* 68:804-807 (2001).

Jain et al. "Metabolic complications associated with antiretroviral therapy" *Antiviral Research* 51:151-177 (2001).

Jowett et al. "Distinct signals in human immunodeficiency virus type 1Pr55 necessary for RNA binding and particle formation" *J. of General Virology* 73:3079-3086 (1992).

Kaushik et al. "Role of Glutamine-151 of Human Immunodeficiency Virus Type-1 Reverse Transcriptase in RNA-Directed DNA Synthesis" *Biochemistry* 36:14430-14438 (1997).

Laughrea et al. "Mutations in the Kissing-Loop Hairpin of Human Immunodeficiency Virus Type 1 Reduce Viral Infectivity as well as Genomic RNA Packaging and Dimerization" *J. of Virology* 71(5):3397-3406 (1997).

Li et al. "Multiple Forms of tRNA$^{Lys3}$ in HIV-1" *Biochem & Biophysical Res. Comm.* 227:530-540 (1996).

Lin et al. "Current Treatment Strategies for Chronic Hepatitis B and C" *Annu. Rev. Med.* 52:29-49 (2001).

Lingappa et al. "A Eukaryotic Cytosolic Chaperonin Is Associated with a High Molecular Weight Intermediate in the Assembly of Hepatitis B Virus Capsid, a Multimeric Particle" *J. of Cell Biology* 125(1):99-111 (1994).

Lingappa et al. "A Multistep, ATP-dependent Pathway for Assembly of Human Immunodeficiency Virus Capsids in a Cell-free System" *J. Cell Biol.* 136:567-581 (1997).

Lo et al. "Interaction between Hepatitis C Virus Core Protein and E1 Envelope Protein" *J. of Virology* 70(8):5177-5182 (1996).

Ohlmann et al. An Internal Ribosome Entry Segment Promotes Translation of the Simian Immunodeficiency Virus Genomic RNA *J. of Bio. Chem* 276(16):11899-11906 (2000).

Page et al. "Construction and Use of a Human Immunodeficiency Virus Vector for Analysis of Virus Infectivity" *J. of Virology* 64(11):5270-5276 (1990).

Papadopulos-Eleopulos, et al. "A critical analysis of the pharmacology of AZXT and its use in AIDS" *Curr. Med. Res. Opin.* 15 Suppl. 1:S1-45 (1999) [Abstract Only].

Ren, et al. "Caco-2 cell permeability vs human gastro-intestinal absorption: QSPR analysis" *Prog. Drug. Res. Spec.* No. 1-34 (2001).

Richards et al. "Inhibition of the aspartic proteinase from HIV-2" *FEBS Lett.* 253:214-216 (1989).

Sakallan et al. "Synthesis and Assembly of Retrovirus Gag Precursors into Immature Capsids In Vitro" *J. of Virology* 70:3706-3715 (1996).

Santolini et al. "Biosynthesis and Biochemical Properties of the Hepatitis C Virus Core Protein" *J. of Virology* 68(6):3631-3641 (1994).

Sen et al. "The Interferon System—A Bird's Eye View of Its Biochemistry" *J. of Biological Chemistry* 267(8):5017-5020 (1992).

Shih et al. "Modulation of the *trans*-Suppression Activity of Hepatitis C Virus Core Protein by Phosphorylation" *J. of Virology* 69(2):1160-1171 (1995).

Smith, Kendall A. "To cure chronic HIV infection, a new therapeutic strategy is needed" Curr. Opin. Immunol. 13:614-624 (2001).

Spirin et al. "A Continuous Cell-Free Translation System Capable of Producing Polypeptides in High Yield" *Science* 242:1162-1164 (1988).

Tanchou et al. "Formation of Stable and Functional HIV-1 Nucleoprotein Complexes in Vitro" *J. Mol. Biol.* 252:563-571 (1995).

Towler et al. "The Biology and Enzymology of Eukaryotic Protein Acylation" *Ann. Rev. Biochem.* 57:69-99 (1988).

Trono et al. "HIV-1 Gag Mutants Can Dominantly Interfere with the Replication of the Wild-Type Virus" *Cell* 59:113-120 (1969).

VanLint, et al. "Transcription Factor Binding Sites Downstreatm of the Human Immunodeficiency Virus Type 1 Transcription Start Site Are Important for Virus Infectivity" *J. of Virology* 71(8):6113-6127 (1997).

Wang et al. "Assembly, Processing, and Infectivity of Human Immunodeficiency Virus Type 1 Gag Mutants" *J. of Virology* 67(7):4264-4273 (1993).

Wills et al. "Form, function, and use of retroviral gag proteins" *AIDS* 5:639-654 (1992).

Yasui et al. "The Native Form and Maturation Process of Hepatitis C Virus Core Protein" *J. of Virology* 72(7):6048-6055 (1998).

Yerly et al. "Quantitation of Human Immunodeficiency Virus Provirus and Circulating Virus: Relationship with Immunologic Parameters" *J. Infect. Dis.* 166(2):269-276 (1992).

Zhao et al. "Complementation of Human Immunodeficiency Virus (HIV-1) Gag Particle Formation" *Virology* 199:403-408 (1994).

Raju et al. "Mammalian myristoyl CoA:protein N-myristoyltransferase" *Mol. And Cellular Biochem.* 149/150:191-202 (1995).

\* cited by examiner

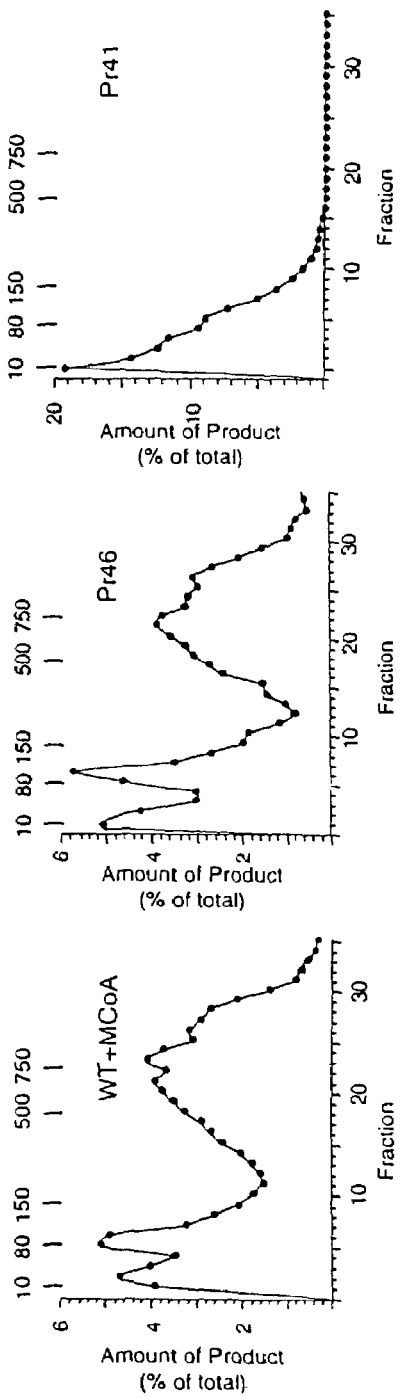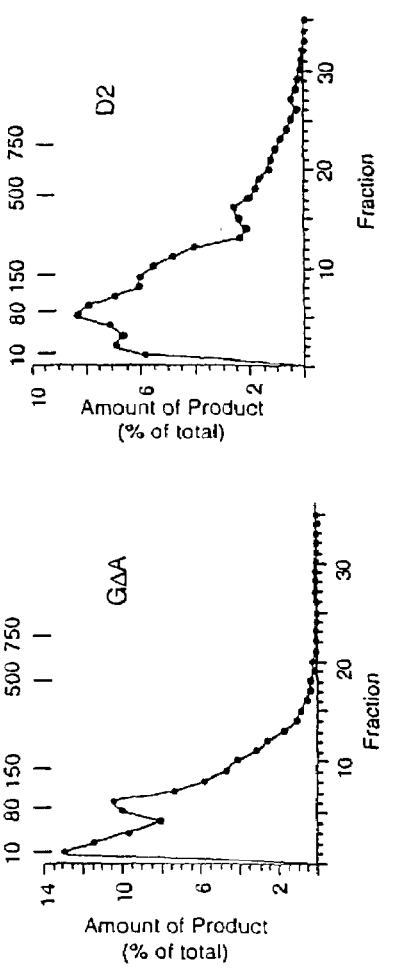

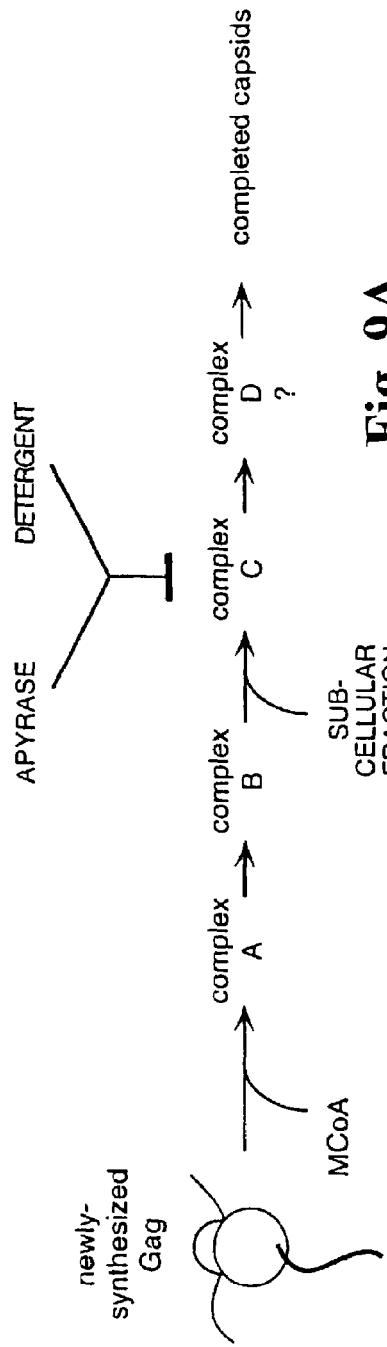

Figure 10

```
huhp68     1   MADKLTRIAIVNHDKCKPKKCRQECKKSCPVVRMGKLCIEVTPQSKIAWISETLCIGCGI
wghp68     1   MADRLTRIAIVSEDKCKPKKCRQECKKSCPVVKTGKLCIEVSPVAKLAPISEELCIGCGI
consensus  1   *.***  ****************.*****.*  *.*.* ***** huhp68     61  CIKKCPPGALSIVNLPSNLEKETTHRYCANAFKLHRLPIPRPGEVLGLVGTNGIGKSAAL
wghp68     61  CVKKCPFDAIEIINLPKDLEKDTTHRYGPNTFKLHRLPVPRPGQVLGLVGTNGIGKSTAL
consensus  61  *.***** *. *.*** ***.****  * *******.****.**************.**

huhp68     121 KILAGKQKPNLGKYDDPPDWQEILTYFRGSELQNYFTKILEDDLKAIIKPQYVARFLRLA
wghp68     121 KVLAGKLKPNLGRFKNPPDWQEILTYFRGSELQNYFTRILEDNLKAIIKPQYVDHIPKAV
consensus  121 *.**** *****..  .*******************.****.**********  .  .

huhp68     181 KGTVGSILDRKDETKTQAIVCQQLDLTHLKERNVEDLSGGELQRFACAVVCIQKADIPMF
wghp68     181 QGNVGQVLEQKDERDMKNELCVDLELNQVIDRNVGDLSGGELQRFAIAVVAVQSAEIYMF
consensus  181 * ** .*. ***     .* *.*  . ..*** ************ *** .*.*.*.**

huhp68     241 DEPSSYLDVKQRLKAAITIRSLINPDRYIIVVEHDLSVLDYLSDFICCLYGVPSAYGVVT
wghp68     241 DEPSSYLDVKQRLKAARVIRSLLRSNSYVIVVEHDLSVLDYLSDFICCLYGKPGAYGVVT
consensus  241 **************  ** .   *.******************* * * ***** huhp68     301 MPFSVREGINIFLDGYVPTENLRFRDASLVFKVAETAN-EEEVKKMCMYKYPGMKKKMGE
wghp68     301 LPFSVREGINIFLAGFVPTENLRFRDESLTFKIAETQESAEEVATYQRYKYPTMSKTQGN
consensus  301 .*********** *.*********  .  .     **** *  . * huhp68     360 FELAIVAGEFTDSEIMVMLGENGTGKTTFIRMLAGRLKPD--EG--GEVPVLNVSYKPQK
wghp68     361 FKLSVVEGEFTDSQIVVMLGENGTGKTTFIRMLAGLLKPDTMEGTEVEIPEFNVSYKPQK
consensus  361 * *.*.* ******.*.****************      .* * ******* huhp68     416 ISPKSTGSVRQLLHEKIRDAYTHPQFVTDVMKPLQIENIIDQEVQTLSGGELQRVRLRLC
wghp68     421 ISPKFQHPVRHLLHSKIRDSYTHPQFVSDVMKPLQIEQLMDQEVINLSGGELQRVALCLC
consensus  421 **    .* .**.*****  .  .***** huhp68     476 LGKPADVYLIDEPSAYLDSEQRLMAARVVKRFILHAKKTAFVVEHDFIMATYLADRVIVF
wghp68     481 LGKPADIYLIDEPSAYLDSEQRIVASKVIKRFILHAKKTAFIVEHDFIMATYLADKVIVY
consensus  481 ****.*************.. . *.********* ********* * huhp68     536 DGVPSKNTVANSPQTLLAGMNKPLSQLEITFRRDPNNYRPRINKLNSIKDVEQKKSGNYF
wghp68     541 EGLASIDCTANAPQSLVSGMNKPLSHLDITFRRDPTNYRPRINKLESTKDREQKNAGSYY
consensus  541 .*. *   .*.*.****** *.*.***** ******* *..* .*.* huhp68     596 FLDD
wghp68     601 YLDD
consensus  601 .***
```

Figure 23
A  Mouse TCP 1      D  K  M  L  V  D  D  I  G  D  V  T  I  T  N  D
   TF 55            .  .  .  .  F  .  .  S  L  .  .  I  .  .  .  .
   Yeast TCP 1      .  .  .  .  .  .  .  .  .  .  F  .  V  .  .  .
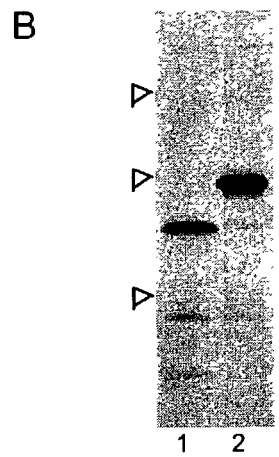

CELL-FREE　　　AUTHENTIC　　　CONTROL

VIRAL CAPSID ASSEMBLY INTERMEDIATES AND METHODS OF PRODUCTION

CROSS-REFERENCE TO RELATED APPLICATIONS

This application in a continuation in part of U.S. Ser. No. 10/040,206 filed Jan. 2, 2002 now abandoned, which is a continuation in part of U.S. Ser. No. 09/020,144, filed Feb. 6, 1998 (issued on Jul. 15, 2003 as U.S. Pat. No. 6,593,103), which claims benefit of U.S. Ser. No. 60/039,309 filed Feb. 7, 1997 (expired on Feb. 7, 1998), which disclosures are hereby incorporated by reference.

STATEMENT REGARDING FEDERALLY SPONSORED RESEARCH

This invention was made with Government support by Grant Nos. K08AI01292 and AI41881, awarded by the National Institutes of Health (NIH) and National Institutes of Health AIDS Division, respectively. The Government has certain rights in this invention.

INTRODUCTION

1. Field of the Invention

The invention is concerned with a method for producing viral capsids in a cell-free extract. Also described are capsid intermediate compositions, auxiliary proteins, and screening assays for drugs to inhibit this process. The invention is exemplified by preparation of HBV, HIV and HCV capsids in a cell free system and the identification, using this system, of host chaperones required for capsid assembly.

2. Background of the Invention

All viruses are composed of a protein shell surrounding a nucleic acid containing core. The protein shell directly surrounding the viral nucleic acid is called a capsid, whereas, the complete protein-nucleic acid complex having both the capsid and the nucleic acid is called a nucleocapsid. The capsid is composed of many subunits of capsomeres that, in turn, are composed of several homo- or heteropolymers of protein. Although the capsids of many viruses differ in protein composition, a general viral structural design has evolved characterized by the polymerized capsomeres. Arenaviruses, rotaviruses, orbiviruses, retroviruses (including lentiviruses), papillomaviruses, adenoviruses, herpesviruses, paramyvirus, myxovirus, and hepadnaviruses all exhibit these general structural features, (Virology, Fields ed., third edition, Lippencott-Raven publishers, pp 1513, 1645, 1778, 2047, 2113, 2221, and 2717 (1996).

It has been the belief that some simple viruses form capsids spontaneously from their dissociated components while others require enzyme-catalyzed modifications of the capsomers to trigger assembly. Viral capsid self assembly is driven by the stability of the interactions between protein subunits under conditions that favor association. More complex viruses are often constructed from subassemblies that have undergone self assembly processes. (Virology, Fields ed., third edition, Lippencott-Raven publishers, pp 62, 70, 1646 and 1888 (1996)).

An important benefit of understanding a viral life cycle, including capsid assembly, is the ability to develop anti-viral drugs that effectively abolish viral replication. As an example, anti-HIV drugs currently being used to treat patients infected with HIV either have minimal anti-HIV activity, produce adverse side effects or both. 3'-azido-3'-deoxythymidine (Zidovudine, AZT), the most widely recommended and used anti-HIV drug, has recently been shown to be ineffective in blocking HIV replication as a reverse transcriptase inhibitor (Papadopulos-Eleopulos et al. Curr Med Res Opin. (1991) Suppl. 1:S1-45). The triphosphorylated form of the drug does posses anti-HIV properties, however the unphosphorylated form is administered to patients and this form is not phosphorylated in vivo. In addition AZT has many adverse side effects, which in combination with its inability to reduce viral load provide for a very ineffective treatment option for HIV infected patients and many cannot tolerate it. Another drug target is the HIV protease (PR) crucial to virus development. PR is an aspartic protease and can be inhibited by synthetic compounds. (Richards, FEBS Lett., 253:214-216 [1989]). Protease inhibitors inhibit the growth of HIV more effectively than reverse transcriptase inhibitors but prolonged therapy has been associated with metabolic diseases such as lipodystrophy, hyperlipidemia, and insulin resistance.

Available treatments for HCV, such as interferon, are costly, difficult to administer, and minimally effective (Lin and Keeffe Annu Rev Med 52, 29-49 ((2001)). Most HCV patients show an improvement of clinical symptoms during interferon treatment, but relapse is observed in at least half of patients when treatment is interrupted. Despite recent breakthroughs in cellular systems for studying HCV replication, culture systems that release high titers of infectious virus do not currently exist.

The mechanisms involved in coordinating the formation of an viral capsids are not well elucidated and, many important questions about capsid assembly remain unanswered, including whether assembly generally is an energy-dependent process, whether host proteins are required for assembly to take place, and whether assembly proceeds by way of discrete intermediates. A major obstacle to addressing these questions experimentally has been the inherent difficulty of studying capsid assembly in cellular systems. Many of the events in question proceed extremely rapidly and are not readily amenable to manipulation, making it difficult to identify transacting factors and energy substrates that may be required for assembly. It therefore is of interest to identify individual steps involved in immature viral capsid assembly and to determine both the intermediates and the identity and conformation of transacting host proteins involved in the immature capsid assembly cascade as a means of developing compounds which inhibit the host proteins identified. There is a need for compounds for treatment of virally infected individuals that specifically inhibit viral replication, but do not have significant side effects and do not promote new strains of virus that are resistant to treatment.

RELEVANT LITERATURE

HCV core protein has been translated in cell-free systems, i.e. (Santolini et al (1994) *J Virol* 68, 3631-41; Yasui, et al. (1998) *J Virol* 72, 6048-55; Lo, et al, (1996) *J Virol* 70, 5177-82; and Shih, et al (1995) *J Virol* 69, 1160-71). However, assembly was not examined in these studies, which focused instead on core protein processing, post-translational modifications, and association of core with ribosomes and RNA.

SUMMARY OF THE INVENTION

This invention relates to methods for identifying and isolating viral capsid assembly intermediates, identifying host proteins that bind to these intermediates, using the host proteins and assembly intermediates to develop treatments for viral diseases by screening for drugs that specifically target the identified host proteins and/or disrupt formation of intermediates or disrupt their involvement in capsid assembly together with the various compositions so identified and/or isolated. The method for isolating the intermediates includes the steps of adding viral mRNA to a cell-free protein translation mixture; incubating the resulting mixture for a time sufficient to synthesize viral capsid assembly proteins and assemble the newly synthesized mRNA translation products into intermediates which are subsequently converted into an immature encoding at least one capsid component; separating the intermediate-host protein complexes that have formed; and isolating the complexes. The HCV capsid assembly intermediates isolated are of high molecular weight (>200S), pelleting in a 2 ml 10-30% sucrose gradient centrifuged at 55,000 rpm in a TL-S55 rotor for 60 minutes. The assembly intermediates can be used as components in a screening assay for conformers of host proteins involved in capsid assembly as well as in a screening assay for compounds which specifically inhibit the trans-acting host proteins. The intermediates and the host protein complexes can be affinity purified using antibodies to the viral protein involved in capsid assembly to which the host proteins bind and the intermediate and the associated host protein and/or conformer separated. The host protein and/or conformer can then be sequenced. Also included are monoclonal antibodies specific for the host protein. The invention finds use in identifying compounds that specifically affect the function of host proteins that are trans-acting factors involved in capsid formation and which can be expected to specifically inhibit viral capsid formation as well as in rapid diagnosis of viral infection.

BRIEF DESCRIPTION OF THE FIGURES

FIG. 7 shows plots of pulse-chase experiments in which transcripts of different assembly-defective mutants Pr46 (FIG. 7B), Pr41 (FIG. 7C), GΔA (FIG. 7D), and D2 (FIG. 7E) and wild-type HIV (WT; FIG. 7A) were analyzed for assembly in a cell-free system.

FIG. 9 shows a schematic model for assembly of immature HIV capsids (FIG. 9A) and the points along the pathway at which Gag mutants p41 (FIG. 9B), GΔA or wild-type in the absence of MCoA (Wt-MCoA; FIG. 9C), D2 (FIG. 9D) are arrested, compared to wild type in the presence of MCoA (WT+MCoA) or p46 (FIG. 9E).

FIG. 10 shows alignment of WGHP68 (SEQ ID NO:5) with HuHP68 (SEQ ID NO:6). Dashes indicate alignment gaps; asterisks, identical amino acids; dots, conserved amino acids. Open boxes; P-loop motifs. Black boxes; regions sequenced and used for constructing degenerate oligonucleotides. Arrows: residue before stop codon in WGHP68-Tr1.

FIG. 11 shows HuHP68 co-immunoprecipitates HIV-1 Gag in mammalian cells. Native (NATIVE) or denaturing (DENAT) immunoprecipitations using αHuHP68b (HP) or non-immune serum (N), followed by immunoblotting (IB) with antibody to HuHP68 (IB: HP) or Gag (IB: Gag), were performed on: (FIG. 11A) 293T cells transfected with pBRUΔenv, +/−RNase A treatment; (FIG. 11B), Cos-1 cells expressing Gag; (FIG. 11C), Cos-1 cells expressing Gag (Gag), an assembly-incompetent Gag mutant (p41), an assembly-competent Gag mutant (p46), or control vector (native immunoprecipitation only); or (FIG. 11D), chronically HIV-1-infected ACH-2 cells. HIV-1 p24 and p55 (arrows), 5% input cell lysate (T), and 10 µl medium (T medium) are indicated.

(FIGS. 12A-I), Cos-1 cells were transfected with pBRUΔenv or pBRUp41Δenv (truncated proximal to the nucleocapsid domain in Gag), and double-label indirect immunofluorescence was performed. Fields were labeled for HP68 (red, top row: FIGS. 12A, D, G), or Gag (green, middle row: FIGS. 12B, E, H). Images were merged to show overlap of HP68 and Gag labeling (yellow; bottom row: FIGS. 12C, F, I). Bar at lower right corresponds to 50 µm.

(FIGS. 13A-D), Cos-1 (FIGS. 13A, B) or 293T (FIGS. 13C, B) cells co-transfected with varying amounts of plasmid expressing WGHP68-Tr1 and empty vector, as indicated, plus plasmids for expression of HIV-1 Gag (FIGS. 13A, B) or pBRUΔenv (FIGS. 13C, B). Medium (FIGS. 13A, C) was immunoblotted with Gag antibody (p55; p24), and reprobed with antibody to light chain tracer (LC). Cell lysates (FIGS. 13B, D) were immunoblotted using WGHP68 antiserum (HP) or Gag antibody (p55; p24), and reprobed using actin antibody (actin). Arrows: open, native HP68; filled, WGHP68-Tr1. Bar graphs: blots from 3 experiments quantitated using sample dilution standard curves.

(FIGS. 14A-B), Graphs show total Gag synthesized (FIG. 14A) or amount of Gag in 750S completed capsids (FIG. 14B) from cell-free reactions programmed with indicated WG extracts: non-depleted; immunodepleted (depleted); or immunodepleted reconstituted with either GST alone (+GST), WGHP68-GST (+WGHP68), or HuHP68-GST (+HuHP68). (FIG. 14C), Amount of Gag in fractions from cell-free reactions in A that were subjected to velocity sedimentation. (FIGS. 14D, E), TEM of capsids from immunodepleted cell-free reactions reconstituted with WGHP68-GST (14D) or immature capsids from transfected mammalian cells (FIG. 14E). Bar: 100 nm. (FIG. 14F), Proteinase K digestion of 500S and 750S fractions shown as % Gag protected relative to normalized controls. Open circle in 14D is depleted and closed circles are reconstituted (GST); filled bars in 14E are 500S intermediates and diagonal lines are 750S assembled capsids (FIG. 15A), Cos-1 cells transfected with pBRUΔenv or HIV-1 Gag plasmids were immunoprecipitated under native (NATIVE) or denaturing (DENAT) conditions using αHuHP68b (HP) or non-immune serum (N), and immunoblotted (IB) with antibody to HuHP68 (HP), HIV-1 Gag, HIV-1 Vif, HIV-1 Nef, RNase L (RL), or Actin. Total (T): 5% of input cell lysate used in immunoprecipitation (HP: 10%). Top of some actin lanes contains heavy chain cross-reacting to secondary. (FIG. 15B) shows the results with lysates of pBRUΔenv-transfected Cos-1 cells, harvested in 10 mM EDTA-containing buffer, and co-immunoprecipitated using beads pre-incubated with HuHP68 peptide or diluent control.

FIG. 23 shows preparation and characterization of a polyclonal antiserum against a cytosolic chaperonin. A shows alignment of an amino acid sequence present within mouse TCP-1 (positions 42-57) (Lewis et al. 1992 Nature 358:249-252), S. shibatae TF55 (a heat shock protein of a thermophilic archaebacterium) (positions 55-70) (Trent et al. 1991 Nature 354:490-493) and yeast TCP-1 (positions 50-65) (Ursic and Culbertson, 1991 Mol. Cell Biol. 11:2629-2640). Amino acids identical to those in the mouse sequence are designated by (.). A synthetic peptide was synthesized corresponding to amino acids 42-57 from mouse TCP-1 because of the high degree of homology in this region. This peptide was conjugated to carrier protein or cross-linked to itself and used to generate rabbit polyclonal antisera (anti 60). Immunoprecipitations were performed with this antiserum under denaturing conditions on whole cell extracts of steady state, [35S]methionine-labeled HeLa cells. A protein of 60 kD was precipitated by anti 60, shown in B, lane 1. As a control, B, lane 2 shows an immunoprecipitation under denaturing conditions done with antiserum to hsp 70 in the same experiment. Molecular weight markers (92, 68, and 45 kD) are indicated to the left with open arrowheads. Under native conditions, anti 60 also immunoprecipitates a 60-kD protein in solubilized HeLa cells. To further characterize the antigen recognized by this antiserum, rabbit reticulocyte extract and wheat germ extract were layered onto 10-50% sucrose gradients, centrifuged at 55,000 rpm for 60 min in a TL-100 Beckman ultracentirfuge, fractionated, and analyzed by SDS-PAGE. The proteins were transferred to nitrocellulose and were immunoblotted with anti 60 as shown in C. To determine S values, protein standards were centrifuged in a separate gradient tube at the same time and fractions were visualized by Coomassie staining of SDS-PAGE gels. The positions of these markers (BSA and α-macroglobulin) are indicated with arrows. Molecular weight markers (68 and 45 kD) are indicated to the right with open arrowheads. In both immunoblots, only a single band was recognized, representing a 60-kD protein, migrating in the 20-S position. Thus, anti 60 appears to recognize a 60-kD protein (CC 60) that migrates in the 20-S region and is likely to be either TCP-1 or homolog.

DETAILED DESCRIPTION OF THE INVENTION

Figure 1:
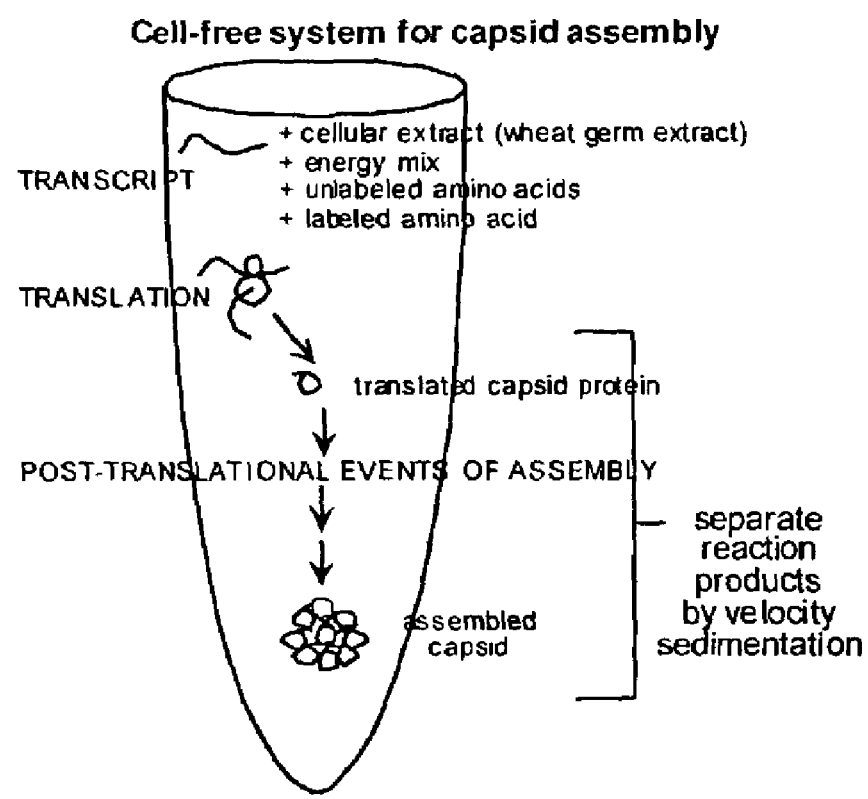
FIG. 1 shows a diagram of a cell-free system for viral capsid assembly. Capsid transcript is synthesized in vitro and added to wheat germ extract, an energy regenerating system, 19 unlabeled amino acids, and one labeled amino acid ($^{35}$Smet or $^{35}$Scys). Reactions are incubated at 26° C. for 150 min. Translation of capsid proteins is followed by a series of post-translational events (that differ for various types of viral capsids), resulting in 20-40% of capsid chains forming completely-assembled capsids. At the end of the reaction, products of different sizes (i.e. unassembled, partially-assembled, and completely-assembled core polypeptides) can be separated from each other by velocity sedimentation on sucrose gradients.

The present invention uses a cell-free system for translation and assembly of viral capsids. The cell-free system is programmed using viral mRNA molecules encoding capsid protein(s); immature capsids are produced after incubation for a period of time sufficient to assemble capsid protein mRNA translation products. Capsid assembly intermediates and trans acting host proteins involved in capsid assembly are isolated and identified. This information is then used in screening for antiviral compounds that inhibit host proteins and/or conformers thereof that are involved in viral replication; candidate compounds can also be screened for using the cell free translation system. The phrase "cell-free translation" refers to protein synthesis carried out in vitro in a cell extract that is essentially free of whole cells. The phrase "cell-free translation mixture" refers to a cell free extract that generally includes sufficient cellular machinery and components to support protein translation which includes transfer RNA, ribosomes, a full complement of at least 20 different amino acids, an energy source, which may be ATP and/or GTP, and an energy regenerating system, such as creatine phosphate and creatine phosphokinase. The term "conformer" refers to two or more proteins having at least substantially the same amino acid sequence, but having heterogeneity in structure (physical topology or topography) and function. By topology is intended the different placement of the protein, e.g. C-cytosolic as compared to N-cytosolic, and topography intends change in external conformation or shape, (i.e. different three-dimensional shape due to differences in folding/conformation), which includes stable and/or transient association with other proteins. As used herein, polypeptides of substantially the same amino acid sequence are those with conservative amino acid substitutions (i.e. a small or large side chain for a small or large side chain, respectively; or an acidic, basic, polar or hydrophobic side chain for an acidic, basic, polar or hydrophobic side chain, respectively), that do not alter protein conformation or topology. The protein conformation changes are due to post-translational modifications and are not a result of differences in the amino acid sequence.

The subject invention offers several advantages over existing technology. A major advantage of the cell-free system is that it is amenable to a wide variety of manipulations. For example, since the only radiolabeled protein used generally is the capsid protein, it is an ideal system to use for pulse-chase analysis, in which a cohort of protein is followed over time. Furthermore, the reactions can be separated out into a protein synthesis phase and an assembly phase, and manipulations can be performed to address energy requirements during the assembly phase, independent of the synthesis phase. Other manipulations that can be performed, include reducing the concentration of transcript, removing RNA using RNAse A after protein synthesis is completed but while assembly is just starting, solubilizing membranes using detergent at the start of translation, and selectively removing specific factors from the extract before programming the reaction. This ability to manipulate the reaction allows testing of hypotheses concerning the mechanism of capsid assembly. In cellular systems, viral capsid assembly occurs too rapidly and efficiently to be easily dissected biochemically, but an advantage offered by the cell-free system is that once the mechanisms involved have been defined using the cell-free system, approaches can be devised to demonstrate the existence of these mechanisms in cellular systems. An example of this approach is the energy requirement of retrovirus capsid assembly, which was initially defined for HIV-1 in the cell free system, and subsequently was confirmed for M-PMV in cells (Welson, et al., (1998) *J Virol* 72, 3098-106.) Thus, cell-free systems have the unique ability to foster advances in understanding of biochemical mechanisms underlying complex cellular events, thereby stimulating new experimental approaches in other systems.

The cell-free system, since it recreates capsid biogenesis, greatly facilitates biochemical dissection and mechanistic understanding of capsid formation. Immature capsids can be assembled in a cell-free protein translation system, when certain key components are added to the reaction, even for viruses such as HCV which lack cell culture systems that produce high titers of virus. Furthermore, this method for cell-free assembly of viral capsids reveals the existence of previously unknown steps in virus formation, allowing disassociation of the process of capsid formation into co- and post-translational phases, each of which has distinct co-factor and/or energy requirements, and the identification of host factors that are involved in capsid assembly.

Another advantage of the subject invention is that by slowing down the process of capsid formation, previously unrecognized assembly intermediates could be identified, in both cells and in the cell-free system. Identification of these previously unknown intermediates provides new targets that can be used in the design of drugs (including peptides and antibodies) and vaccines that interfere with progression from one intermediate to the next, in the design of drugs that act by inhibiting host cell machinery involved in capsid formation, and in the design of assay systems that examine the efficacy and mechanism of action of drugs that inhibit capsid formation.

This system also offers the advantage that it can be used for identifying drugs that interfere with the process of capsid formation. Such a system includes a screening assay for host proteins and/or conformers functioning as chaperones in viral replication or as a selection assay for identification of new compounds that interfere with capsid formation by specifically inhibiting the chaperones, and hence production of infectious virus. By identifying these chaperones, drugs can be designed that block or alter the association of the chaperone(s) with viral proteins to prevent formation of immature viral capsids. Since the target for the drug is a host protein rather than a viral protein, there is a decreased likelihood of the development of viral resistance to such a drug.

Another advantage of the subject invention is the discovery that pieces of genomic nucleic acid can be encapsidated into the capsids produced in the cell-free system by adding such nucleic acid to the system. This feature of the invention can be used to design drugs that interfere with encapsidation and in the design of assay systems that examine the mechanism of action of drugs that inhibit encapsidation.

The present invention includes a method for producing viral capsid assembly intermediates in a cell-free system. Assembly of immature capsids in cells requires expression of only the particular viral protein involved in capsid assembly, such as the HIV Pr55 protein, for HIV and the core protein for HCV and HBV. These cell-free assembly systems (for UBV, HIV-1, HCV, M-PMV, and other capsids) have similarities and differences that reflect differences in virion morphogenesis. For example, for HIV-1 capsid assembly, both myristoylation machinery and membranes must be present, while these are not required for either HBV or HCV capsid assembly in which the structural proteins are not myristoylated, and in which targeting to the membrane is believed to occur after capsid assembly.

In the capsid assembly system (see FIG. 1), capsid transcript is synthesized in vitro and used to program the translation of radiolabeled capsid polypeptides in the presence of a eukaryotic extract, unlabeled and labeled amino acids, and an energy-regenerating system (Erickson and Blobel (1983) *Methods Enzymol* 96, 38-50). Once synthesized, these polypeptides proceed to assemble into capsids. Known in the art are a number of in vitro translation systems, the basic requirements of which have been well studied (Erickson and Blobel, Methods Enzymol (1983) 96:38-50; Merrick, W. C., Methods Enzymol. (1983) 101:606-615; Spirin et al. Science (1988) 242:1162-1164). Examples include wheat germ extract and rabbit reticulocyte extract, available from commercial suppliers such as Promega (Madison, Wis.), as well as high speed supernatants formed from such extracts. While the cell-free translation mixture can be derived from any of a number of cell types known in the art that contain the necessary components for assembly of the cell-free system of the present invention is exemplified using wheat germ cell-free extract. As an example, necessary components for HIV capsid formation include a protein that binds to 23c antibody. Therefore, in some instances, it may be necessary to supplement the cell-free system with exogenous proteins, such as host protein, which facilitate the assembly of capsid intermediates. As an example, rabbit reticulocyte extract does not support production of HIV capsids in the absence of added host factor 68

(HP68.) To produce mutant capsid intermediates, the system is programmed, for HIV mutants, with mutant nucleic acids, such as Pr46, Pr41, GΔA and D2, which are well known in the art. Typically wheat germ extracts are used which are prepared from the germ of wheat of different strains. (Erickson and Blobel. The extract is the source of factors known to be required for translation, plus factors that have not yet been defined and may be required for assembly.

For viruses such as HIV, which have myristolated intermediaries, it is necessary to add sufficient myristoyl coenzyme A (MCoA) to the system to enable assembly of capsids. While the concentration required varies according to the particular experimental conditions, in experiments carried out in support of the present invention, it was found that for HIV a concentration of between about 0.1 and 100 µM, and preferably between about 5 and 30 µM, supports capsid formation. Without committing to a particular theory concerning the mechanism of the reaction, it is likely that this supplement promotes myristoylation of the Gag translation product and attachment to membrane fragment(s) present in the cell free translation mixture. For viruses other than HIV, the amount of McoA required for capsid assembly can be determined empirically.

Proteins and peptides produced during a viral infection may be present in infected cells in the cytosol, or may be integral in the cell membrane. Both cytosolic and integral membrane proteins may be involved in viral replication. Integral membrane proteins may include transmembrane proteins, which are generally important for immune recognition of infected cells and as a target for immunotherapy. For viruses which require membrane proteins for capsid assembly, appropriate membranes can be added to the cell-free translation mixture. As an example, for HIV when membranes present in the cell free translation mixture are solubilized by addition of detergent, assembly of the HIV capsid is sensitive to addition of detergent above but not below the critical micelle concentration. This observation is consistent with a role for membranes being required at a particular step in capsid assembly. Furthermore, HIV capsid assembly is improved by the presence of a cellular component that has a sedimentation value greater than 90S in a sucrose gradient and is insensitive to extraction with at least 0.5% "NIKKOL".

Methods known in the art are used to maintain energy levels sufficient to maintain protein synthesis, for example, by adding additional nucleotide energy sources during the reaction or by addition of an energy source, such as creatine phosphate/creatine phosphokinase. The ATP and GTP concentrations present in the standard translation mixture, generally between about 0.1 and 10 mM, more preferably between about 0.5 and 2 mM, are sufficient to support both protein synthesis and capsid formation, which may require additional energy input. Generally, the reaction mixture prepared in accordance with the present invention can be titered with a sufficient amount of ATP and/or GTP to support production of a concentration of about 10 picomolar viral protein in the system. For membrane requiring the translation mixture also can include detergent-sensitive, detergent-insensitive, and host protein fractions described below, or it may be supplemented with such fractions. The term "detergent-sensitive fraction" refers to a component most likely containing a membrane lipid bilayer that is present in a standard wheat germ extract prepared according to the methods described by Erickson and Blobel (1983) (Methods in Enzymalogy Val 96), which component is deactivated with reference to supporting HIV capsid assembly when a concentration of 0.1% (wt/vol) "NIKKOL" is added to the extract. It is appreciated that such a detergent-sensitive factor can be present in extracts of other cells similarly prepared, or can be prepared independently from a separate cell extract, and then added to a cell-free translation system.

The cell-free translation mixture is programmed with transcript nucleic acid or a fraction thereof, whereby the system is capable of making capsids containing viral nucleic acid. The term "programmed with" means addition to a cell-free translation mixture or cells, mRNA that encodes viral proteins, or by adding to cells a DNA sequence that specifies the production of such viral protein. Viral mRNA can be added to cells directly, such as by transfection or electroporation according to methods well known in the art. DNA that directs the production of mRNA can also be used to program the cell-free system or "added to cells" by inserting the corresponding gene into an appropriate vector and transfecting the cell. The cell-free translation reaction is initiated by adding viral mRNA. Suitable mRNA preparations include a capped RNA transcript produced in vitro using the mMESSAGE mMACHINE kit (Albion). RNA molecules also can be generated in the same reaction vessel as is used for the translation reaction by addition of SP6 or 17 polymerase to the reaction mixture, along with the viral capsid protein coding region or cDNA. For HIV, the coding region encoding Gag Pr55 can be obtained, for example, by DNA synthesis according to standard methods, using the sequence provided as SEQ ID NO: 1. Alternatively the plasmid described in Examples, pBRU-Aenv, which codes the entire HIV genome except for the envelope protein sequence, can be used. Assembly of immature capsids in the cell-free system requires expression of only the particular viral protein(s) that are involved in capsid assembly. A sample containing a virus of interest or a bodily fluid of an individual infected with a virus of interest, or infected cells from an individual, is used as a source of viral nucleic acid encoding the capsid protein(s) for the virus. The fluid may be any bodily fluid including blood, serum, plasma, lymphatic fluid, urine, sputum, cerebrospinal fluid, or a purulent specimen. The genomes for many viruses, have been sequenced, for example see the web sites at www.ncbi.nim-.nih-.gov:80/entrez/query.fcgi?db-Genome. and www.ncbi.n-im.nih.gov:80/entrez/query.fcgi?db-Genome>.

After incubation for a time sufficient to produce capsids, products of the cell-free reaction are analyzed to determine sedimentation (S) value (which assesses size and shape of the particle), buoyant density (which indicates the density of the particle) and electron microscopy appearance. Together these form a sensitive set of measurements for integrity of capsid formation. A fourth criterion (resistance to protease digestion) also can be used. To confirm that the de-enveloped particles obtained represent the desired viral capsids, the fractions containing de-enveloped capsids from the velocity sedimentation gradient are analyzed by equilibrium centrifugation on CsCl and the buoyant density compared with that of capsids (without envelopes) produced in infected cells.

The cell-free capsid assembly reaction described above can be extended to include packaging of nucleic acid, by addition of genomic nucleic acid or fragments thereof during the capsid assembly reaction. Addition and monitoring of encapsidation provides an additional parameter of particle formation that can be exploited in drug screening assays, in accordance with the present invention. The nucleic acid preferably is greater than about 1,000 nucleotides in length and is subcloned into a transcription vector. A corresponding RNA molecule is then produced by standard in vivo transcription procedures. This is added to the reaction mixture described above, at the beginning of the incubation period. Although the final concentration of RNA molecule present in the mixture will vary, the volume in which such molecule is added to the reaction mixture should be less than about 10% of the total volume.

Preparation of viral capsids in the cell-free capsid assembly system is used to identify novel previously unrecognized assembly intermediates, and provides means for identification of additional assembly intermediates. As discussed in more detail below, such intermediates are useful as (i) antigens for production of antibodies and/or vaccines, (ii) along with such antibodies, as standards in diagnostic tests, (iii) as vehicles for identification of key host cellular proteins involved in capsid assembly and (iv) drug targets. Exemplified herein are a capsid assembly pathway and intermediates thereof that have been identified for HIV, HBV, HCV, and similar pathways by analogy are used by other capsid assembly mechanisms, and that the intermediates described herein have analogous counterparts in such capsid assembly systems. These counterparts can be identified using the general manipulations described below.

Capsid assembly intermediates can be formed in a number of ways, including (i) translation of capsid assembly mutant coding sequences in cells or in cell-free preparations, and (ii) by blocking the production of capsids in a cell-free assembly system, such as by adding specific assembly blockers (e.g. apyrase to block ATP) or by subtraction of a key component, such as MCoA, for HIV, from the reaction, resulting in production of one or more assembly intermediates in large quantity.

At least one host cell-derived assembly protein generally is involved in capsid formation. The presence of such a protein in a cell extract is detected by any of a number of means, including immunoprecipitation of the host protein-assembly intermediate complex. Alternatively, the host protein can be added exogenously to the system. Host cell proteins are characterized by (i) immunoreactivity with monoclonal antibody to known host proteins and (ii) by whether they contain amino acid sequences from known host proteins. The protein is further characterized by molecular weight (for example, as assessed by SDS-PAGE). Specific blockade of the reactivity of these host proteins can provide new therapeutic regimens for blocking virus production.

The host proteins identified using the cell-free system can be obtained from any of a variety of sources, including wheat germ and primate homologues, particularly human. Human homologues can be identified using degenerate primers to the identified sequence, or other chaperone proteins identified in a cell free system that bind to the capsid assembly intermediates of the virus of interest, and then cloned into an expression vector. Translation products from these expression vectors are tested in a cell free system to determine their ability to bind capsid assembly proteins of the virus of interest by immunopurification.

Host proteins can be identified that are involved in viral replication which, when present as alternative conformers, have different activities or functions. For cytosolic proteins, this is accomplished by (i) first producing knockout mice for cytosolic proteins of interest; (ii) generating monoclonal antibodies to probe for conformational specificity, (iii) epitope mapping the conformer; and (iv) in parallel, characterizing the cytosolic proteins in the different complexes and under the conditions that generate one conformer versus another.

Any protein for which evidence suggests conformational heterogeneity can be assessed as a candidate for having a conformer. For example, HP68 is a protein the normal function of which is unknown but which contains an ATP binding site. It has been implicated in two distinct functional assays in viral infection: as a molecular chaperone for viral capsid assembly in HIV infected cells (see Example 5) and as an RNAse L inhibitor (Bisbal et al., J. Biol Chem (1995) 270: 13308-17). These activities are mutually exclusive, i.e., the conformer of HP68 that acts as a chaperone in HIV capsid assembly and binds to Gag does not bind to RNAse L and vice versa. These distinctive functional assays suggest that each conformer occurs in vivo under different circumstances and makes possible the direct determination of conditions that favor one versus the other pathway of biogenesis for nascent HP68 or other candidate conformers. The existence of such conformers makes possible drug targets for inhibiting viral replication that inhibit a single function of the host protein, as opposed to all functions of the host protein, if only one particular conformer is targeted.

Constructs containing cloned cDNA of a suspected conformer can be engineered and expressed in a cell-free system or in transfected mammalian cells (see Example 5 and Hegde et al. Nature (1999) 402:822-826). Radiolabeled amino acid incorporation into specific proteins of interest are assessed by solution immunoprecipitation under native versus denatured conditions and analysis by SDS-PAGE and autoradiography (AR). Nascent chains are analyzed in various ways (e.g. truncation and crosslinking (Hegde et al. Cell (1997) 90:31-41)) to correlate aspects of biogenesis to conformational heterogeneity of the completed polypeptides. The systems, cell free or transfected cells, can be manipulated in various ways (Rutkowski et al. PNAS (2001) 98:7823-7828; Hegde et al. Molecular Cell (1998) 2:85-9) (e.g. viral replication, temperature, energy) and the correlation of effect on biogenesis and effect on final protein conformation can be determined. For cytosolic proteins, analysis will focus on the mechanisms of formation of two (or more) distinct complexes which are readily detected (Sen et al. JBC (1992) 267(8):5017-20; Gorlich et al. Nature (1992) 357:47-52). In addition, the biosynthetic heterogeneity of cytosolic proteins can be characterized and parameters identified that alter the distribution of conformers (see Example 5; and Rutkowski et al., PNAS (2001) 98:7823-7828).

Monoclonal antibodies can be produced to corroborate the functional assay results and show, based on epitope mapping, that (i) antibodies to the same epitopes do not bind proteins that contain essentially the same amino acid sequences; and (ii) alternative folding of proteins masks or uncovers epitopes and renders them immunologically, and thus structurally, distinct. Sequencing of the cloned suspected conformer is conducted to demonstrate that the proteins have essentially the same amino acid sequence. Thus, monoclonal antibodies to a mapped epitope can be used to identify conformers with different structural, and, by implication, functional characteristics which can be used as specific drug targets, thus decreasing potential side effects. Monoclonal antibodies can be used with unpurified lysates from either transfected cells or a programmed cell-free system.

Monoclonal antibodies can be prepared by any number of ways which are known to those skilled in the art and previously described (see, for example, Kohler et al., Nature, 256: 495-497 (1975) and Eur. J. Immunol. 6:511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory Press, Cold Spring Harbor, N.Y. (1989); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line) with antibody-producing cells (for example, lymphocytes derived from the spleen or lymph nodes of an animal immunized with an antigen of interest). The cells resulting from a fusion of immune cells and lymphoma cells, generally referred to as hybridomas, can be isolated using selective culture conditions, and then cloned by limiting dilution. Cells which produce antibodies with the desired binding properties are selected by a suitable assay, such as a serological assay, including enzyme-linked immunosorbent assay (ELISA).

Functional binding fragments of monoclonal antibodies also can be produced by, for example, enzymatic cleavage or by recombinant techniques. Enzymatic cleavage methods include papain or pepsin cleavage to generate Fab or F(ab')$_2$ fragments, respectively. Antibodies also can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain. Functional fragments of the monoclonal antibodies retain at least one binding function and/or modulation function of the full-length antibody from which they are derived. Preferred functional fragments retain an antigen-binding function of a corresponding full-length antibody (e.g., retain the ability to bind an epitope of a conformer). In another embodiment, functional fragments retain the ability to inhibit one or more functions characteristic of a protein or peptide conformer, such as a binding activity, a signaling activity, and/or stimulation of a cellular response. For example, in one embodiment, a functional fragment can inhibit the HIV capsid assembly.

One method of developing conformer specific antibodies is to immunize knock-out mice that lack a functional gene for the protein of interest with a putative conformer of the protein of interest. Knockout mice can be produced using standard techniques known to those skilled in the art (Capecchi, Science (1989) 244:1288; Koller et al. Annu Rev Immunol (1992) 10:705-30; Deng et al. Arch Neurol (2000) 57:1695-1702); the gene corresponding to the protein against which monoclonal antibodies are to be raised is knocked out, e.g. HP68. A targeting vector is constructed which, in addition to containing a fragment of the gene to be knocked out, generally contains an antibiotic resistance gene, preferably neomycin, to select for homologous recombination and a viral thymidine kinase (TK) gene. Alternatively, the gene encoding diphtheria toxin (DTA) can be used to select against random insertion. The vector is designed so that if homologous recombination occurs the neomycin resistance gene is integrated into the genome, but the TK or DTA gene is always lost. Murine embryonic stem (ES) cells are transfected with the linearized targeting vector and through homologous recombination recombine at the locus of the targeted gene to be knocked out. Murine ES cells are grown in the presence of neomycin and gancyclovir (for TK), a drug that is metabolized by TK to produce a lethal product. Thus cells that have undergone homologous recombination are resistant to both neomycin and ganciclovir. Vectors containing DTA kill any cell that codes for the gene, so no additional drug is required in the cell culture medium. Southern blotting hybridization and PCR are used to verify the homologous recombination event, techniques well known to those skilled in the art.

To generate a mouse carrying a disrupted targeted gene, positive ES cells are propagated in culture to differentiate and the resulting blastocyte is implanted into a pseudopregnant female. Alternatively the ES cells are injected back into the blastocoelic cavity of a preimplantation mouse embryo and the blastocyte is then surgically implanted. The transfected ES cells and recipient blastocytes can be from mice with different coat colors, so that chimeric offspring can be easily identified. Through breeding techniques homozygous knockout mice are generated. Tissue from these mice is tested to verify the homozygous knockout for the targeted gene, for example using PCR and Southern blotting hybridization.

In an alternate method, gene targeting using antisense technology can be used (Bergot et al., JBC (2000) 275:17605-17610). The homozygous knockout mice are immunized with purified host protein peptides, both native and denatured recombinant protein. Following subsequent boosts, at 3 and 6 weeks, with the immunogen, the mice are sacrificed and spleens taken and fusion to myeloma cells carried out (Korth et al. Methods in Enzymol. (1999) 309:106). Antibodies from individual hybridomas are screened for conformational specificity, i.e., binding with substantial specificity to a single conformer. The screening process is carried out with radiolabeled protein products produced in the cell-free translation system or radiolabeled media or cell extracts chosen to enrich one versus another conformer. These products are immunoprecipitated using hybridoma supernatant and run on a SDS-PAGE gel. Preferably cell-free extracts are used due to the possibility that the use of transfected cells would result in protein-protein interactions which would block antibodies from binding a specific epitope, thus masking a potential conformer. The use of an immunoprecipitation screen with radiolabeled translation products, the conformation of which has been skewed (e.g. by viral infection), is the key that distinguishes this screen from a conventional approach to monoclonal antibody production. The use of 96 well plates for screening streamlines the process, allowing a single technician to screen up to 1000 individual hybridomas in a single day.

For understanding and treating a disease in which host protein or peptide conformers are involved, it is useful to identify one or more antibodies that are substantially specific for a host conformer. This method involves contacting a number of conformers with a number antibodies, or binding fragments derived from specific antibodies. The specificity of binding of the antibodies or fragments to individual conformers is then evaluated. Those antibodies or fragments that are substantially specific for each of the various conformers may thus be identified.

Sequencing of the protein conformers to which monoclonal antibodies have been raised against will show that the conformer proteins contain essentially the same amino acid sequence as the native host protein. Therefore, it is not necessary to develop an epitope map based on linear peptides but instead the protein should be mapped for conformational, or discontinuous, epitopes. The different specificity of the monoclonal antibodies is derived from the different folding of the same amino acid sequence. Thus, conformational epitope mapping is necessary to prove that the monoclonal antibodies are binding to restricted epitopes. Mapping also can be used to identify the binding sites between capsid proteins (assembly intermediates) and host chaperone proteins; binding sites on the capsid and host proteins are all potential drug targets.

Discontinuous epitopes can be identified by utilizing limited proteolysis of the antibody bound to a conformer of the protein of interest and then analyzing the lysate using mass spectrometry (MS). Monoclonal antibodies (MAb) are bound to a solid support and lysates containing the conformer protein are incubated with the immobilized Mab. Following removal of unbound protein, selected diluted proteases are added to the immobilized Mab-conformer complexes and unbound cleavage products are removed. The bound conformer proteins are eluted, under appropriate conditions, and analyzed by LC-MS. Sequencing of the conformer protein and molecular modeling are necessary to fully identify the conformational epitope. Alternatively, binding between capsid proteins and host proteins in capsid assembly intermediates can be analyzed and the binding sites identified using technology developed by Biacore AB (www.biacore.com).

The cell-free system can be used to identify possible compounds that inhibit host proteins necessary for the production of viral particles, which can then be screened for their ability to inhibit viral replication. Upon identification of compounds of interest, the compounds are tested in human cells under similar conditions.

Population profiles of conformers associated with disease severity or other characteristics can be developed by contacting a fluid of an individual with HIV, or infected cells from the individual, with one or more monoclonal antibody specific for a host protein and/or conformer thereof involved in the disease. The fluid may be any bodily fluid including blood, serum, plasma, lymphatic fluid, urine, sputum, cerebrospinal fluid, or a purulent specimen. A binding fragment derived from a monoclonal antibody specific for a host protein and/or conformer also can be used. The monoclonal antibody or binding fragment is labeled with a detectable label, for example, a radiolabel or an enzyme label. Examples of enzyme labels that may be linked to an antibody include horseradish peroxidase, alkaline phosphatase, and urease, and methods for linking enzymes with antibodies are well known in the art. The label may be detected using methods well known to those skilled in the art, such as radiography, or serological methods including ELISA or blotting methods. The presence of the label is indicative of the presence of at least one protein or peptide conformer in the individual, and may be used to identify those host proteins and/or conformer profiles that play a role in the disease process. Detection of the label in a bodily fluid indicates the presence of at least one protein and/or peptide conformer thereof in the individual. A plurality of monoclonal antibodies or their binding fragments can similarly be used to detect a plurality of host proteins and/or conformers associated with a disease state in an individual.

By detecting and characterizing host proteins and/or conformers associated with a disease in a number of individuals in a population, a profile of the various host proteins and/or conformers associated with the disease can be developed. Establishing a host protein and/or conformer profile in such a population is conducted by detecting and characterizing host proteins and/or conformers associated with any given disease in individuals, compiling the data within the population, and then establishing the relationship between host proteins and/or conformer profiles of the individual members of the population and specific characteristics of the disease in the individuals. These specific characteristics will depend on the disease and the nature of the protein or peptide and/or conformer, and can be used not only for a definitive disease diagnosis but also for determining prognosis and developing an appropriate treatment for individual patients. For example, various viral and/or host protein or peptide conformers may be associated with greater or lesser disease severity. As another example, host protein and/or peptide conformers may be associated with greater or lesser disease resistance. The response of the individuals within the population to various disease treatments is an important factor in profiling the relationship between the conformer profile of an individual and their responsiveness. Individuals that respond poorly to treatment, for example, may have conformational forms of a protein or peptide involved in the disease process that make poorer targets for the treatment than the conformational forms of the protein or peptide in individuals that respond well to treatment. Population studies can be done to establish these relationships between host proteins and/or conformers and response with a reasonable degree of significance.

Once a relationship between a host protein and/or conformer profile and treatment efficacy is established in a population, the selection of a treatment for any given patient can be improved by determining the conformer profile an individual patient using, for example, the antibody- or antibody fragment-based methods described above. Those treatment regimens that have been established as successful for individuals with substantially similar conformer profiles to that of the instant patient are most likely to prove efficacious.

The methods and compositions described herein have a number of uses. For example, the cell-free translation/assembly system can be used to produce large quantities of wild-type viral capsids, capsid intermediates or mutant capsids, as demonstrated in the studies described herein. Such capsids and intermediates can be used, for example to produce vaccines. They also find utility as reagents in screening assays that assess the status of viral capsid formation or in assays used for screening for drugs that interfere with viral capsid formation, and also can be used as a diagnostic for determining the identities of a virus causing a viral infection. The assay can be set up according to any of a number of formats. To screen for compounds that block or impair viral capsid formation monoclonal or polyclonal antibodies are used directly. Preferably such compounds do not activate host stress responses. High throughput screening of compounds for lead candidates can be carried out using any of a variety of techniques known to those of skill is the act such as, for example by screening for inhibition and/or reversal of the distinctive immunofluorescent pattern of binding of Gag and HP68, (see FIG. 12). For HIV these lead compounds are then further tested for specificity. In another such assay, cell-free translation and assembly is carried out (in the presence or absence of a candidate drug) in a liquid phase (see Example 1). The reaction product is then added to a solid phase immunocapture site coated with antibodies specific for one or more of the viral capsid assembly intermediates originally identified using the cell-free translation system, or the complete viral capsid described above. In this way, the precise point of assembly interference of the drug can be determined. Such information can be used to identify potential treatments, or combination therapeutics against viral infection, by targeting different aspects of viral replication.

A compound that is found to block viral capsid formation by binding to an active site on an assembly intermediate and/or host protein is then tested in mammalian cells infected with the virus of interest. Compounds are also screened for toxicity including host stress responses such as activation of heat shock proteins (HSP) 70, 80, 90, 94 and caspases (Flores et al., J. Nueroscience (2000) 20:7622-30). Methods for evaluating activation of these proteins are well known to those skilled in the art. Lead compounds can first be identified based on searches of databases for compounds likely to bind an active site involved in capsid assembly then tested in a cell-free system for inihibition of capsid formation.

Host cell proteins, exemplified by the HIV specific HP68 conformer, also form a part of the present invention, and have distinctive utilities. This protein, obtainable from wheat germ extract, is identified as being involved in HIV capsid assembly, as evidenced by its association with HIV capsid assembly intermediates, especially intermediates B, C, and D, and is characterized as having a peptide region having the sequence presented as SEQ ID NO: 2 and SEQ ID NO:5, specific immunoreactivity with monoclonal antibody 23 c, and an apparent molecular weight of about 68 kilodaltons. The protein is characterized by at least 60% amino acid sequence identity to human HP68, herein termed WGHP68. It is appreciated that such a protein can be derived from any of a number of host cell sources, including, human cells or produced by recombination and/or synthesized in whole or in part.

Host proteins and/or conformers, thereof involved in HIV replication can be identified. Host cell proteins involved in capsid formation or specific antibodies directed to such proteins, can be used to monitor capsid formation. In addition, association of the host protein with specific capsid assembly intermediates can be assayed directly, and such an assay also can be used as a screening assay for drugs that interfere with capsid assembly by interfering with the association of HP68 and HIV Gag and Vif proteins. This can be accomplished using compounds that bind to the active site on either the capsid proteins or host chaperone proteins; the active site is the binding site on each protein for the other, eg. HP68-Gag.

The invention also can be used to identify other host and viral proteins that are involved in regulation of capsid formation. As exemplified in FIG. 13, transfection of an HIV infected mammalian cell with a dominant negative mutant of Gag blocks HIV release. Stably transfected cells can be utilized to screen for other host or viral proteins required for capsid formation by further transfecting these cells with pooled genomic or cDNA clones and screening for clones that are able to restore HIV capsid formation. Thus, clones are selected for their ability to block the HP68 dominant negative mutants from inhibiting viral release from cells.

The invention also can be used as a means of identifying compounds that inhibit HIV capsid formation, by adding to a cell a compound that has been selected for its ability to inhibit capsid formation or formation of capsid intermediate(s) in the cell-free translation system described herein. As a related feature, the invention also extends to provide a method of selecting compounds effective to alter HIV capsid formation in cells. According to this feature of the invention, the test compound is added to cells that are forming HIV retroviral capsids. The quantity and nature of capsid intermediates formed is measured and compared to capsids formed in control cells. The compound is selected if the quantity or nature of intermediates measured in the presence of the compound is significantly different than those formed in the absence of the compound. Association of host assembly protein HP 68 with capsid intermediates can be used as a measurement in such a selection method, as well.

The cell free system can be used with plasmids that code for the entire HIV genome, except for envelope protein. Thus, the invention includes a method of encapsidating genomic HIV RNA or fragments thereof. Genomic HIV RNA, RNA fragment or a plasmid encoding HIV RNA is added to such a system, and is encapsidated during the reaction process.

The following examples illustrate, but in no way are intended to limit, the present invention.

EXAMPLES

Materials

1. Chemicals

Chemical sources are as follows, unless otherwise indicated below: Nonidet P40 (NP40) was obtained from Sigma Chemical Co. (St. Louis, Mo.). "NIKKOL" was obtained from Nikko Chemicals Ltd. (Tokyo, Japan). Wheat Germ was obtained from General Mills (Vallejo, Calif.). Myristoyl Coenzyme A (MCoA) was obtained from Sigma Chemical Co. (St. Louis, Mo.).

2. Plasmid Constructions

Figure 13:
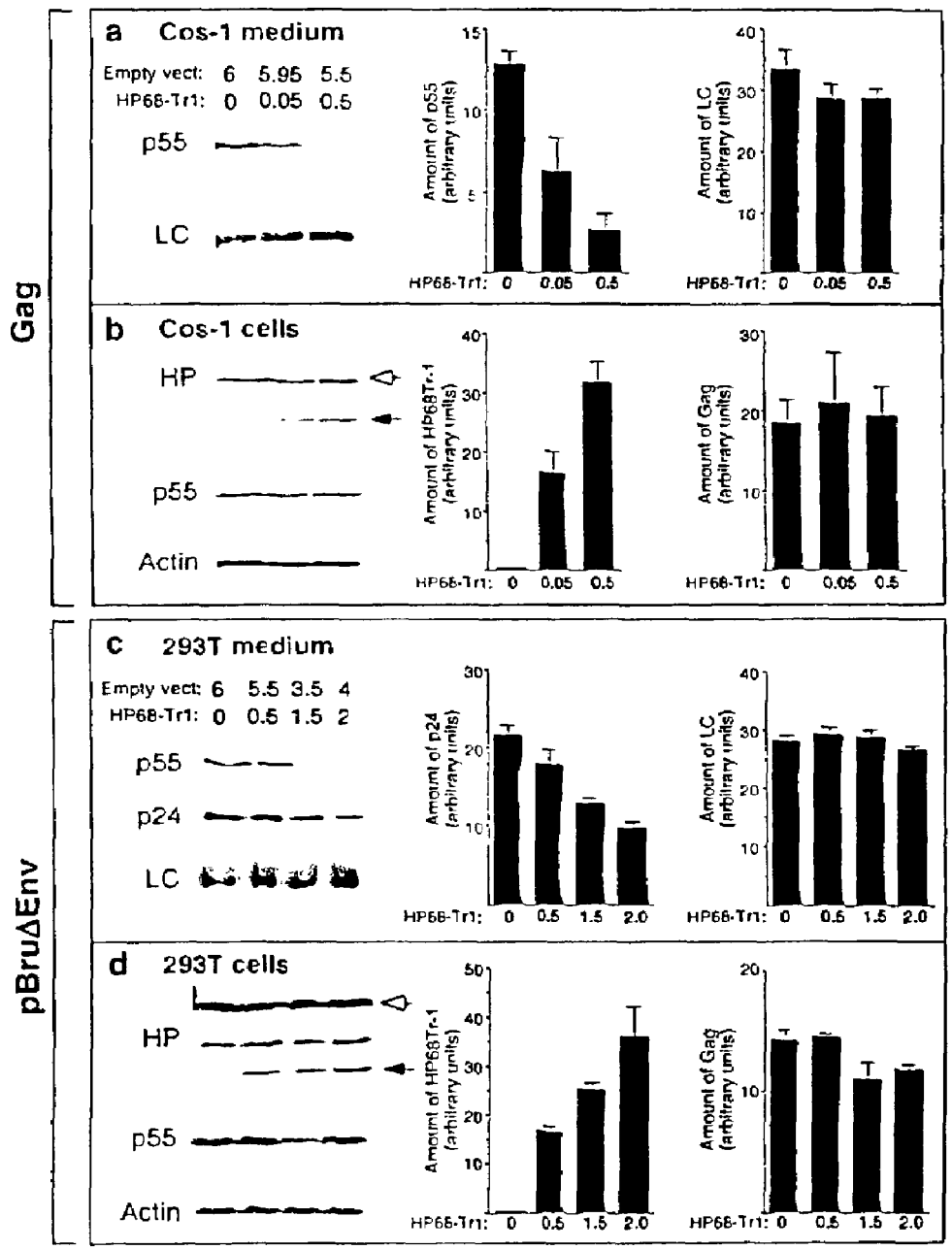
FIG. 13 shows truncated HP68 blocks virion production.

All plasmid constructions for cell-free transcription were made using polymerase chain reactions (PCR) and other standard nucleic acid techniques (Sambrook, J., et al., in Molecular Cloning. A Laboratory Manual). Plasmid vectors were derived from SP64 (Promega) into which the 5' untranslated region of *Xenopus* globin had been inserted at the Hind III site (Melton, D. A., et al., *Nucleic Acids Res.* 12:7035-7056 (1984)). The gag open reading frame (ORF) from HIV genomic DNA (a kind gift of Jay Levy; University of California, San Francisco) was introduced downstream from the SP6 promoter and the globin untranslated region. The GΔA mutation was made by changing glycine at position 2 of Gag to alanine using PCR (Gottlinger, H. G., et al., *Proc. Natl. Acad. Sci.* 86:5781-5785 (1989)). The Pr46 mutant was made by introducing a stop codon after gly 435 (removes p6); Pr41 has a stop codon after arg 361 (in the C terminal region of p24). These truncation mutants are comparable to those described by Jowett, J. B. M., et al., *J. Gen. Virol.* 73:3079-3086 (1992), incorporated herein by reference. To make the D2 mutant amino acids from gly 250 to val 260 were deleted (as in Hockley, D. J. et al., *J. Gen. Virol.* 75:2985-2997 (1994); Zhao, Y., et al., *Virology* 199:403-408 (1994)). All changes engineered by PCR were verified by DNA sequencing. The plasmid, pBRUΔenv, which encodes for the entire HIV-1 genome except a deletion in envelope, was made and used as previously described (Kimpton et al. J. Virology (1992) 66:2232-9). The plasmid, WGHP68-Tr1, encodes a 379 amino acid truncated form of HP68 with a stop codon before the second nucleotide-binding domain (Arrow, FIG. 10). This plasmid encodes the N-terminal two-thirds of WGHP68 and produces the expected 43 kD protein when transfected into cells (FIG. 13)

3. 35-S Energy Mix

35-S Energy Mix (5× stock) contains 5 mM ATP (Boehringer Mannheim), 5 mM GTP (Boehringer Mannheim), 60 mM Creatine Phosphate (Boehringer Mannheim), 19 amino acid mix minus methionine (each amino acid except methionine; each is at 0.2 mM), 35-S methionine 1 mCurie (ICN) in a volume of 200 microliters at a pH of 7.6 with 2 M Tris base.

4. Compensating Buffer

The Compensating Buffer (10×) contains 40 mM HEPES-KOH, at a pH of 7.6 (U.S. Biochemicals), 1.2 M KAcetate (Sigma Chemical Co.), and 2 mM EDTA (Mallinckrodt Chemicals, Paris, Ky.).

Example 1

Cell Free Protein Synthesis

1. Transcription

The plasmid containing the Gag coding region was linearized at the EcoRl site (as described in the NEB catalogue). The linearized plasmid was purified by phenol-chloroform extraction (as described in Sambrook, J., et al., in Molecular Cloning. A Laboratory Manual) and this plasmid was adjusted to a DNA concentration of 2.0 mg/ml. Transcription was carried out using a reaction that contained: 40 mM Tris Ac (7.5), 6 mM Mg Ac, 2 mM Spermidine, 0.5 mM ATP, 0.5 mM CTP, 0.5 mM UTP, 0.1 mM GTP, 0.5 mM diguanosine triphosphate (cap), 10 mM Dithiothreitol, 0.2 mg/ml transfer RNA (Sigma Chemical Co.), 0.8 units/microliter RNAse inhibitor (Promega), 0.4 units per microliter of SP6 Polymerase (NEB). Mutant DNAs were prepared as described by Gottlinger, H. G., et al., *Proc. Natl. Acad. Sci.* 86:5781-5785 (1989); Jowett, J. B. M., et al., *J. Gen. Virol.* 73:3079-3086 (1992); Hockley, D. J. et al., *J. Gen. Virol.* 75:2985-2997

(1994); or Zhao, Y., et al., *Virology* 199:403-408 (1994); these publications are incorporated herein by reference.

2. Translation

Translation of the transcription products was carried out in wheat germ extract containing $^{35}$S methionine (ICN Pharmaceuticals, Costa Mesa, Calif.). The wheat germ extract was prepared as described by Erickson and Blobel (1983) as modified below. Reactions were performed as previously described (Lingappa, J. R., et al., J. Cell. Biol. (1984) 125: 99-111), except for modifications noted below.

A 25 microliter wheat germ transcription/translation reaction mixture contained: 5 microliters Gag transcript (prepared as described in transcription methods), 5 microliters wheat germ extract (prepared as described in wheat germ preparation; preferably using the high speed supernatant detailed in Example 4), 5 microliters 35-S Energy Mix 5× stock (Sigma Chemical Co., St. Louis, Mo.), 2.5 microliters Compensating Buffer (Sigma Chemical Co.), 1.0 microliter 40 mM MgAcetate (Sigma Chemical Co.), 2.0 microliters 125 5M Myristoyl CoA (made up in 20 mM Tris Acetate, pH 7.6; Sigma Chemical Co.), 3.75 microliters 20 mM Tris Acetate buffer, p11 7.6 (U.S. Biochemicals; Cleveland, Ohio), 0.25 microliter Creatine Kinase (4 mg/ml stock in 50% glycerol, 10 mM Tris Acetate; Boehringer Mannheim, Indianapolis, Ind.), 0.25 microliter bovine tRNA (10 mg/ml stock; Sigma Chemical Co.), and 0.25 microliter RNAse Inhibitor (20 units/50; Promega).

3. Preparation of Wheat Germ Extract

Wheat germ was obtained from General Mills. Wheat germ extract was prepared as described by Erickson and Blobel (1983) with indicated modifications. Three grams of wheat germ were placed in a mortar and ground in 10 ml homogenization buffer (100 mM K-acetate, 1 mM Mg-acetate, 2 mM $CaCl_2$, 40 mM HEPES buffer, pH 7.5 (Sigma Chemicals, St. Louis, Mo.), 4 mM dithiothreitol) to a thick paste. The homogenate was scraped into a chilled centrifuge tube and centrifuged at 4° C. for 10 min at 23,000×g. The resulting supernatant was centrifuged again under these conditions to provide an S23 wheat germ extract.

Improved assembly was obtained when the S23 wheat germ extract was further subjected to ultracentrifugation at 50,000 rpm in the TLA 100 rotor (100,000×g) (Beckman Instruments, Palo Alto, Calif.) for 15 min at 4° C. and the supernatant used for in vitro translation. This improvement provided 2-3× the yield obtained in comparable reactions using the S 23 wheat germ extract. This supernatant is referred to herein as a "high speed wheat germ extract supernatant". It is appreciated that extracts of other eukaryotic cells, such as rabbit reticulocytes may be used to form analogous high-speed supernatants, and that such supernatants will be useful in practicing the present invention.

Myristoyl coenzyme A (MCoA; Sigma, St. Louis, Mo.) was added at a concentration of 10 micromolar at the start of translation when indicated. Translation reactions ranged in volume from 20 to 100 microliters and were incubated at 25° C. for 150 min. Some reactions were adjusted to a final concentration of the following agents at tunes indicated in the figures and specification: 0.2 µM emetine (Sigma); 1.0 units apyrase (Sigma) per mL translation; 0.002%, 0.1%, or 1.0% "NIKKOL". Cell-free translation and assembly reactions were also carried out successfully in rabbit reticulocyte lysate prepared as described previously (Merrick, W. C., *Methods Enzymol.* 101:606-615 (1983)) or obtained from commercial suppliers (Promega, Madison, Wis.). In pulse-chase experiments, translation reactions contained $^{35}$S cysteine (Amersham Life Sciences, Cleveland, Ohio) for radiolabeling. After 4 min translation reaction time, 3 mM unlabeled cysteine was added, and the reaction was continued at 25° C. for variable chase times as indicated in the experiments described herein.

4. Estimation of Sedimentation Coefficients

Estimates of S-values of Gag-containing complexes seen on 13 ml sucrose gradients were determined by the method of McEwen, C. R., *Anal. Biochem.* 20:114-149 (1967) using the following formula:

$$S = \Delta I / \omega^2 t$$

where S is the sedimentation coefficient of the particle in Svedberg units, $\Delta I$ is the time integral for sucrose at the separated zone minus the time integral for sucrose at the meniscus of the gradient, $\omega$ is rotor speed in radians/sec. and t is time in sec.

Values for I were determined for particles of a density of 1.3 g/cm3 and for a temperature of 5° C., according to tables published by McEwen, C. R., *Anal. Biochem.* 20:114-149 (1967). Calculated S values for different fractions in the gradients are labeled as markers above each gradient tracing shown herein. Markers such as BSA (5-S), macroglobulin (20-S), Hepatitis B Virus capsids (100-S), ribosomal subunits (40-S and 60-S), and polysomes (>100-S) were used to calibrate the gradients and to confirm the calculated S values. However, it should be noted that the S value assignments for each Gag-containing complex are approximate estimates and may vary by about ±10%.

Example 2

Preparation of HSS, HSP, and HSPd

Where indicated, wheat germ extract prepared as described in Example 1 was centrifuged at either 50,000 rpm for 21 min or 100,000 rpm for 30 min in a TLA 100 rotor (Beckman Instruments, Palo Alto, Calif.). The supernatant (high-speed supernatant, HSS) of the 50,000 rpm spin was used for cell-free translation and assembly reactions. The pellet of the 100,000 rpm spin (high speed pellet, HSP) was resuspended at a 5× concentration in buffer (25 mM Hepes pH 7.4, 4 mM MgAc, 100 mM KAc, 0.25M sucrose). Wheat germ extract adjusted to contain a concentration 0.5% "NIKKOL" was subjected to the same ultracentrifugation in parallel to generate the detergent treated high-speed pellet (HSPd). This pellet was washed twice with 200 RL of the above non-detergent buffer in order to remove traces of detergent, and then resuspended as described above. Following treatment with emetine at 50 mm, 1.8 µL of HSP or HSPd was added to the 18 mL cell-free reactions programmed with HSS. Control reactions were treated with the same volume of buffer at the same time. At the end of the 150 min incubation, reactions were separated into soluble and particulate fractions and analyzed as described above.

Example 3

Translation of Gag Pr55 Protein in a Cell Free System

Figure 2A:
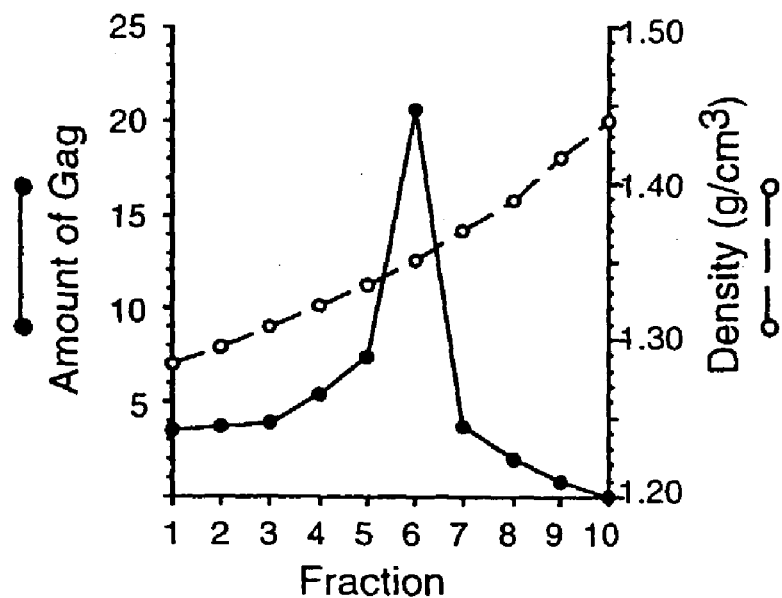
FIG. 2 shows migration of capsids formed in a cell free system (FIG. 2A) and in a cellular system (FIG. 2B) on velocity sedimentation gradients, in the form of plots of the buoyant density of each of the sequential fractions collected, assessed by refractive index (open circles), and of the amount of Gag protein in each fraction, as assessed by densitometry (closed circles).
Figure 2B:
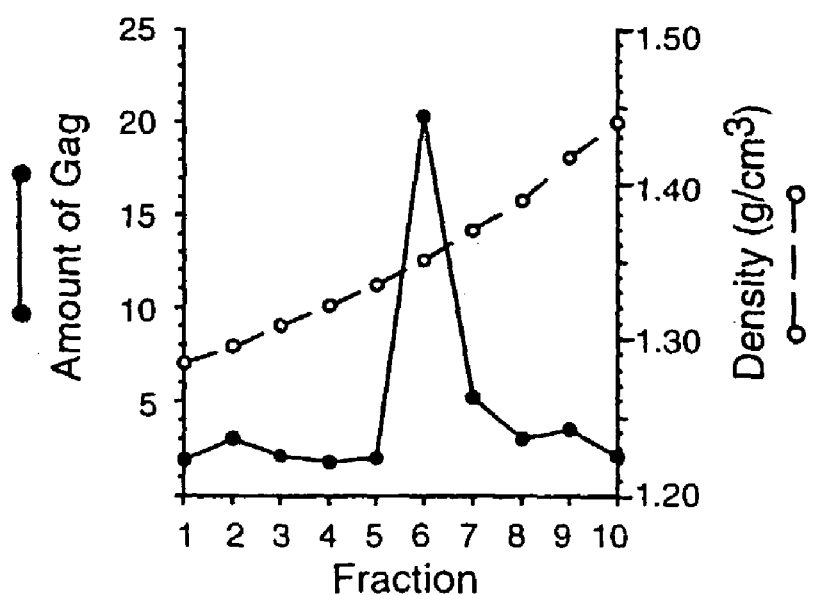

The cell-free translation/assembly system of the invention contains the components described in Part A, above. Example 1 provides details of an exemplary system derived from wheatgerm extract, which is capable of supporting translation and assembly of HIV capsids. Briefly, protein synthesis was initiated in the cell-free translation/assembly system by adding an mRNA that encodes Gag Pr55 protein. Alternatively, when the system includes transcription means, such as SP6 or T7 polymerase, the reaction may be initiated by addition of DNA encoding the protein. Complete synthesis of protein and assembly into capsids is usually achieved within about 150 minutes. FIG. 2 shows that capsids formed in the cell-free system of the invention are substantially the same as those formed in cells. Shown in the Figure is a comparison of migration of the capsids through an isopycnic CsCl gradient, where capsids formed in the cell-free translation/assembly system are shown in FIG. 2A, and capsids formed in transfected Cos cells are shown in FIG. 2B. Cell-free translation and assembly reactions containing 10 µM MCoA and $^{35}$S methionine were programmed with HIV Gag transcript and incubated under the conditions detailed in Example 1. At the end of the reaction, samples were diluted into buffer containing 1% NP40 (a non-ionic detergent), and separated into soluble and particulate fractions on sucrose step gradients, according to standard methods known in the art employing sucrose step or linear gradients as appropriate. The particulate fraction was collected and analyzed by velocity sedimentation on a 13-ml 15-60% linear sucrose gradient (Beckman SW40 Ti rotor, 35,000 rpm, 75-90 min). Fractions from the gradient were collected and subjected to sodium lauryl sulfate polyacrylamide gel electrophoresis (SDS-PAGE) analysis according to standard methods.

A parallel analysis of the particulate fraction was performed by subjecting the particulate fraction to CsCl gradient separation (2 ml isopycnic CsCl, 402.6 mg/ml; 50,000 rpm in a Beckman TLA 100 centrifuge) according to standard methods. Fractions were collected and assessed for Gag translation product (Pr55) (top of gradient is fraction 1, open circles, FIG. 2B). The fractions containing radiolabeled Pr55 were also subjected to SDS PAGE analysis; Gag content of the various fractions was estimated by scanning densitometry of autoradiographs made from the gels. Both conditions produced identical radiolabeled protein bands under these conditions. Material in the particulate fraction (>500-S) was further analyzed by a variety of methods as described below.

Translation of the HIV Gag transcript encoding Pr55 in the cell-free system resulted in the synthesis of approximately 2 ng Pr55 protein per microliter translation reaction. It is appreciated that increased production might be achieved, for example, by employing a continuous flow translation system (Spirin, A. S., et al., *Science* 242: 1162-1164 (1988)) augmented with the specific factors and components described above.

Example 4

Transfections and Production of Authentic Capsids

Cos-1 cells (University of California Cell Culture Facility) were transfected by the adenovirus-based method (Forsayeth, J. R. and Garcia, P. D., *Biotechniques* 17:354-358 (1994)), using plasmids pSVGagRRE-R (a mammalian expression vector that encodes Gag as well as the Rev response element required for expression of Gag in mammalian cells) and pSVRev (a mammalian expression vector that encodes the Rev gene, the product of which is required for expression of Gag in mammalian cells) (Smith, A. J., et al., *J. Virol.* 67:2266-2275 (1993)). These vectors were provided by D. Rekosh (University of Virginia). Cells were also transfected with pBRUΔenv, FIG. 15. Four days after transfection, immature HIV particles were purified from the culture medium by sedimentation through a 4 ml 20% sucrose cushion in an SW 40 rotor at 29,000 rpm for 120 min (Mergener, K., et al., *Virology* 186:25-39 (1992)). The pellet was harvested, stored in aliquots at −80° C., and treated with 1% NP40 buffer just before use to remove envelopes. These de-enveloped authentic immature HIV capsids were used as standards and analyzed in parallel with the products of cell-free reactions by a variety of methods, including velocity sedimentation, equilibrium centrifugation, and electron microscopy.

Detergent-treated capsids generated in the cell-free system and detergent-treated (de-enveloped) authentic capsids behaved as a relatively homogenous population of particles of approximately 750-S (compare FIGS. 2A and 2B), with a buoyant density of 1.36 g·cm-3. Additionally, cell-free-assembled capsids and the authentic standard were identical in size as judged by gel filtration. Electron microscopic analysis revealed that capsids made in the cell-free system were morphologically similar to authentic capsids released from transfected cells and had the expected diameter of approximately 100 nm (Gelderblom, H. R., *AIDS* 5:617-638 (1991)). Thus, radiolabeled Pr55 protein synthesized in the cell-free system assembles into particles that closely resemble authentic immature HIV capsids generated in transfected cells, as judged by EM appearance as well as the biochemical criteria of size, sedimentation coefficient, and buoyant density.

A lysate of transfected Cos cells was prepared by solubilizing transfected cells on 60 mm plates in 700 µL 1% NP40 buffer. This detergent lysate was passaged 20 times through a 20-gauge needle, clarified by centrifugation for 10 min at 2000×g, and 150 mL of this supernatant was loaded onto 13 ml sucrose gradients for analysis as described in Example 2. Gag polypeptide present in the fractions was visualized by immunoblotting with a monoclonal antibody to Gag (Dako, Carpenteria, Calif.). Bound antibody was detected using an enhanced chemiluminescence system (Amersham). Band density was determined as described under image analysis below, and relative band densities were confirmed by quantitating films representing different exposure times.

Example 5

Immunoprecipitation of Capsid Assembly Intermediates

Immunoprecipitation under native conditions was performed by diluting 2 µL samples of cell-free reactions into 30 µL of 1% NP40 buffer, and adding approximately 1.0 µg of one of monoclonal antibody 23 c (Institute for Cancer Research, London, UK; Stressgen, Vancouver, BC). Samples containing antibodies were incubated for one hour on ice, a 50% slurry of Protein G beads (Pierce, Rockford, Ill.) or Protein A Affigel (BioRad, Richmond, Calif.) was added, and incubations with constant mixing were performed for one hour at 4° C. Beads were washed twice in 1% NP 40 buffer containing 0.1 M Tris, pH 8.0, and then twice in wash buffer (0.1 M NaCl, 0.1 M Tris, pH 8.0, 4 mM MgAc). Proteins were eluted from the beads by boiling in 20 µL SDS sample buffer and were visualized by SDS-PAGE and autoradiography, according to methods well known in the art.

Example 6

Requirements of Capsid Assembly

1. Myristoylation of Pr55

Figure 3A:
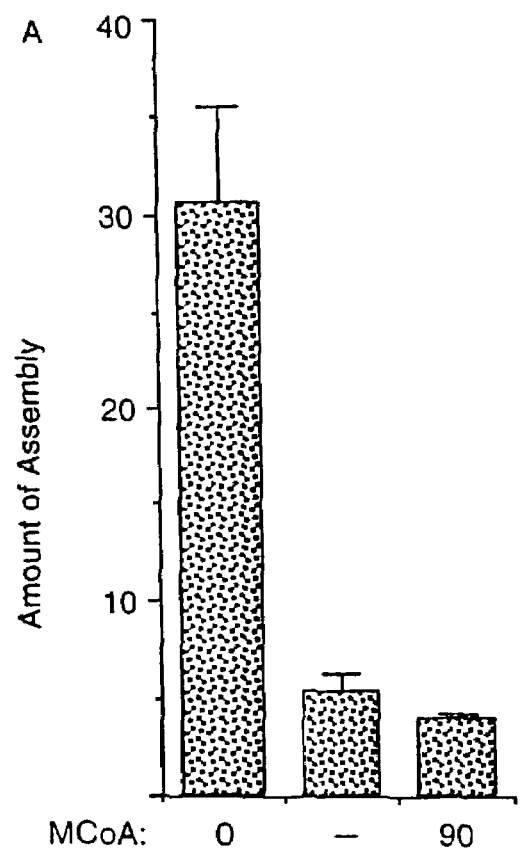
FIG. 3 shows the amount of capsid assembly occurring in a cell free system in the presence of MCoA added at different time points during the reaction (FIG. 3A) and in the presence of two different concentrations of "NIKKOL" (FIG. 3B).
Figure 3B:
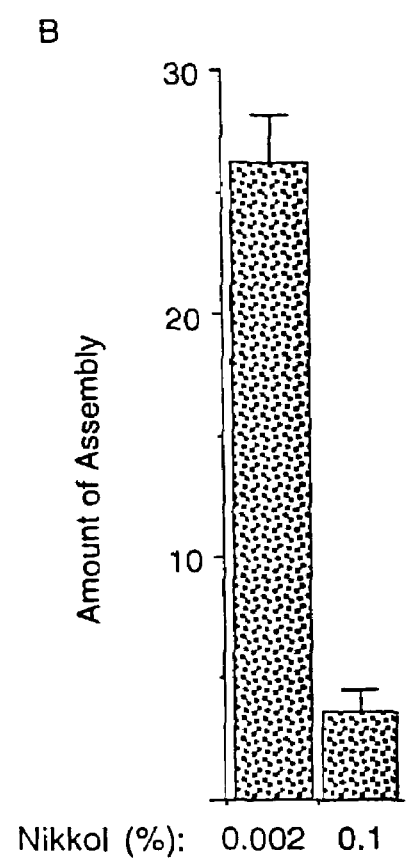

FIGS. 3A and 3B show the results of experiments carried out in support of the present invention in which the cell-free translation/assembly reaction was run in the absence or presence of certain components. FIG. 3A shows the effects of addition of myristoyl coenzyme A (MCoA) to a cell-free translation and assembly reaction programmed with Gag transcript. As shown, the reaction was run in the absence of added MCoA ("–") or with 10 µM MCoA added either at the start of the reaction ("0") or at 90 minutes into the reaction when translation is completed ("90"). The detergent-treated products of the cell-free reactions were separated into soluble and particulate fractions by centrifugation on step gradients, and radiolabeled protein in each fraction was visualized by SDS-PAGE and AR as described above. The amount of radiolabeled Pr55 in the particulate fraction (which contains assembled capsids) was determined by densitometry of bands and is expressed as percent of total Gag protein synthesized. The presence of MCoA had no effect on the total amount of Pr55 synthesized; however, it did affect the amount of assembly into capsids, as shown. In the absence of MCoA, or when MCoA was not added until late in the reaction at a post-translational phase (90 min), very little assembly occurred. Values shown are the average of 3 independent experiments, and error bars indicate standard error.

Without ascribing to any particular underlying mechanistic theory, the foregoing results suggest that capsid assembly in the cell-free system requires co-translational myristoylation. This is consistent with an N-terminal modification of the protein which may be required for interaction of the assembly proteins with the inner aspect of a plasma membrane fraction that is required for assembly (Gheysen, D. et al., *Cell* 59:103-112 (1989); Bryant and Ratner, 1990; Wang, C.-T. and Barklis, E., *J. Virol.* 67:4264-4273 (1993); Platt, E. J. and Haffar, O. K., *Proc. Natl. Acad. Sci.* 91:4594-4598 (1994); Spearman, P. et al., *J. Virol.* 68:3232-3242 (1994); Hockley, D. J. et al., *J. Gen. Virol.* 75:2985-2997 (1994); Bryant and Ratner, 1990; Jacobs E., et al., *Gene* 79:71-81 (1989). Consistent with these data, in experiments carried out in support of the present invention, a Gag mutant that fails to become myristoylated (GΔA) is also incapable of assembly in the cell-free system (see FIG. 3B).

2. Detergent-Sensitive Component

Studies carried out in support of the present invention have revealed that another critical component of the HIV capsid formation is sensitive to detergent concentrations above the critical micelle concentration (cmc). Membrane fragments are present in the exemplary wheat germ extracts used in experiments described herein, as evidenced by sensitivity of the reaction to addition of detergent at concentrations that solubilize membranes.

Solubilization of membranes can be effected by addition of the detergent "NIKKOL" (octaethyleneglycol mono n-dodecyl ether; Nikko Chemical Co., Tokyo, Japan) at a concentration of 0.1%. At this concentration, "NIKKOL", a relatively gentle non-ionic detergent, had no effect on Gag polypeptide synthesis. However, as shown in FIG. 3B, "NIKKOL" at this concentration largely abolished capsid assembly. In the experiments shown, cell free translation and assembly reactions containing 10 µM MCoA were programmed with Gag transcript. "NIKKOL" was added at the start the translation reaction to a final concentration of 0.002 or 0.1%, as indicated. At the end of the incubation, the reactions were analyzed for amount of assembly as described above in relation to FIG. 3A. Values shown are the average of 3 independent experiments, and error bars indicate standard error. This effect was not observed when "NIKKOL" was used at a concentration of 0.002%, which is below that required to disrupt lipid bilayers (Walter, P. and Blobel, G., *Proc. Natl. Acad. Sci. USA* 77:7112-7116(1980)).

In further experiments carried out in support of the invention, it was found that "NIKKOL" added after the completion of the 150 min. assembly reaction did not diminish the amount of assembly, even when added to a concentration of 1.0%. Thus, it appears that whereas the integrity of the completed capsid shell is not sensitive to "NIKKOL" (even at high concentrations), assembly of this structure is inhibited by concentrations of "NIKKOL" that are sufficient to solubilize membranes. Further, as described in more detail below, when the Pr55 translation/assembly reaction was treated with emetine and 0.1% "NIKKOL" during a post-translational phase 50 min into the reaction, assembly was dramatically reduced.

The foregoing data are consistent with the idea that membranes are required for newly-synthesized and myristoylated Pr55 chains to be assembled efficiently into capsids in the cell-free system.

3. Incubation Conditions

In experiments carried out in support of the present invention, it was found that optimum assembly in the cell-free system requires incubation at 25° C. for at least 150 min, though it is appreciated that these conditions can be varied somewhat while still obtaining translation and assembly. Most Pr55 synthesis occurs during the first hour of this incubation; significant capsid formation does not take place until the final 90 min of the reaction. Thus, an aliquot of the reaction incubated for only 50 min contains approximately 60% of the full-length Pr55 chains that are present in an aliquot incubated for the standard 150 min. However, essentially none of the chains present at the 50 min time point have assembled into caps ids, while at 150 min 25% have completed the assembly process (see FIG. 4A).

Based on these observations, it was possible to separate the translation and assembly phases of the reaction. To confirm this, a reaction mixture was split into two aliquots after 50 min incubation time. To one aliquot emetine was added. (Emetine blocks translation by inhibiting chain elongation.) Both aliquots were incubated to the 150 min time point. While total Pr55 synthesis in the emetine-treated reaction was 60% of the control, the proportion of capsid assembly in this treated reaction was comparable to that of the untreated control (FIG. 4A, bar graph), indicating that assembly takes place even when translation is halted. These data provide basis for dividing the reaction into two phases, where manipulations performed after emetine treatment are observed to have effects on only the post-translational phase of assembly and should not affect Pr55 synthesis, which is already completed.

4. Energy Requirement

According to an important aspect of the invention, assembly of capsids is dependent upon the presence of an energy source in the reaction mixture. An exemplary energy source is the creatine phosphate-creatine phosphokinase system, which regenerates ATP. Equivalent energy sources will be known to those skilled in the art. In experiments carried out in support of the invention, cell-free translation and assembly reactions were programmed with Pr55 in the presence of 10 µM MCoA. Gag translation was allowed to proceed for 50 min, at which point further protein synthesis was inhibited by addition of 0.2 µM emetine. Immediately after emetine treatment, apyrase, an enzyme that hydrolyzes ATP, was added at a concentration of 1 unit/microliter to one of the emetine-treated reactions. At the end of the incubation (150 min), 1 µl of each reaction was analyzed directly by SDS PAGE (autoradiographs are shown below bar graph). The remainder of the products were analyzed for amount of assembly as described above. Shown in the bar graph is the amount of Pr55 assembled as a percent of total Pr55 synthesized in each reaction. Values in the bar graph are the average of 3 independent experiments, and error bars indicate the standard error.

Figure 4A:
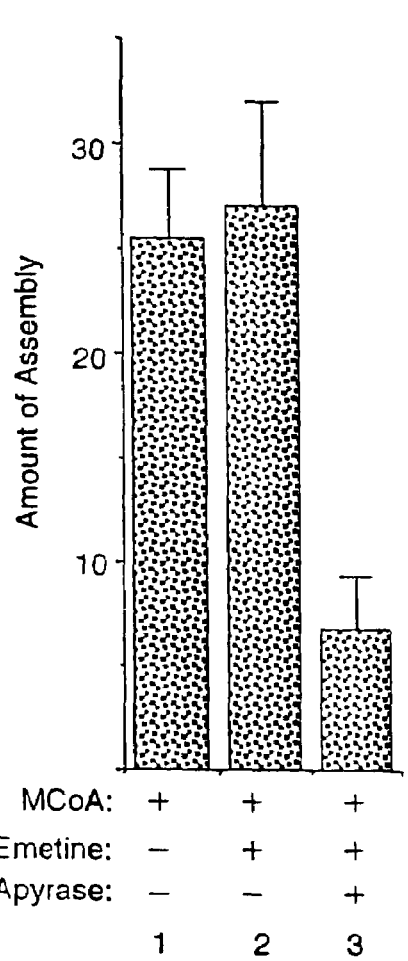
FIG. 4 shows bar graphs demonstrating the effect on assembly of inhibition of protein synthesis and depletion of ATP fifty minutes into the reaction (FIG. 4A) and the requirement for a membrane fraction in the reaction (FIG. 4B)

Depletion of free ATP from the assembly reaction by apyrase treatment resulted in a dramatic reduction in capsid assembly (FIG. 4A, bar graph). The effect of ATP depletion was not reversed by addition of the non-hydrolyzable analogue AMP-PNP after apyrase treatment, suggesting that ATP hydrolysis, and not just ATP binding, is required. Addition of apyrase did not change the total amount of Pr55 synthesis, as assessed by measurement of amount of protein by SDS-PAGE analysis, confirming that the effect was on capsid assembly rather than on protein translation. Furthermore, adding apyrase to the reaction after capsid assembly was completed had no effect on the amount of assembly, indicating that the ATP depletion did not affect capsid stability. These data indicate that there is a requirement for an energy source such as ATP in the capsid assembly process, and that this ATP dependence is distinct from the energy requirements of protein synthesis.

5. Detergent-Insensitive Subcellular Component

According to another feature of the invention, it was found that reconstitution of the reaction mixture with a subcellular fraction promotes assembly. As described below this component is distinguished by its relative insensitivity to detergent. Specifically, it is not inactivated by exposure to 0.5% "NIKKOL".

Wheat germ extract was subjected to ultracentrifugation as described in Example 2 to generate the high-speed supernatant (HSS, depleted of components having sedimentation velocities of 90S or greater), high-speed pellet (HSP), and detergent-treated high speed pellet (HSPd). The HSS was used to program cell-free translation and assembly reactions in the presence or absence of 10 µM MCoA (as indicated in FIG. 5B). Each of these reactions was treated with the protein synthesis inhibitor emetine at 50 min. Following this, the HSP or HSPd was added to aliquots of the reaction as indicated below the bar graph in FIG. 4B. All reactions were incubated for a total of 150 min. A one microliter aliquot was removed and analyzed directly by SDS PAGE (shown below bar graph in FIG. 4B). The remainder of each reaction was analyzed for amount of assembly as described above and plotted as percent of total Pr55 present in each reaction. The values shown in the bar graph are the average of 3 independent experiments, and error bars indicate the standard error.

Figure 4B:
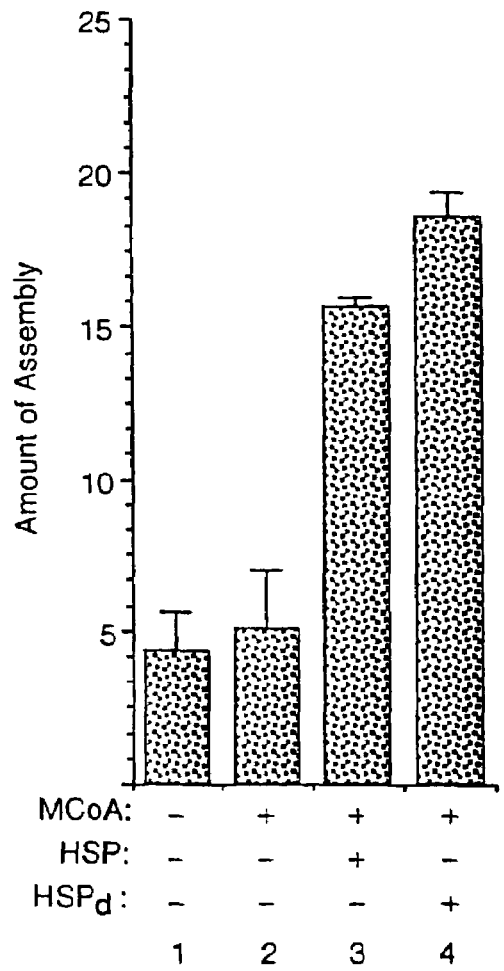

These experiments showed that the HSS, depleted of components that were 90-S or greater, supported Pr55 translation but not its assembly (FIG. 4B). This indicates that the HSP likely contains assembly-specific host factor(s). This was demonstrated directly by showing that addition of the HSP post-translationally (following emetine treatment) to unassembled Gag chains synthesized in the HSS resulted in a considerable restoration of particle assembly (FIG. 4B). In these experiments, total synthesis of Pr55 was unaltered by addition of the HSP. Together, these data indicate that a subcellular fraction of the eukaryotic cell lysate is required for post-translational events in capsid assembly to take place. That this component is distinct from the plasma membrane component described above is evidenced by the experiments described below indicating that, unlike the plasma membrane component, this component is not sensitive to treatment with a non-ionic detergent.

HSP was examined for the presence of a detergent-sensitive component that is required for capsid formation. HSP was prepared from a cell extract treated with detergent (0.5% "NIKKOL"). The resulting HSP ("HSP$_d$") was washed with detergent-free buffer, and was added post-translationally to an assembly reaction. As shown in FIG. 4B, HSP from the detergent-treated extract was equally as active in promoting post-translational capsid formation as the control HSP (FIG. 4B, bar graph). Thus, separate detergent-sensitive and detergent-insensitive host factors appear to be involved in the post-translational phase of HIV capsid assembly. Furthermore, the detergent-insensitive host factor can be depleted by ultracentrifugation and then reconstituted by post-translational addition. According to a further feature of the invention it is appreciated that the detergent-insensitive subcellular component can be further fractionated and characterized.

Example 7

HIV Mutant Capsid Formation

Studies of capsid assembly in cultured cells have revealed that certain mutations within the Gag coding region disrupt immature HIV capsid assembly. Four previously-described mutations in Gag are diagrammed in FIG. 5A: (i) the Pr46 mutant, in which the C terminal p6 domain of Gag is deleted (Jowett, J. B. M., et al., *J. Gen. Virol.* 73:3079-3086 (1992); Spearman, P. et al., *J. Virol.* 68:3232-3242 (1994); Royer, M., et al., *Virology* 184:417-422 (1991); Hockley, D. J. et al., *J. Gen. Virol.* 75:2985-2997 (1994); (ii) the Pr41 mutant, in which the deleted domains include p6, the entire nucleocapsid region (p7), and the distal end of p24 containing the p24-p7 protease cleavage site (Gheysen, D. et al., *Cell* 59:103-112 (1989); Jowett, J. B. M., et al., *J. Gen. Virol.* 73:3079-3086 (1992); Hockley, D. J. et al., *J. Gen. Virol.* 75:2985-2997 (1994); (iii) the D2 mutation, in which 10 amino acids of the p24 domain of Gag (upstream of the p24-p7 protease cleavage site) are Zhao, Y., et al., *Virology* 199:403-408 (1994); Hockley, D. J. et al., *J. Gen. Virol.* 75:2985-2997 (1994); and (iv) the GΔA mutation, an N-terminal single amino-acid substitution that abolishes myristoylation of Gag (Gottlinger, H. G., et al., *Proc. Natl. Acad. Sci.* 86:5781-5785 (1989); Bryant and Ratner, 1990). Upon expression in cells, only the Pr46 mutant was capable of producing viral particles indistinguishable from those produced by expression of wild-type Gag (Jowett, J. B. M., et al., *J. Gen. Virol.* 73:3079-3086 (1992); Spearman, P. et al., *J. Virol.* 68:3232-3242 (1994); Royer, M., et al., *Virology* 184: 417-422 (1991); Hockley, D. J. et al., *J. Gen. Virol.* 75:2985-2997 (1994). Expressions of each of the other three mutations fails to result in efficient viral particle production and release (Gheysen, D. et al., Cell 59:103-112 (1989); Jowett, J. B. M., et al., *J. Gen. Virol.* 73:3079-3086 (1992); Hockley, D. J. et al., *J. Gen. Virol.* 75:2985-2997 (1994); Zhao, Y., et al., *Virology* 199:403-408 (1994); Gottlinger, H. G., et al., *Proc. Natl. Acad. Sci.* 86:5781-5785 (1989); Bryant and Ratner, 1990).

Figure 5A:
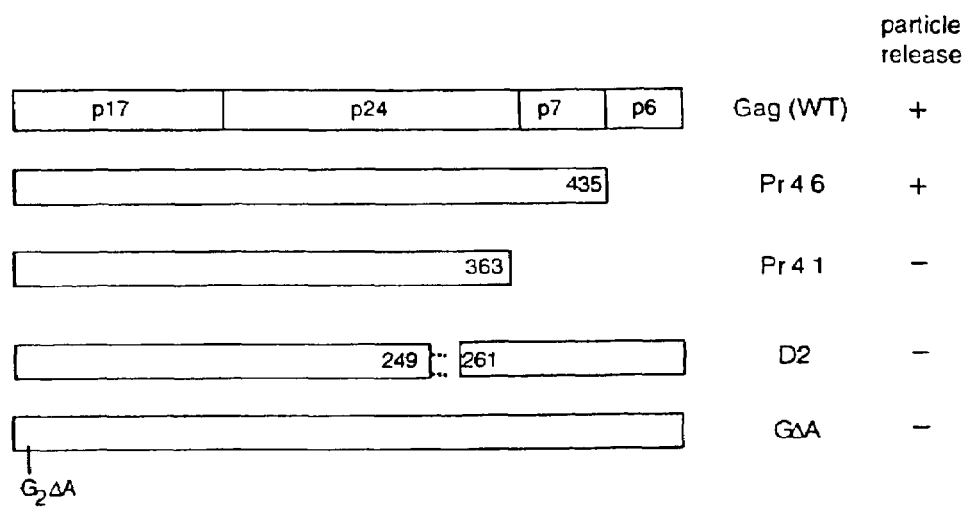
FIG. 5 shows schematic diagrams of mutations within Gag (FIG. 5A), and the amount (FIG. 5B) of capsid assembly that occurred in the cell-free system primed with transcripts of the various mutant HIV viruses shown in FIG. 5A, as well as wild-type capsids (WT) and capsids produced in the absence of MCoA (−MCoA).
Figure 5B:
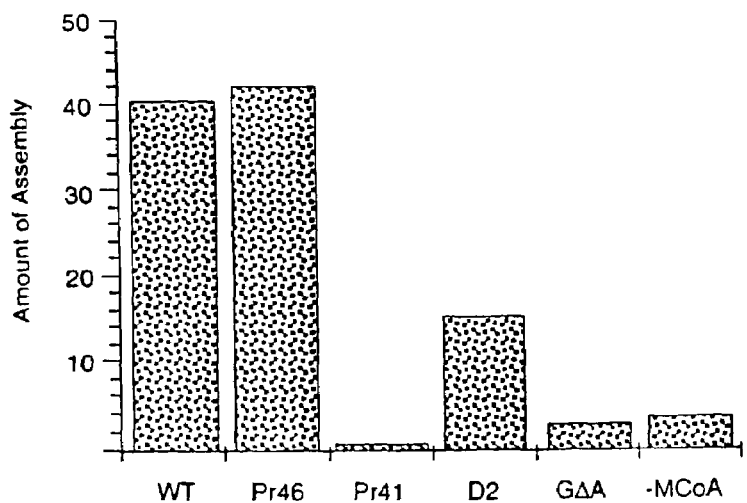

FIG. 5A shows schematically the Gag polyprotein precursor that consists of four domains, referred to as p 17, p 24, p7, and p6, and the mutants discussed above. The Pr46 and Pr41 mutants were constructed by introducing a stop codon truncation at amino acid 435 or at amino acid 363, respectively. In the D2 mutation, amino acids 249 to 261 are deleted. In the GΔA mutation, the glycine at amino acid 2 is substituted with an alanine, thereby blocking myristoylation. The known phenotypes with respect to particle release from cells expressing each of these mutants is indicated to the right (for references, see text).

FIG. 5B shows capsid assembly in cell-free reactions programmed with Gag mutants. Cell-free translation and assembly reactions were programmed with transcript coding for each of the Gag mutants described above, as well as transcript coding for wild-type Gag in the presence or absence of MCoA (labeled WT and -MCoA, respectively). At the end of the reaction period, each sample was detergent treated, fractionated on velocity sedimentation on 13 ml sucrose gradients, and analyzed by SDS-PAGE and autoradiography. The amount of radiolabeled translation product in the position of completed 750S capsids was quantitated by densitometry and expressed for each reaction as % of total synthesis. The total amount of translation was approximately equal in all reactions.

As is shown in FIG. 5B, the Pr41 and GΔA mutants failed to assemble completed capsids, while approximately 40% of the total translation product of both wild-type Gag and the assembly-competent Pr46 mutant assembled into completed capsids. The non-assembling D2 mutant appeared to have generated a small amount of material in the region of completed capsids, but further analysis of this material revealed it to be the trail of a large Gag complex (of approximately 400-500S) that does not comigrate with completed capsids (see FIG. 7E). Thus, like Pr41 and GDA, D2 did not assemble into the 750S completed capsid. Together, these data indicate that the cell-free system appears to reproduce phenotypes of a variety of assembly-defective and assembly-competent mutations in Gag.

Example 8

Identification of HIV Capsid Intermediates

The requirement for host factors and ATP suggests that discrete biochemical intermediates exist during the assembly process. Heretofore, such intermediates in HIV capsid assembly have not been described. However, according to a further aspect of the present invention, it is appreciated that the cell-free system of the present invention constitutes a good system for detecting assembly intermediates that would be otherwise difficult or impossible to detect.

Figure 6A:
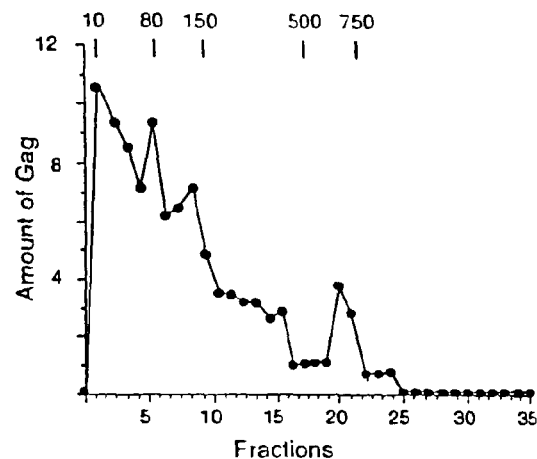
FIG. 6 shows pulse-chase analysis of HIV capsid assembly by velocity sedimentation in a continuously labeled cell-free reaction mixture (FIG. 6A) where the calculated positions of 10S, 80S, 150S, 500S, and 750S complexes are indicated by markers at the top of the graph, and in reactions to which unlabeled 35S cysteine was added 4 minutes into the reaction and aliquots were taken for sedimentation analysis after 25 minutes (FIG. 6B) and 15 minutes of reaction (FIG. 6C), and samples were further analyzed by SDS gel and radiography.

In experiments carried out in support of the present invention, a continuously labeled cell-free reaction was analyzed by velocity sedimentation. Cell-free translation and assembly of Pr55 was performed as described above. Upon completion of the cell-free reaction, the products were diluted into 1% NP40 sample buffer on ice, and were analyzed by velocity sedimentation on 13 ml 15-60% sucrose gradients. Fractions were collected from the top of each gradient, and the amount of radiolabeled Pr55 protein in each fraction was determined and expressed as percent of total Pr55 protein present in the reaction. The calculated positions of 10S, 80S, 150S, 500S, and 750S complexes are indicated with markers above the figures (cf., FIG. 6A). 750S represents the position of authentic immature (de-enveloped) HIV capsids. The intermediate complexes having calculated sedimentation coefficients of 10S, 80S, 150S and 500S are referred to herein as intermediates A, B, C and D, respectively.

Figure 6B:
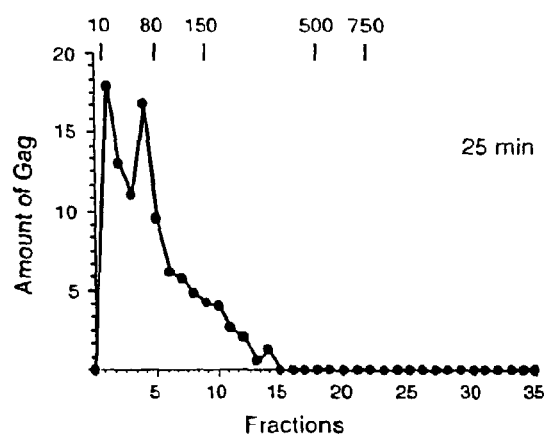
Figure 6:
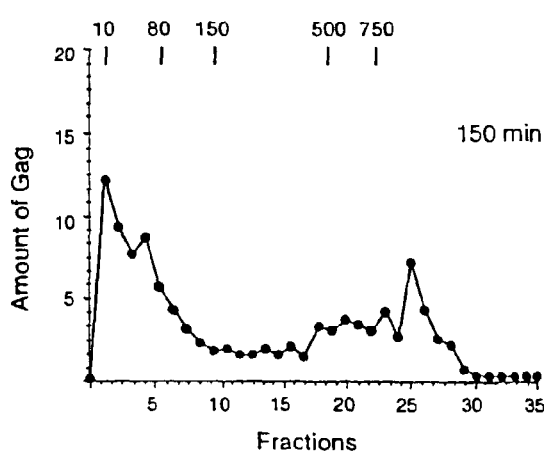
Figure 8A:
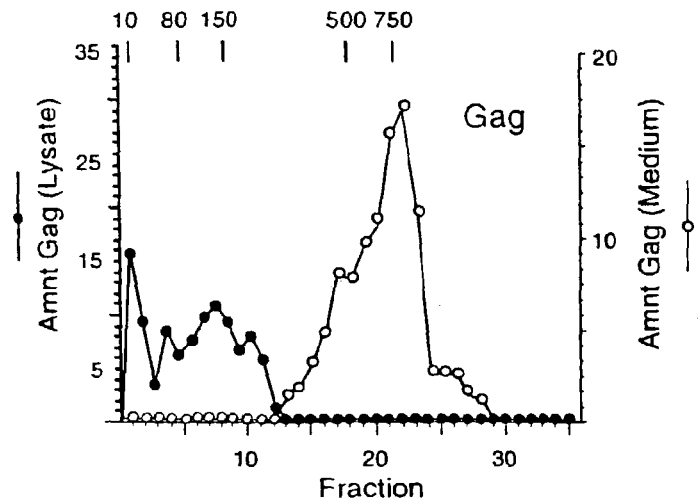
FIG. 8 shows plots of sedimentation of Gag complexes isolated from COS-1 cells transfected with a transfection vector encoding Pr55 cDNA wild-type Gag (FIG. 8A) or by transfection vectors encoding the p41 mutant (FIG. 8B) or the D2 mutant (FIG. 8C).
Figure 8B:
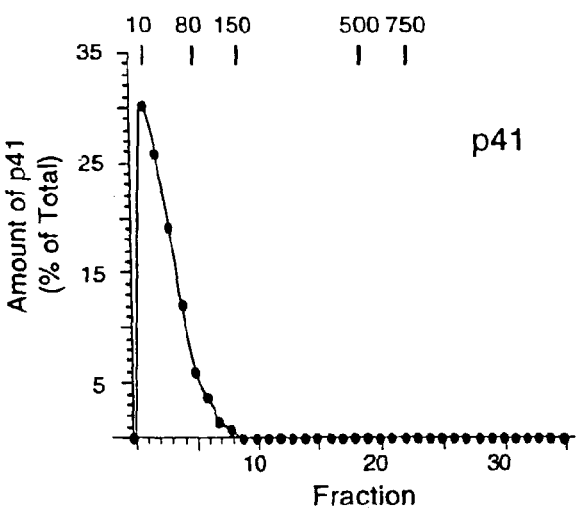
Figure 8C:
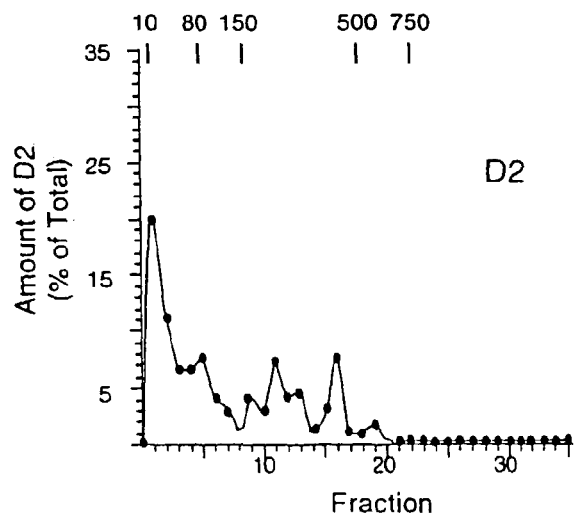

Further experiments in support of the present invention indicate that the identified intermediates represent assembly intermediates, as evidenced by the observation that they are present in large quantities at early time points, and are diminished at later times during the reaction. Specifically, pulse-chase analysis was used to follow a small cohort of radiolabeled Pr55 chains over time during the assembly reaction. Cell-free translation and assembly of Pr55 was performed according to the methods set forth in Example 1, except that $^{35}$S cysteine was used for radiolabeling. At 4 min into the translation reaction, an excess of unlabeled cysteine was added to the reaction so that no further radiolabeling would occur. Aliquots of the reaction were collected 25 min (FIG. 6B) and 150 min (FIG. 6C) into the reaction. One microliter of each aliquot was analyzed by SDS-PAGE and AR to reveal the total amount of radiolabeled Pr55 translation product (indicated by arrow in FIG. 6B) present at each chase time. The remainder of the aliquots were diluted into 1% NP40 sample buffer on ice, and were analyzed by velocity sedimentation on 13 ml 15-60% sucrose gradients (FIGS. 6B and 6C respectively), in the manner described for FIG. 6A above.

The total amount of radiolabeled Pr55 was the same at 25 min and 150 min into the pulse-chase reaction, indicating that neither further radiolabeling nor degradation of Pr55 chains occurred after 25 min, and confirming that the same population of Pr55 chains was being analyzed at both times.

After 25 minutes of reaction time, all of the radiolabeled Pr55 was found in complexes A, B, and C (FIG. 6B), with no radiolabeled Pr55 chains present in the region of completed 750S capsids. While complexes A and B appear as peaks at approximately the 10S and 80S positions of the gradient, complex C appears as a less distinct shoulder in approximately the 150S position. In marked contrast, examination of the assembly reaction at 150 minutes showed that a significant amount of radiolabeled Pr55 was assembled into completed capsids that migrated in the 750S position (FIG. 6C). Correspondingly, the amount of Pr55 in complexes A, B, and C was diminished by precisely the amount that was now found to be assembled, demonstrating that at least some of the material in complexes A, B, and C constitutes intermediates in the biogenesis of completed 750S capsids.

At extremely short chase times (i.e., 13 min), when only some of the radiolabeled chains have completed synthesis, full length Pr55 chains were found exclusively in complex A on 13 ml sucrose gradients, while nascent chains that are not yet completed were in the form of polysomes of greater than 100S. Thus, polysome-associated nascent chains of Gag constitute the starting material in this pathway, and the 10S complex A, which contains completed Gag chains, is likely to be the first intermediate in the formation of immature capsids. Therefore, complexes B and C may represent later assembly intermediates in the pathway of capsid formation.

As further confirmation that complexes A, B, and C constitute intermediates in HIV capsid assembly, it is shown below that blockade of assembly results in accumulation of Gag chains in the form of complexes with S values corresponding to the S values of A, B and C. Additional evidence is provided by data showing that blockade at different points along the pathway results in accumulation of complexes A, B, and C in various combinations, as determined by the order of their appearance during the course of assembly. For example, if an ordered pathway of intermediates exists, then blockade at early points in the pathway should result in accumulation of one or two Gag-containing complexes corresponding to early putative assembly intermediates, while blockade at a very late point in the pathway would result in accumulation of all the putative assembly intermediates but not the final completed capsid product.

a. Pharmacological Blockade of Assembly. Capsid assembly was disrupted by adding either apyrase post-translationally (as described in Section ll.C.4) or detergent cotranslationally (as described in Section II.C.2), and the reaction products were analyzed by velocity sedimentation. Material in fractions corresponding to the assembly intermediates and completed capsid were quantified and are presented in Table 1.

TABLE 1

|  | A | B/C | Final Capsid |
| --- | --- | --- | --- |
| Untreated | 2798 | 5046 | 739 |
| +apyrase | 2851 | 5999 | 133 |
| +detergent | 2656 | 6130 | 189 |

The untreated reaction contained Pr55 in complexes A, B, and C, as well as a peak in the final 750S capsid position, while the treated reactions contained no peak at the position of the final capsid product (Table 1). Treatment with either apyrase or detergent resulted in accumulation of additional material in complexes B and C, but did not result in accumulation of additional material in complex A. This is consistent with the idea that complexes B and C are the more immediate precursors of the 750S completed capsids, and that these interventions block the conversion of complexes B and C into the fully assembled capsid end-product.

b. Assembly-Defective Mutants. Further evidence of the existence of assembly intermediates A, B and C comes from experiments carried out in support of the present invention in which the intermediates accumulated when capsid assembly was blocked by specific mutations in Gag. Cell-free reactions were programmed with each of the previously described assembly-competent and assembly-defective Gag mutants (see FIG. 5), and were incubated for 150 min. The reaction products were diluted into 1.0% NP40 sample buffer on ice, and were analyzed by velocity sedimentation on 13 ml 15-60% sucrose gradients then analyzed by velocity sedimentation. Reactions programmed with wild-type Gag (FIG. 7A) or the assembly-competent Pr46 mutant (FIG. 7B) were found to have nearly identical profiles, in which over 30% of the radiolabeled chains synthesized formed completed immature capsids (that migrate at 750S) and the remainder was in the form of residual putative assembly intermediates A and B. Thus, these two assembly-competent forms of Gag appear to be equally efficient at capsid assembly in the cell-free system.

FIG. 7C shows the same analysis for the assembly-defective Pr41 mutant. All radiolabeled chains at the end of the Pr41 cell-free reaction were contained in a single, approximately 10S complex, corresponding to complex A. Since the 10S peak was very large and led to an irregular trail that could be masking 80S or 150S peaks, products of the Pr41 reaction were re-analyzed on a gradient that allowed high resolution in the 1 to 200S size range. All of the Pr41 translation product was in fact present in complex A, which was approximately 110S in size. Thus, in the cell-free system, it appears that Pr41 fails to progress beyond complex A, which is likely to represent the first intermediate in the assembly pathway.

Like Pr41, the myristoylation-incompetent GΔA mutant failed to assemble into 750S capsids (FIG. 5B, FIG. 7D), but unlike Pr41, GΔA had distinct peaks in both the 10S and 80S regions of the gradient (compare FIG. 7D to FIG. 7C). These data indicate that the GΔA mutant, which contains the entire Gag coding region except for the myristoylation signal, is capable of forming complex A, which appeared to be the first assembly intermediate in the pulse-chase experiment, as well as complex B, but does not progress further towards forming completed capsids. These data suggest that complex B is likely to be the second assembly-intermediate formed in the biogenesis of immature HIV capsids.

As shown above, in the absence of exogenously-added MCoA, wild-type Gag failed to assemble in the cell-free system (FIG. 3A), consistent with previous observations that myristoylation is required for proper capsid assembly to occur. Thus, a cell-free reaction programmed with wild-type Gag but performed in the absence of MCoA would be expected to be blocked at the same point in the assembly pathway as the GΔA mutant. Consistent with this, experiments carried out in support of the present invention demonstrate that assembly performed in the absence of MCoA results in formation of only complexes A and B and therefore closely resembles the GΔA mutant shown in FIG. 7D.

Analysis of a cell-free reaction programmed with the D2 mutant is shown in FIG. 7E. Unlike the previously described assembly-defective mutants, D2 was found to form a spectrum of Gag-containing complexes, including peaks corresponding to complexes A and B (at approximately 10S and 80S), a shoulder corresponding to complex C (in the 150S region), and an additional peak of approximately 400-500S, that will henceforth be referred to as complex D. Note that complex D trails into the 750S region, accounting for the appearance of small amount of assembly in the simpler analysis of capsid formation presented in FIG. 2. However, the detailed analysis presented here makes it clear that in fact there is no discrete peak in the region of completed capsid (750S). Thus, the D2 mutant appears to form a series of complexes corresponding in size to the assembly intermediates seen in the pulse-chase experiment (FIG. 7), as well as an additional complex of larger size, but fails to produce the completed 750S product.

Example 9

Host Cell Proteins Involved in Capsid Intermediate Formation

In further experiments carried out in support of the present invention, capsid intermediates formed and isolated as described above were analyzed for the presence of additional protein species. Immunoprecipitation reactions were carried out using several antibodies directed to cellular proteins. Surprisingly, a monoclonal antibody which recognizes a molecular chaperone known as TCP-1, antibody "23 c", was found to specifically interact with capsid intermediate fractions. TCP-1 is a 55-60 kD polypeptide that resides in a 20S particle and is not known to play a role in viral capsid assembly. Interestingly, antibody 23 c does not recognize the human or yeast homologs of TCP-1, but it does recognize a number of other eukaryotic proteins, presumably through recognition of their common C-terminal epitopes (LDD-COOH).

Further experiments in support of the invention revealed that the 23c reactive protein present in wheat germ extract migrates on SDS polyacrylamide gels as a 68 kilodalton protein. Further analysis reveals that the protein includes a peptide region having the following sequence: PRPYLD-VKQRLKAARVIRSLLRSN (SEQ ID NO: 2) and has the full open reading frame of SEQ ID NO:5.

Association of HP68 with the previously identified capsid assembly intermediates was assessed by measuring immunoreactivity of the 23c antibody. In these experiments, cell-free capsid formation reactions were programmed with Gag transcript (Example 1), pulse-labeled with 35-S cysteine for 3 minutes, and then chased with an excess of unlabeled cysteine. Under these conditions, chains synthesized during the first 25 minutes of the reaction are radiolabeled, while subsequently formed chains are unlabeled. Aliquots of the cell-free reaction were removed at various times during incubation and were either analyzed directly by SDS-PAGE or were subjected to immunoprecipitation with 23 c antibody.

In these reactions, it was verified that the total number of radiolabeled chains synthesized over time remained relatively constant, while the number of radiolabeled chains in the form of fully assembled capsids increased progressively over the course of reaction from 1.0% to 50.0%, with the largest increase in completed capsids occurring after 75 minutes. In contrast, the number of radiolabeled Gag chains bound to HP 68 (as assessed by immunoprecipitation with 23 c) was very low just after synthesis was completed, but increased significantly over time, reaching a peak at approximately 75 minutes into the incubation, then decreasing substantially during the final hour of the cell-free reaction. These observations are consistent with the conclusion, illustrated below, that HP 68 does not bind specifically to either newly-synthesized, unassembled Gag chains or to fully-assembled capsids.

In further experiments, radioactive HIV assembly intermediates formed as described above were subjected to velocity sedimentation, followed by immunoprecipitation using the 23 c antibody. With reference to the schematic shown in FIG. 9A, radiolabeled Gag chains in the form of the 80S and 500S assembly intermediates (intermediates B and D, respectively) were immunoreactive with 23c antibody, while fully assembled 750S capsids were not immunoreactive. Although intermediate C (150S) showed little or no immunoreactivity in these experiments, there is also very little of this intermediate present in the mixture at the time point assayed (2 hours), so the presence of HP68 in this fraction cannot be ruled out.

These results were also confirmed using assembly incompetent mutant viruses, as discussed above. Table 2 shows the results of experiments in which various assembly incompetent mutants or reaction manipulations were used to assess HP68 association with the above-defined intermediates. Cell-free reactions were programmed with wild-type ("Gag"), mutants Pr46 ("p46"), GΔA or Pr41 ("p41"), or were carried out in the presence of detergent ("Gag+det") or with the addition of apyrase ("Gag+apy"). Distribution of the above-described intermediates A-D and completed capsids was assessed for each condition, as described above, and 23c immunoreactivity was determined.

TABLE 2

Distribution of Gag-containing Intermediates

| | A | B | C | D | Complete capsid | 23c immuno-reactivity |
|---|---|---|---|---|---|---|
| Gag | + | ++ | + | ++ | +++ | ++ |
| p46 | + | ++ | + | ++ | +++ | ++ |
| Gag + det | ++ | ++ | + | − | − | + |
| Gag + apy | ++ | ++ | + | − | − | + |
| GΔA | ++ | ++ | − | − | − | + |
| p41 | +++ | − | − | − | − | − |

As illustrated, the absence of 23c immunoreactivity in the Pr41 mutant reaction, which fails to form any high molecular weight intermediates, indicates that there is no association of HP68 with intermediate A; in contrast, wild-type Gag and Pr46 mutant, which form high intermediates B-D are highly reactive. In the presence of detergent or apyrase, assembly intermediates A-C accumulate, as described above; under these conditions, 23c immunoreactivity was observed.

The foregoing data support one of the discoveries of the present invention that assembly of HIV capsids involves a host protein derived from the host cell, exemplified herein by HP68. In accordance with the present invention, HP68 is (i) is immunoreactive with monoclonal antibody 23c, and (ii) includes the sequences SEQ ID NO: 2. Specifically WGHP68 is one such homologue and is represented as SEQ ID NO:5. The present invention also appreciates that other cellular homologs of HP68 perform a similar function in hosting HIV assembly. Specifically contemplated by the present invention is a human homologue of HP68, which is associated with intermediates B-D present in human cell systems. By "homologue" is meant a protein or proteins that resemble HP68 in sequence (at least about 60% sequence identity by a standard protein/nucleotide sequence comparison algorithm), and which can be isolated from or detected in association with HIV capsid intermediates B-D.

Example 10

Correspondence of Cell-Free Capsid Intermediates to Cell-Produced Capsid Intermediates Cos-1 cells were transfected with a transfection vector encoding Pr55 cDNA, as described in the Examples. Four days later, the medium from the cells was collected. Viral particles in the medium were harvested by ultracentrifugation through a 20% sucrose cushion and then treated with detergent to remove envelopes. The transfected cells were solubilized in detergent to generate the cell lysate. The particles from the medium (FIG. 7A, right ordinate, open circles) and the detergent lysate of the cells (FIG. 7A, left ordinate, closed circles) were analyzed in parallel by velocity sedimentation on 13 ml 15-60% sucrose gradients. The amount of Pr55 protein in each fraction of these gradients was determined by immunoblotting and is expressed as percent of total Pr55 protein present. The calculated positions of 10S, 80S, 150S, 500S, and 750S complexes are indicated with markers above each graph. 750S represents the position of authentic immature (de-enveloped) HIV capsids.

Different cultures of Cos-1 cells were transfected with a transfection vector encoding the Pr41 mutant (FIG. 7B) or the D2 mutant (FIG. 7C). Transfected cells were lysed in detergent, and the lysate was analyzed by velocity sedimentation on 13 ml sucrose gradients, as in the experiments described with reference to FIG. 9A, above. The amount of capsid protein in each fraction of these gradients was determined by immunoblotting with anti-Gag antibody, and was expressed as percent of total immunoreactive protein present in each reaction. As shown, a substantial amount of fully assembled 750S capsid was present in the medium (FIG. 7A, open circles), while the cell lysate contained no 750S capsids (FIG. 7A, closed circles). These data are consistent with correspondence of intermediates in vivo with those reported above for cell-free capsid synthesis and assembly.

Analysis of the Pr41 mutant transcript is shown in FIG. 7B. This mutant appears to be blocked after the first assembly intermediate in the cell-free system. Analysis of the D2 mutant, which appears to be blocked at the end of the assembly pathway in the cell-free system, shows accumulation of corresponding Gag-containing complexes within cells. Cos cells were transfected with each of these mutants, and the medium as well as the lysate were examined by immunoblotting. Medium from cells transfected with the assembly-defective Pr41 or D2 mutants did not contain 750S completed capsids. The cell lysate of Cos cells transfected with the Pr41 mutant contained only material that peaked in the 10-S region of the velocity gradient (FIG. 7B), resembling what had been found when the Pr41 mutant was expressed in the cell-free system (see FIG. 6C). The observation that the Pr41 reaction product migrated as a single complex that peaked in the 10S region was confirmed by analysis on a variety of different velocity sedimentation gradients that allowed higher resolution in the 1 to 200S size range.

In contrast, the cell lysate of Cos cells transfected with the D2 mutant contained a spectrum of immunoreactive complexes that ranged in size from 110-S to 500-S (FIG. 7C), resembling what was found when D2 was expressed in the cell-free system (FIG. 6E). Thus, the data from transfected cells suggests that the behavior of Gag mutants in the cell-free system reflect events in capsid assembly that occur in living cells.

Example 11

Model for Capsid Assembly

A model of the HIV capsid assembly pathway is shown in FIG. 9A. This model is based on the simplest interpretation of the data presented herein. This model is presented for purposes of summarizing these data, and is not to be construed as a representation of a particular underlying mechanism to which the present invention must adhere. In particular, the exact relationship of the subcellular fraction dependent step, as well as the apyrase- and detergent-sensitive steps to the pathway are not to be taken as a basis for limiting the claimed method or cell-free system of the present invention. Moreover, although the order of complex formation shown is consistent with the data presented, this order should not be used to limit the claimed intermediate compositions.

According to the model presented in FIG. 9A, newly-synthesized Gag proteins are myristoylated co-translationally. Nascent Gag polypeptides appear to chase into completed immature capsids by way of a series of Gag-containing complexes (complexes A, B, C, and D). Evidence from the studies reported herein suggests that complexes A, B, and C may constitute assembly intermediates. Complex D may similarly constitute an assembly intermediate or may represent a side-reaction. A subcellular, detergent-resistant factor appears to be required for capsid formation. In addition, ATP and a membrane fraction are also required for assembly to take place, as evidenced by apyrase and detergent sensitivity of the assembly process.

FIGS. 9(B-D) show the proposed correspondence between assembly mutants p41, GΔA, D2 and p46 to the model pathway, based on the data presented above.

Example 12

HIV-1 Capsid Formation in a Cell Free System

Purification and Sequencing of HP68

For immunoaffinity purification, 1 ml WG extract was centrifuged at 100,000 rpm in a Beckman TL100.2 rotor for 15 min. The supernatant was subjected to immunoprecipitation using 50 µg of affinity purified 23c antibody (Stressgen) or an equivalent amount of control antibody (α-HSP 70, Affinity Reagents). Immunoprecipitation eluates were separated by SDS-PAGE and transferred to a polyvinylidene difluoride membrane. A single 68 kD band was observed by Coomassie-staining in the 23c immunoprepicipation lane but not on the column. A portion of this band was excised for microsequencing (ProSeq, Salem, Mass.) and the remainder was used for immunoblotting to confirm that the band was recognized by the 23c antibody. The purified protein, which was blocked at the N-terminus, was cleaved with CNBr and treated with o-phthalaldehyde to allow selective microsequencing using Edman degeneration of peptides containing proline near the N-terminus.

2. cDNA Amplification

The following degenerate 3' oligonucleotides corresponding to the C-terminal peptide sequence of WGHP68 3' was synthesized: ATGAATTC(ACTG)GG(ACTG)CG(GA)TA(GA)TT(ACTG)GT(ACTG)GG(GA)TC (SEQ ID NO.3) and ATGAATTC(ACTG)GG(CT)CT(GA)TA(GA)TT(ACTG)GT(ACTG)GG(GA)TC (SEQ ID NO. 4). The WGHP68 coding region was amplified by PCR using WG cDNA (Invitrogen), as the template, 3' oligos corresponding to the WGHP68 C-terminal peptide sequence and 5' oligos corresponding to the vector into which the cDNA was cloned. This PCR reaction was performed four independent times and each time yielded a single 2 kB product. These PCR products were ligated into vectors by TA cloning (Invitrogen). DNA sequencing revealed each cDNA product to be identical. 3' and 5' coding and non-coding ends were obtained through nested RACE PCR reactions using degenerate oligos corresponding to sequences in the internal region of HP28. From overlapping cDNA clones, a complete open-reading frame for WGHP68 was defined. The start was identified by the presence of a defined Kozak consensus sequence at the initiating methionine, the presence of two in-frame stop codons upstream of the first methionine, the absence of ATG codons upstream from the presumptive start site (Kozak, Mamm Genome (1996) 7:563-74), and by homology to the human homologue in GenBank (Bisbal et al. J Biol Chem, (1995) 270:13308-17). The coding sequence for WGHP68 (SEQ ID NO: 5) has been deposited in GenBank under accession number AY059462.

3. Generation of Antisera

Polyclonal rabbit antisera were generated against C-terminal peptides of Hu and WGHP68 (FIG. 10) and against the 19 N-terminal amino acids of human RNase L by injecting rabbits with peptides coupled to KLH. Affinity-purified αHuHP68b antisera was prepared by binding antisera to the HuHP68 C-terminal peptide coupled to agarose and eluting with glycine.

4. Transfections, Immunoprecipitation, Immunofluorescence, and Immunoblotting

Cos-1 cells were transfected using Gag expression plasmids pCMVRev and PSVGagRRE-R described in Simon et al, J. Virology, (1997) 71:1013-18. HP68 plasmids for mammalian expression were constructed by using PCR to insert the coding regions for WGHP68, amino acids 1-378, Nhe1/Xba1 of pCDNA 3.1 (Invitrogen). Coding regions of all constructs were sequenced. Cells were transfected using Gibco Lipofectamine (Cos-1) or Lipofectamine Plus (293T). All transfections used a constant amount of DNA (18 µg per 60 mm dish). Medium was changed 24 hours after transfection and harvest was performed 28 or 60 hours after transfection for immunofluorescence and immunoblotting respectively. For immunofluorescence, cells were fixed in paraformaldehyde, permeabilized with 1% triton, and incubated with mouse HIV-1 Gag antibody (1:50) and affinity-purified HuHP68 antiserum (1:2000), followed by Cy3- and Cy 2-coupled secondary (Jackson) (1:200). 178 cells were quantitated. For immunoblotting in FIG. 13 rat IgG was added to medium as a tracer at 10 µg/ml at the time of harvest, and cells were harvested in SDS sample buffer with boiling. For quantitation of immunoblots, bands were compared to an immunoblot standard curve generated with known quantities of sample.

Figure 11:
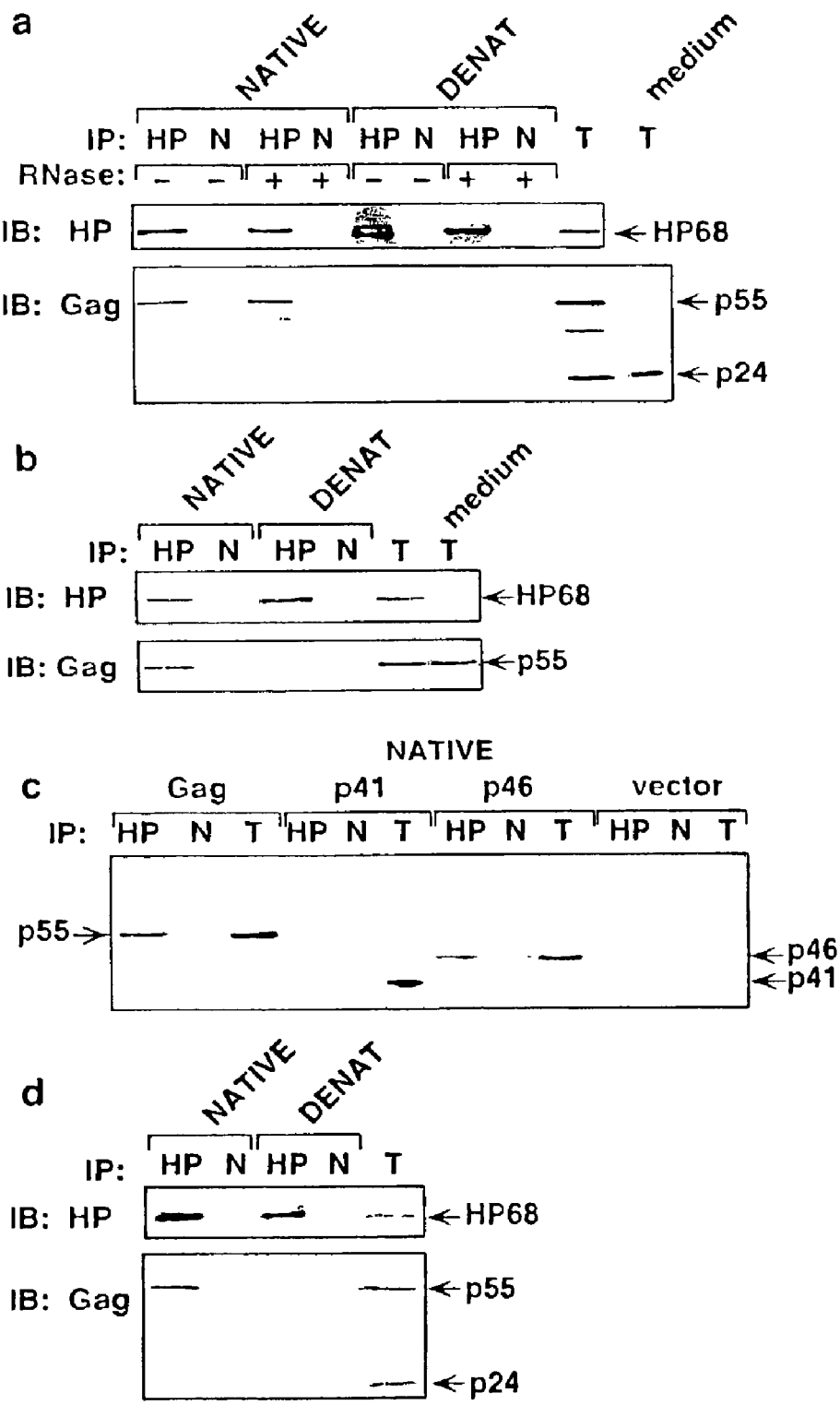

For immunoprecipitations followed by immunoblotting (FIGS. 11 and 15), affinity purified α-HuHP68 antisera described above was coupled to Protein A beads (7 mg/ml beads) to generate αHuHP68b. Confluent Cos-1 cells in 60 mm dish were transfected, harvested in 300 µl NP40 buffer and 100 µl of lysine was immunoprecipitated with 50 µl of αHuHP68b. Immunoprecipitates were analyzed by SDS-PAGE followed by immunoblotting with antibodies described.

5. Immunodepletion-Reconstitution

WG extract (150 µl) was immunodepleted for 45 min at 4° C. with 100 µl beads coupled to antibody against WGHP68. Cell-free reactions (15 µl) were programmed (Lingappa et al., *J. Cell Biol.* 136:567-81 (1997)) using non-depleted WG or depleted WG. To some reactions containing depleted WG, purified WGHP68-GST or HuHP68-GST fusion protein or GST alone was added (2 µl of approx. 20 ng/µl) at the start of the reaction. After 3 hours at 26° C., NP40 was added to a final concentration of 1% and reactions underwent velocity sedimentation (5 ml, 15-60% sucrose gradients, Beckman MLS55 rotor: 45,000 rpm, 45 min). Thirty fractions, collected using a fractionator, were analyzed by SDS-PAGE and AR, followed by densitometry of Gag in each lane. For Proteinase K digestion, aliquots of fractions from the 500S and 750S regions of the gradient were collected and subjected to a 10 min incubation at RT with either no Proteinase K or 0.1 µg/ml Proteinase K. Digestion was terminated by adding SDS and freezing. Samples were analyzed by SDS-PAGE and AR. Graphs show average of three independent experiments (+/− SEM).

To generate purified HP68, WGHP68 and HuHP68 were subcloned into a pGEX vector (Pharmacia), to encode fusion proteins containing GST at the N-terminus. Expression was induced with 1 mM IPTG for 3 hours; sarcosyl (0.5%) and PMSF (0.75 mM) was added after sonication. 17,000×g supernatant was incubated with glutathione beads and eluted with 40 mM glutathione in 50 mM Tris, pH 8.0. Concentration of fusion protein and GST in eluate was determined using the Coomassie Plus protein assay (Pierce).

Two cell-free reactions were programmed with HIV-1 Gag transcript and immunodepleted WG, and WGHP68-GST was added to one of these reactions. In parallel, Cos-1 cells were transfected resulting in expression of Gag and release of immature HIV-1 particles. The cell-free reactions and medium from transfected cells was treated with 1% NP40 to remove envelopes, and membranes associated with capsids, subjected to velocity sedimentation on 2 ml 20-66% sucrose gradients (Beckman TLS55 rotor, 35 min, 45,000 rpm).

Example 13

Characterization of HP68

1. Wheatgerm HP68 (WGHP68) was isolated from WG extracts by immunoaffinity purification using 23c antibody. Microsequencing yielded two well-defined sequences of 24 or more amino acids. Each sequence was approximately 70% homologous to a different region of a single 68 kD protein identified as human RNase L inhibitor (Bisbal et al. JBC (1995) 270:13308-17; GenBank A57017, SEQ ID NO:6) (FIG. 10). Using degenerate oligonucleotides (SEQ ID NO: 3 and 4) corresponding to the C-terminal peptide, a 2 kB cDNA was amplified from a WG cDNA mixture. Sequencing revealed that this cDNA has 70% identity overall to the cDNA coding for the 68 kD human RNase L inhibitor (here termed HuHP68) (Bisbal et al. JBC (1995) 270:13308-17; Bisbal et al. Methods Mol Biol (2001) 160:183-98). The open reading frame WGHP68 was deduced and its full amino acid sequence was predicted (FIG. 10). The 604 amino acid sequence of WGHP68 shows 71% identity overall with the 599 amino acid sequence but of human RNAse L inhibitor (HuHP68). Both WGHP68 and HuHP68 contain two canonical ATP/GTP-binding motifs (Traut T. Eur J. Biochem (1994) 222:9-19) as well as the LDD-COOH epitope (FIG. 10).

HuHP68 is known to bind and inhibit RNase L (Bisbal et al. JBC (1995) 270:13308-17; Bisbal et al. Methods Mol Biol (2001) 160:183-98), an interferon-dependent nuclease associated with polysomes (Salehzada. et al JBC (1991) 266: 5808-13; Zhou et al. Cell (1993) 72:753-65) and activated by the interferon-sensitive 2'-5' linked oligoadenylate (2-5S) pathway. Interferon-dependent induction and activation of RNase L results in degradation of many viral RNAs (Player et al. Pharmacol Ther. (1998) 78:55-113; Samuel C. Virology (1991) 183:1-11; Sen et al. JBC (1992) 267:5017-20). Previously, overexpression of the 68 kD RNAse L inhibitor (HuHP68) in HIV-1-infected cells has been shown to increase virion production by reducing RNase L activity, resulting in higher levels of HIV-1 RNA and HIV-1-specific protein (Martinand et al. J. Virology (1999) 73:290-6). These findings that WGHP68 binds to Gag-containing, post-translational intermediates during cell-free HIV-1 capsid assembly led to further investigation of whether HuHP68 binds to and acts on fully-synthesized Gag chains post-translationally in cells, in addition to binding and inhibiting RNase L as previously described (Salehzada et al. JBC (1991) 266:5808-13; Zhou et al. Cell (1993) 72:753-65).

2. Association of HP68 with HIV-1 Gag Infected Human Cells

To analyze the function of HP68 in cells, a peptide-specific polyclonal antibody was generated against both C-terminal residues of WGHP68, and C-terminal residues of HuHP68 (FIG. 10). These antisera specifically recognize a 68 kD protein in WG and in primate cells respectively, by immunoprecipitation as well as Western blotting. To determine whether HP68 is associated with assembling HIV-1 Gag chains in human cells, human 293T cells were transfected with the pBRUΔenv plasmid. Immunoprecipitates were analyzed by Western blotting using a monoclonal antibody to HIV-1 Gag. Hiv-1 Gag is co-immunoprecipitated by αHuHP68 under native condition but not after denaturation (FIG. 11A). HP68 appears to associate with Gag post-translationally. These data reveal the HuHP68 is associated with HIV-1 Gag in human cells that are producing mature HIV-1 virions.

3. HP68 Associated with Gag Post-Translationally in Human Cells

Figure 12:
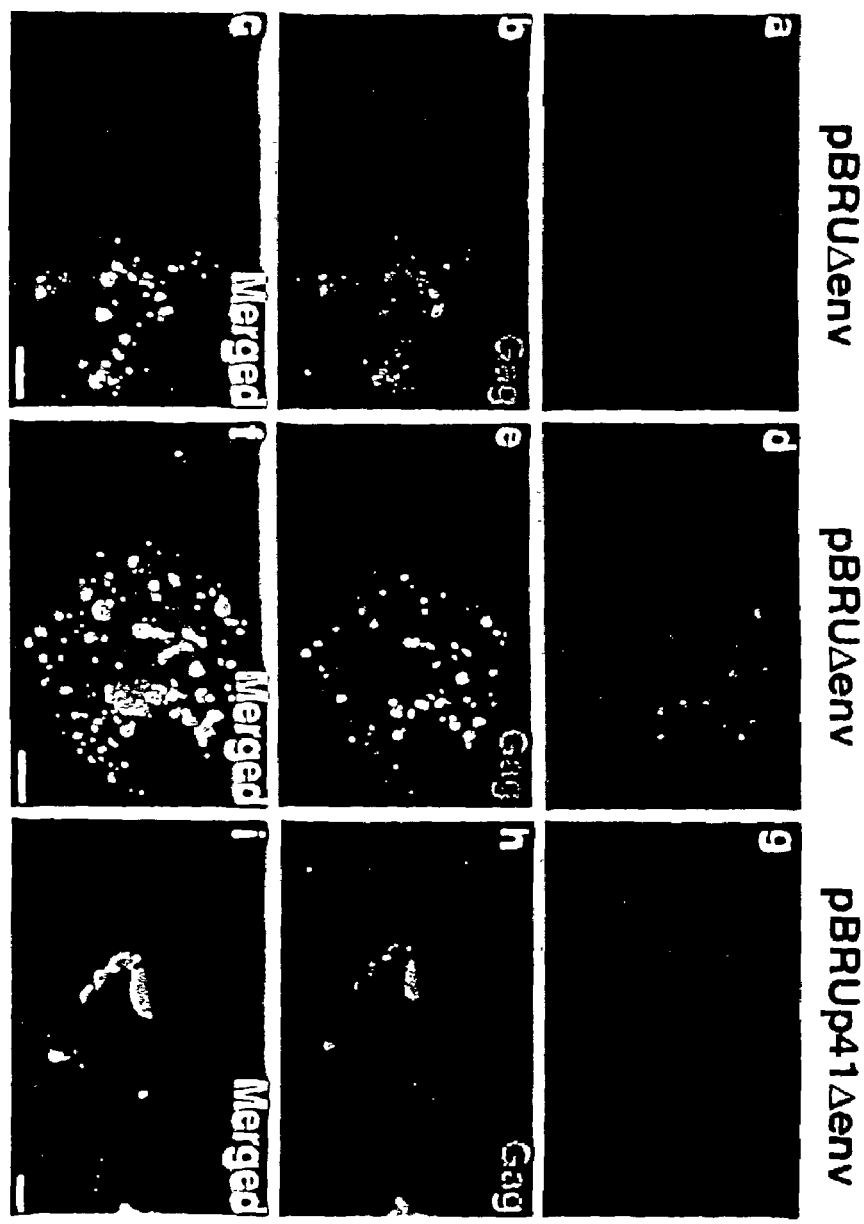
FIG. 12 shows co-localization of HP68 with HIV-1 Gag in mammalian cells.

Further investigation revealed that HP68 is associated with Gag in RNase-treated and untreated cell lysates analyzed in parallel (FIG. 11A). These findings that HuHP68 binds completely-synthesized Gag chains, and does so in the absence of intact RNA, indicates that this host protein is bound to Gag-containing complexes post-translationally. FIG. 11B demonstrates that Gag is associated with HP68 under native conditions, but not after denaturation when immunoprecipitated with αHuHP68b. This confirms that HP68 binds HIV-1 Gag in the absence of the HIV-1 protease and other HIV-1 specific proteins. FIG. 11C demonstrates that HP68 is associated with wild-type Gag and with the assembly-competent p46 mutant, but is not associated with assembly incompetent p41 mutant. Thus, HP68 appears to associate specifically with assembling Gag chains in mammalian cells, as it did in the cell-free system. Confirmation studies were performed with fully infectious human T-cells, wherein immunoprecipitation was performed with αHuHP68 demonstrating that HP68 associates with Gag in infected human T-cells. FIG. 5D shows that αHuHP68b co-immunoprecipitated HP68 and Gag from T-cell lysates. Confirmation of co-association of HP68 and Gag was demonstrated with immunofluorescent microscopy (FIG. 12). HP68 staining reveals two different patterns of localization. HP68 is present in a diffuse pattern in 100% of the cells that fail to become transfected and do not express HIV-1 Gag (two cells on left in FIGS. 12A-C), as well in 100% of control cells that are transfected with constructs expressing control proteins. In cells expressing HIV Gag, HP68 is found in a coarsely clustered pattern (FIGS. 12D and F) FIGS. 12C, F and I show a merged image where there is a striking co-localization of HP68 and Gag in the yellow coarse cluster. Recruitment of HP68 into clusters containing Gag is seen in 100% of cells expressing HIV-1 Gag. In contrast, when cells are transfected with pBRUp41Δenv, which encodes an assembly defective mutant, HP68 is not found in a clustered pattern or co-localized with HIV Gag (FIGS. 12G-I).

4. HP68 Mutant Binds HIV-1 Gag and Blocks HIV-1 Particle Formation

To examine HP68 function (i.e. is HP68 association with Gag important for HIV-1 particle formation), Cos-1 cells were co-transfected with WGHP68-Tr1 and a Gag expression plasmid (FIG. 13). Increasing expression of WGHP68Tr-1 results in a 4.7 fold dose-dependent decrease in the amount of HIV-1 Gag protein in the medium (FIG. 13A, p55 blot and graph). Gag and actin levels in cell lysates remained unchanged (FIG. 13B), indicating that the effect of WGHP68-Tr1 is not mediated by changes in Gag synthesis or degradation, and that WGHP68-Tr1 is not toxic to cells. Reduction in virion formation upon WGHP68-Tr1 expression, even when Gag levels are unchanged, suggests that HP68 promotes virion formation by a post-translational mechanism. Co-immunoprecipitation of Gag with epitope-tagged WGHP68-Tr1 confirmed that WGHP68-Tr1 competes with wild-type HP68 for binding to HIV-1 Gag (data not shown).

5. Capsid Assembly is Inhibited by Depletion of HP68 and Restored by Reconstitution.

Figure 14:
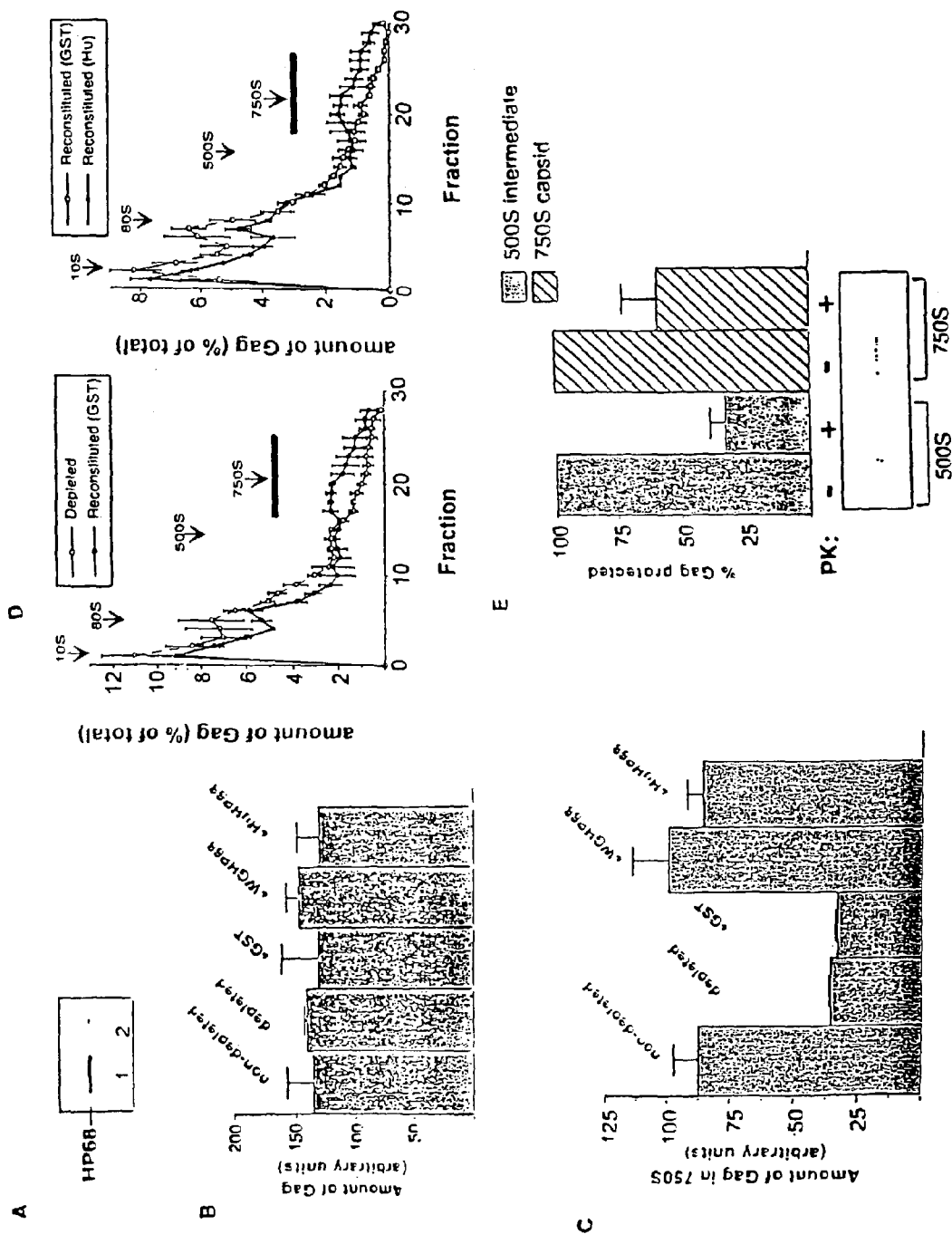
FIG. 14 shows HP68 depletion-reconstitution.

To demonstrate that HP68 is essential for post-translationally events in immature capsid assembly, endogenous HP68 was immunodepleted with αWGHP68 from wheat germ extracts prior to programming for a cell free reaction. FIG. 14A shows in lane 1 vs 2 an extract with reduced levels of WGHP68, but which can still support the same amount of Gag production (FIG. 14B, non-depleted vs. depleted). FIGS. 14C and D show that when immunodepleted (for HP68) cell free extracts are programmed with HIV-1 Gag transcript that the 750S completed capsid were dramatically reduced. Furthermore, the depleted reaction appeared to be arrested at the 500S post-translational assembly intermediate complex, with accumulation of other previously-identified post-translational assembly intermediates (10S and 80S), but no 750S completed immature capsid product (FIG. 14D).

Reconstitution was demonstrated by the addition of either WGHP68-GST or HuHP68-GST to HP68 immunodepleted WG extract programmed with HIV-1 Gag transcript, a 3-fold increase in the amount of 750S capsid was observed (FIGS. 14C and D). This is a level observed in non-depleted extract. Addition of either fusion protein (WGHP68-GST or HuHP68-GST) had no effect on the total amount of radiolabeled Gag synthesized (FIG. 14B), indicating that the reconstituted protein acts post-translationally. These findings demonstrate that HP68 is required for conversion of post-translational assembly intermediates into completely assembled 750S immature HIV-1 capsids in the cell-free system. In addition, further experiments demonstrate that HP68 promotes a conformational change in capsid structure, converting protease-sensitive capsid assembly intermediates into immature capsid structures that are relatively resistant to exogenous proteases. FIG. 14E shows that upon treatment of protease K to the sucrose gradient fractions, 500S and 750S, that 500S capsid assembly intermediates were sensitive to protease digestion while 750S completed capsid were relatively protease resistant. Thus, the 750S capsid has undergone a conformational change, with the help of HP68, which prevents exogenous proteases from degrading the completed capsid.

6. HP68 Selectively Associates with HIV-1 Gag and Vif but not with RNase L

Figure 15:
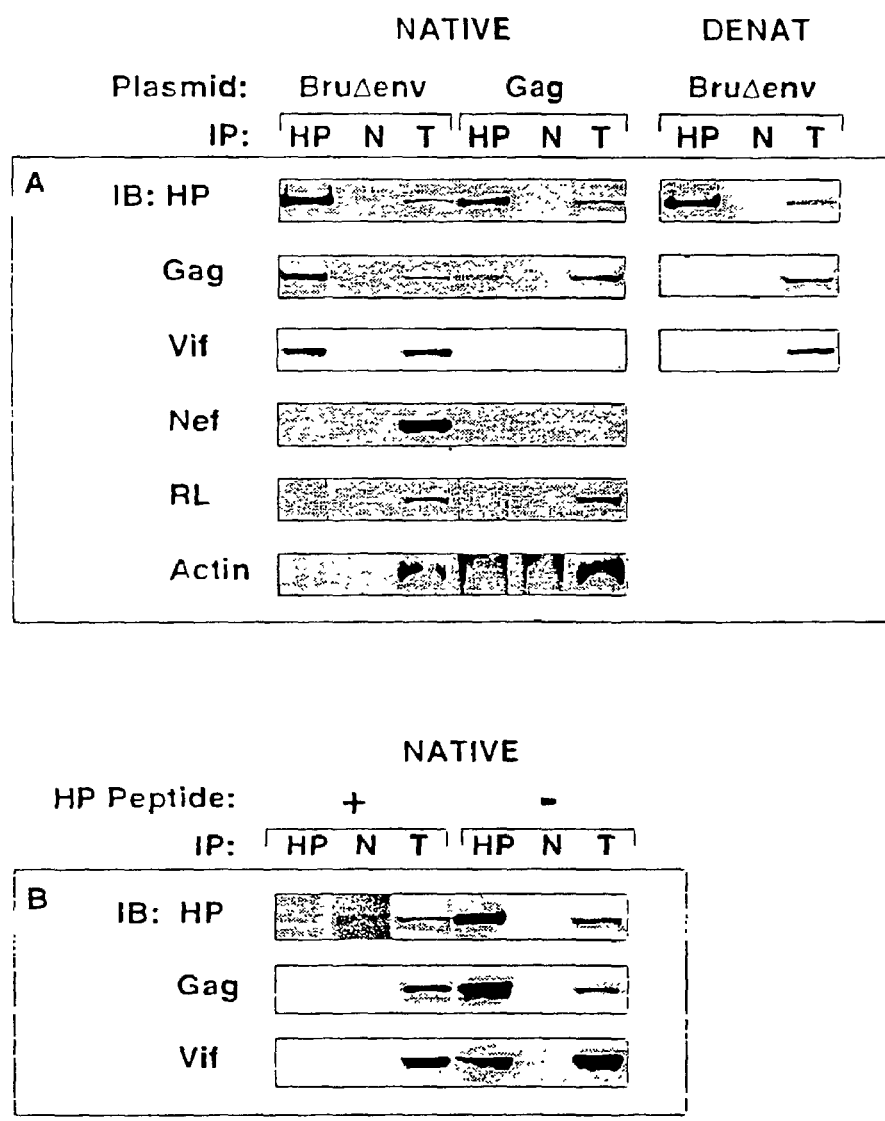
FIG. 15 shows HuHP68 co-immunoprecipitates HIV-1 Gag and Vif but not Nef or RNase L.

FIG. 15 shows that the HP68 protein that facilitates HIV-1 capsid formation binds HIV-1 Gag and Vif proteins but does not bind RNase L in human cells, which have been transfected with plasmids expressing Gag alone or with the plasmid pBRUΔenv. These findings suggest that HP68 not only acts by two different mechanisms but resides in two different complexes in host cells as well. In one complex, HP68 associates with and inhibits RNase L, a cellular protein that is upregulated by interferon, binds to ribosomes, and promotes degradation of viral RNA (Zhou et al. Cell (1993) 72:753-65; Player et al. Pharmacol Ther (1998) 78:55-113; Samuel C. Virology (1991) 183:1-11; Sen et al. JBC (1992) 267:5017-20). An aspect of this invention is that, as described above, HP68 is also present in a second, separate complex (assembly intermediate), in which HP68 acts post-translationally to promote virion formation.

To demonstrate these differences in HP68 and the specificity for HIV proteins, Cos-1 cells expressing pBRUΔenv were subjected to immunoprecipitation using αHuHP68b followed by immunoblotting with antibodies to Gag, Vif, Nef, RNase L and actin. αHuHP68b co-immunoprecipitated Gag and Vif under native conditions but not denatured conditions. RNase L and HIV Nef protein were not co-immunoprecipitated, indicating that HP68 is associated with select HIV proteins in a complex that does not contain RNase L.

Example 14

Assembly of HCV Capsid in a Cell-Free System

Wheat germ extracts were used to program the translation and assembly of HCV core polypeptides in a manner analogous to the HIV capsid assembly system as described in Example 1, with the exception that it is not necessary to add myristoyl CoA to the system. In order to support efficient immature HCV-1 capsid assembly the extracts were ultracentrifuged briefly (most likely to remove an inhibitor; see Lingappa, et al., (1997) Cell Biol 136: 567-81). HCV capsid assembly does not appear to be affected by addition of non-ionic detergent to the assembly reactions. This is consistent with the idea that HCV core probably assembles into pre-formed capsids in the cytoplasm. While HCV core has been shown to have a hydrophobic tail that is associated with the cytoplasmic face of the ER membrane (Santolini, et al., (1994) J Virol 68-3631-41; Lo, et al., (1996) J Virol 70: 5177-82). This association apparently is not required for proper HCV capsid assembly, and may instead play a role in association of HCV core with the E1 envelope protein.

Figure 16:
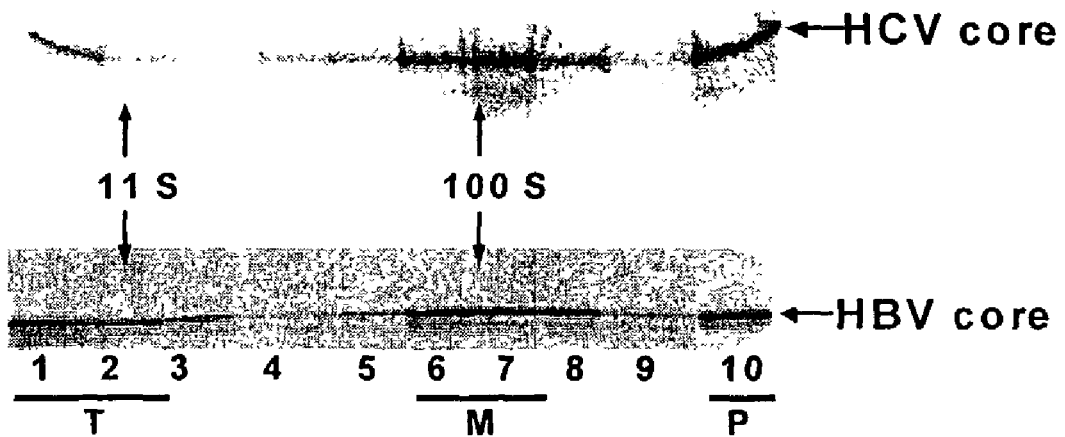
FIG. 16 shows velocity sedimentation of HCV and HBV core assembled in a cell-free system. Cell-free reactions programmed with HCV or HBV core transcript were incubated for 2.5 h and analyzed by velocity sedimentation on 2 ml sucrose gradients containing 1% NP40 (55,000 rpm×60 min. in Beckman TLS55 rotor). Fractions (200 microliters each) were collected from top of gradient and examined by SDS-PAGE and autoradiography. In both reactions, core chains form 100S particles and complexes of other sizes.

After incubation for 2.5 hours, the products of the HCV core cell-free reaction were analyzed by velocity sedimentation on 2 ml sucrose gradients containing 1% NP40 (55,000 rpm×60 min. in Beckman TLS55 rotor). Fractions (200 microliters each) were collected from the top of gradient and examined by SDS-PAGE and autoradiography. A particle of 100S was produced in this reaction (see FIG. 16). Thirty to 50% of newly-synthesized HCV core chains form these ~100S particles by the end of the reaction, located in the middle (M). The remainder of HCV core chains are in the top fraction (T) and in the pellet (P) closely resembling what we have seen previously with assembly of HBV core into capsids in a cell-free system (Lingapaa, J. R., et al., (1994) J Cell Biol 125: 99-111). To confirm that the 100S de-enveloped particle represents HCV capsids, the factions containing de-enveloped capsids (lanes 6 and 7) from the velocity sedimentation gradient were analyzed by equilibrium centrifugation on CsCl (50,000 rpm×20 hours using a TLS55 Beckman rotor) using a 337 mg/ml CsCl solution. Fractions were collected, TCA precipitated, analyzed by SDS-PAGE and autoradiography, and quantitated by densitometry. HCV core protein peaked in fraction 6. The density of fraction 5/6 (middle of the gradient, indicated with arrow) is 1.25 g/ml. The buoyant density of approximately 1.25 g/ml (FIG. 17), is identical to that of HCV capsids (without envelopes) produced in infected cells (Kaito, M. et al., ((1994) J Gen Virol 75: 1755-60; Miyamoto, H. et al., (1992) J Gen Virol 73: 715-8).

Figure 17:
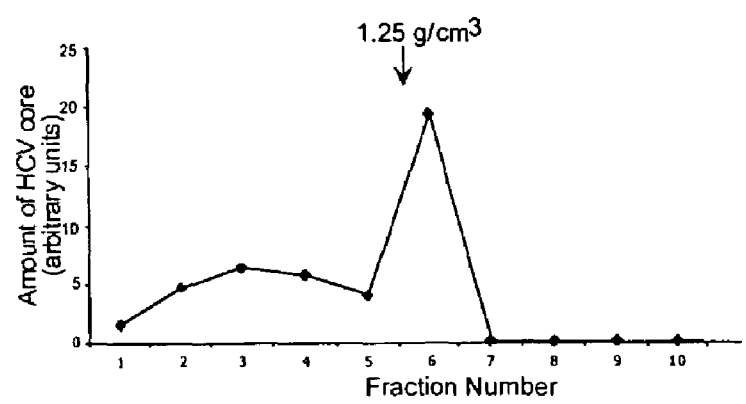
FIG. 17 shows that 100S particles produced in the cell-free system have the buoyant density expected for HCV capsides. Products of a cell-free assembly reaction programmed with HCV core transcript were separated by velocity sedimentation, as in FIG. 16. Fractions 6 and 7 (100S core particle) were analyzed by equilibrium centrifugation (50,000 rpm×20 hours using a TL55 Beckman rotor) using a 337 mg/ml CsCl solution. Fractions were collected, TCA precipitated, analyzed by SDS-PAGE and autoradiography, and quantitated by densitometry. HCV core protein peaked in fraction 6. The density of fraction 5/6 (middle of the gradient, indicated with arrow) is 1.25 g/ml.

Fractions containing the 100S particle were analyzed by transmission EM [(TEM)/Fractions 6 and 7 from the velocity sedimentation gradient described in FIG. 17 were pooled, put on a formvarcoated grid, negatively-stained with uranyl acetate, and examined by TEM.] 30-50 nm spherical particles composed of capsomeric subunits were clearly seen. This is the size expected for HCV capsids that have had their envelopes removed or that are not yet enveloped (Mizuno, et al., (1995) Gastroenterology 109: 1933-40; Takahashi, et al., (1992) Virology 191: 431-4). (Note, in contrast, that ribosomes have a diameter of 12-20 nm.) Thus, by three criteria presented here (velocity sedimentation, buoyant density, and electron microscopy), HCV forms capsids in the cell-free system that closely resemble those found in infected cells.

Example 15

Assembly of HCV Core Truncations Containing the Homotypic Interaction Domain

Figure 18:
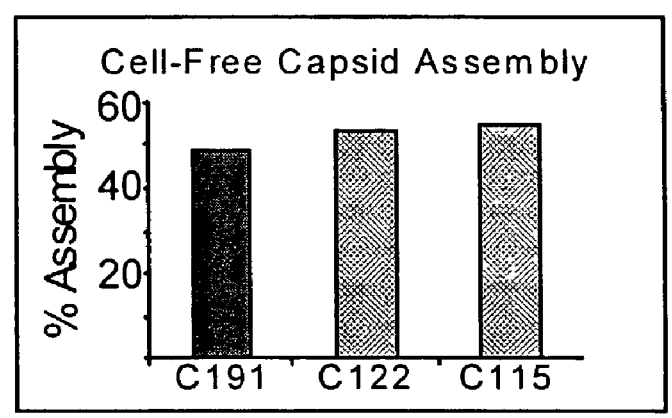
FIG. 18 shows mutants containing the hydrophilic interaction domain of core assemble in the cell-free system. Cell-free reactions were programmed with wild-type HCV core (C191) or mutants in core truncated at amino acids 122 or 115 (C122 vs. C115), and analyzed by velocity sedimentation on 2 ml sucrose gradients (as described in FIG. 16). Fractions were examined by SDS-PAGE, and autoradiographs were quantitated. Graph shows amount of each core protein present in 100S particles as % of total synthesis.

Previous findings indicate that the HCV core interaction domain is located in the hydrophilic region from aa 1 to 115 (Matsumoto, et al., (1996) Virology 218:43-51; Nolandt, O. et al., (1997) J Gen Virol 78: 1331-40; Yan, B. B., et al., (1998) Eur J Biochem 258:100-6; Kunkel, M. et al, (2001) J Virol 75: 2119-29). Therefore HCV core truncations that encompass this domain should assemble into completed capsids in the cell-free system. Assembly reactions were programmed with transcripts encoding C191, C115, and C124. Total synthesis was similar for all 3 constructs. After incubation for 2.5 hours reaction products were analyzed by velocity sedimentation, and the amount of core that migrated in 100S particles was graphed as % of total core synthesized (see FIG. 18). The two C-terminal truncation mutants assembled into 100S particles, as did full-length core. The finding that the domains required for assembly are located in the first 115 amino acids of HCV core is consistent with observations in other systems (Matsumoto, et al., (1996) Virology 218:43-51).

Figure 28:
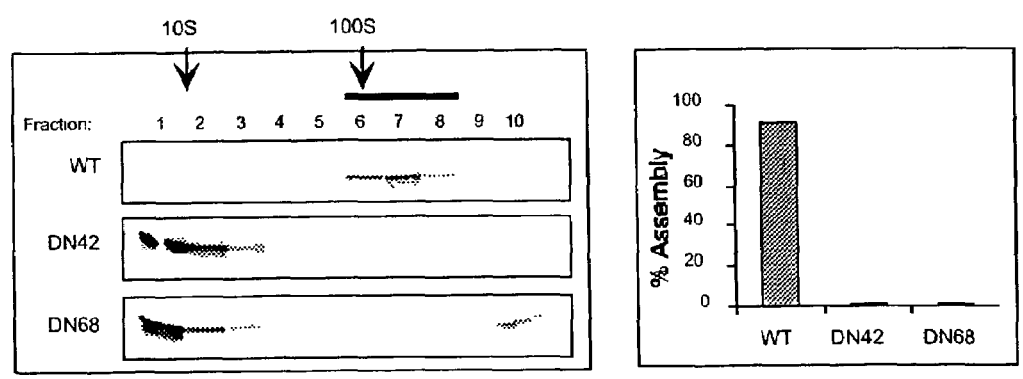
FIG. 28 shows that N-terminal deletions mutants of HCV core fail to assemble in a cell-free system.

Mutants of HCV core were also engineered to encode amino acids 42-173 (ΔN42) and amino acids 68-173 (ΔN68) (FIG. 28). Transcripts of wild-type (WT) C173 core (amino acids 1-173) or the N-terminal deletion mutants described above were used to program cell-free translation and assembly reactions. Reaction products were analyzed by velocity sedimentation on sucrose gradients. In FIG. 28, left panel, cell-free assembly reactions were programmed with WT and mutant core transcripts and separated by velocity sedimentation. Fractions were analyzed by SDS-PAGE and autoradiography. S values are indicated above fractions, and the dark bar indicates the expected position or fully assembled capsids. FIG. 28, right panel, shows the amount of radiolabeled core that migrates in the 100S fraction as a percentage of total core protein synthesized (% assembly), which was determined by densitometry of autoradiographs in the left panel. Wild-type C173 assembled into 100S capsid-like structures very efficiently.

Example 16

Evidence that HCV Capsid Assembly Proceeds Through an Ordered Pathway of Intermediates To determine whether capsid assembly occurs by way of assembly intermediates, a pulse-chase experiment was performed in the cell-free system. Cell-free reactions were programmed with wild-type HCV core, labeled for 3 min. with 35-S cysteine, and chased with unlabeled cysteine. Aliquots were taken at the times indicated, and analyzed by velocity sedimentation on 2 ml sucrose gradients, as described in FIG. 18. Fractions were examined by SDS-PAGE, and autoradiographs were quantitated. The graph shows amount of HCV core protein present in the top fractions 1 and 2 (T), vs. middle fractions 6, 7, and 8 (M), vs. pellet (P). Middle fractions represent 100S completed HCV capsids. Progression of labeled core polypeptides through complexes of different sizes was examined by velocity sedimentation of aliquots taken at different times during the chase reaction. The results suggest that capsid proteins first appear at the top of the gradient (~10-20S complexes that are likely to represent dimers or small oligomers), then appear in the pellet, which may represent a large assembly intermediate, and finally appear in the middle of the gradient (~100S), in the position of completed capsids. These results indicate capsid assembly occurs through an ordered pathway of assembly intermediate complexes. The pellet increases initially, and then decreases as completed capsids are formed, indicating the presence of a high-molecular weight assembly intermediate in the pellet.

Example 17

HCV Core Proteins Appear to be Associated with a Host Protein in the Cell-Free System Studies of other viral capsids such as HIV-1 and HBV capsids, suggest that capsid assembly in cells is energy-dependent and requires host factors (Lingappa, J. R., et al., (1997) J. Cell Biol 136:567-81; Lingappa, J. R. (1994) J Cell Biol 125: 99-111; Weldon, R. A., et al., (1998) J Virol 72: 3098-106; Mariani, R., et al., (2000) J Virol 74: 3859-70; Mariani, R. et al., (2001) J Virol 75: 3141-51; Unutmaz, D., et al., (1998) Sem in Immunol 10: 225-36). Cellular factors are also implicated in HCV capsid assembly, since assembly of full-length core in the absence of cellular factors results in particles that have abnormal sizes and shapes as compared to capsids produced in cells (Kunkel, M., et al., (2001) J Virol 75: 2119-29).

Using the cell-free system to search for host factors that could be involved in capsid formation, two assumptions were made: 1) that such a host factor likely is associated with core chains transiently during assembly, and 2) that candidates for host factors involved in HCV capsid assembly include the general class of molecular chaperones, in particular eukaryotic cytosolic chaperones. Proteins that are recognized by antibodies directed against the eukaryotic cytosolic chaperone TCP-1 have been found associated with capsid proteins of two different viruses, namely HBV (Lingappa, J. R. (1994) J Cell Biol 125: 99-111). And the type d retrovirus Mason-Pfizer Monkey Virus (M-MPV) Hong, S., et al, (2001) J Virol 75: 2526-34). Note that in both of these studies, TCP-1 has not been definitively identified as the co-associating protein, so the possibility of a cross-reacting protein has not yet been ruled out. The capsids of both of these viruses pre-form in the cytoplasm, unlike the capsids of type C retroviruses such as HIV-1 (Wills and Craven (1991) Aids 5: 639-54).

Figure 19:
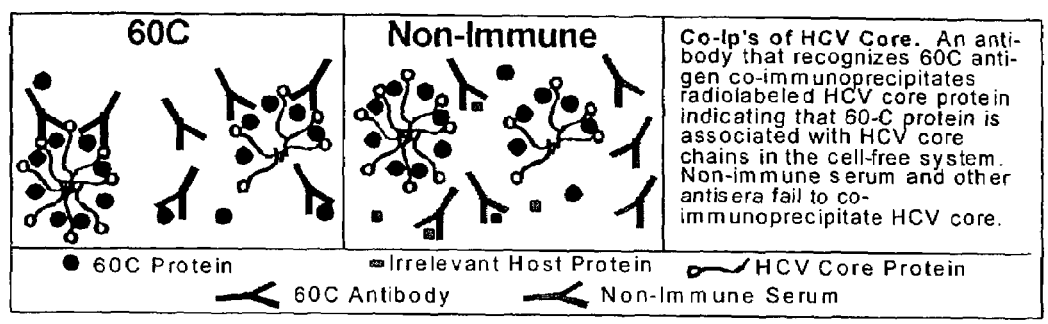
FIG. 19 shows the strategy for co-immunoprecipitation of HCV core.
Figure 20:
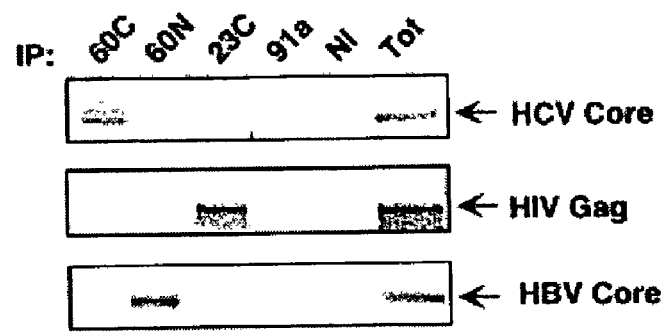
FIG. 20 shows co-immunoprecipitation of HCV core by 60-C anti-serum. Cell-free reactions were programmed with either HCV core, HIV-1 Gag, or HBV Core. During assembly, reactions were subjected to immunoprecipitation (IP) under native conditions with antisera directed against different epitopes of TCP-1 (60-C, 60-N, 23c, and 91a) or with non-immune serum (NI). IP eluates were analyzed by SDS-PAGE and autoradiography. Tot shows a 5% of the input used to program the IP. Arrows show positions of full-length capsid proteins.

To look for an association of HCV core with molecular chaperones, cell-free reactions were programmed with either HCV core, HIV-1 Gag, or HBV Core. During assembly, reactions were subjected to immunoprecipitation (IP) under native conditions with antisera directed against different epitopes of TCP-1 (60-C, 60-N, 23c, and 91a) or with non-immune serum (NI). IP eluates were analyzed by SDS-PAGE and autoradiography. All of the antibodies tested failed to recognize HCV core chains in these assembly reactions except one, suggesting that most molecular chaperones are not associated with assembling full-length chains of HCV core. However, an antiserum (60-C) directed against a specific epitope (aa 400 to 422) of the eukaryotic cytosolic chaperonin TCP-1 co-immunoprecipitated HCV core under native conditions (FIGS. 19 and 20). These data suggest that either TCP-1 or a protein that shares an epitope with TCP-1 is associated with HCV core chains in the cell-free system. The epitope recognized by this antiserum corresponds to the sequence:

N-terminus-RGANDFMCDEMERSLHDA-C-terminus

This epitope is highly conserved among TCP-1 isolated from different species. In addition, this epitope has sequence homology to a region of the bacterial chaperonin GroEL. In general, GroEL shares little overall sequence specificity with TCP-1, but has a very similar structure and function (Frydham, J. et al., (1992) Embo J 11: 4767-78; Gao, Y. et al., (1992) Cell 69: 1043-50; Lewis, V. A., et al., (1992) Nature 358: 249-52; Rommelaere, H. et al., (1993) Proc Natl Acad Sci USA 90: 11975-9; Yaffe, M. B. et al., (1992) Nature 358: 245-8). A BLAST search using the 60-C sequence does not reveal any other proteins having significant sequence homology to the 60-C sequence besides TCP-1 subunits from various species.

Antisera directed against other regions of TCP-1, such as 60-N (Lingappa, J. R., et al., (1994) J Cell Biol 125: 99-111), 23c (Hynes, G. et al., (1996) Electrophoresis 17: 1720-7; Willison, K et al., (1989) Cell 57: 621-32), and 91a (Frydman, J. et al., (1992) Embo J 11: 4767-78), fail to co-immunoprecipitate HCV core. In contrast, HBV core is recognized by the 60-N antiserum (directed against aa 42-57 in TCP-1 (Lingappa, J. R. et al., (1994) J Cell Biol 125: 99-111). Assembling chains of HIV Gag are recognized by the 23c antiserum (which recognizes an epitope containing the last 3 amino acids in TCP-1) (Lingappa, J. R. et al., (1997) J Cell Biol 136: 567-81), as shown in FIG. 20. These differences in epitope recognition are consistent with the possibility that each of these capsid proteins binds to a different host protein. Alternatively, if capsid proteins of two unrelated viruses bind to the same cellular protein (which may be the case for HBV and HCV core), one would expect that each would bind to that protein in a unique way, since capsid proteins of unrelated viruses have no significant sequence homology to each other. Thus, different epitopes are like to be exposed when two unrelated capsid proteins bind to the same cellular protein. Together, the data strongly argue that capsid proteins of different viruses form unique interactions with host proteins during assembly.

Example 18

Figure 21:
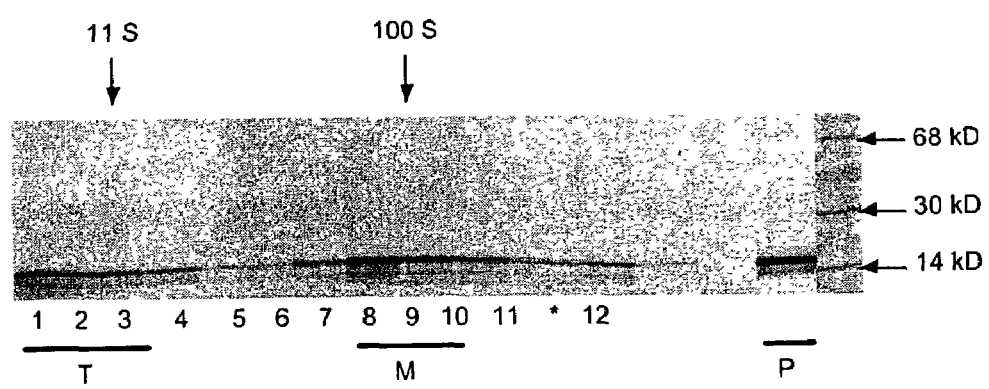
FIG. 21 shows sucrose gradient fractionation of HBV core cell-free translation products. HBV core cDNA was transcribed and translated for 120 min. The translation products were then layered onto a 2.0-ml 10-50% sucrose gradient and centrifuged at 200,000 g for 1 h. 200-microliter fractions were removed sequentially from top to bottom of the gradient (lanes 1-11, respectively) and the pellet (lane 12) was resuspended in 1% NP-40 buffer. Aliquots of each fraction were analyzed by SDS-PAGE and autoradiography to detect the radiolabeled 21-kD core polypeptide band. Two minor HBV core bands of lower molecular weight are seen (in both in vitro translations as well as in core protein produced by transfecting E. coli). These are thought to be either degradative products or the result of initiation of translation at internal methionines. Positions of molecular weight standards are shown. The position of catalase, an 11-S standard, in this type of gradient (as determined by Coomassie staining) is shown with an arrow. Likewise the migration of recombinant core particles, known to have a sedimentation coefficient of ~100S, is shown with an arrow. Radiolabeled HBV core polypeptides migrate in three regions of this gradient: top (T) corresponding to fractions 1 and 2; middle (M) corresponding to fractions 6 and 7; and pellet (P) corresponding to fraction 12, as shown with dark bars.

HBV Core Cell-Free Translation Products Migrate in Three Positions upon Velocity Sedimentation To synthesize radiolabeled HBV core polypeptides, HBV core DNA was transcribed in vitro and translated for 120 min in a heterologous cell-free system containin wheat germ extract (see Example 1). The radiolabeled translation products were analyzed for formation of HBV core multimers by rae sedimentation on 10-50% sucrose gradients at 200,000 g for 1 h. Following fractionation of the gradients, the migration of radiolabeled core proteins was determined using SDS-PAGE, Coomassie staining, and autoradiography. Under these conditions, unlabeled protein standards of less than 12S, such as catalase, migrated in the first three fractions. Mature core particles produced in recominant E. coli (referred to as authentic capsids) were found predominantly in fractions 5-7 (~100S). Radiolabeled cell-free translation products were found to migrate in three distinct positions using these gradient conditions, as shown in FIG. 21. The first region, at the top of the gradient (7) corresponds to the position of monomeric and small oligomeric core polypeptides, while the second region, in the middle of the gradient (M), corresponds to the position of authentic capsids. The third region, in the pellet (P), represents very high molecular weight structures. The possibility that either the pellet or the middle fraction consists of completed chains not yet released from ribosomes was ruled out by treatment of the translation products after completion of synthesis with EDTA, which is known to disassemble ribosomes (Sabatini et al., 1966). Both pellet and middle fractions were largely unaffected by EDTA treatment (data not shown). Taken together, these results raised the possibility that capsid-like particles were being assembled from newly synthesized core polypeptides in this cell-free system.

Figure 27:
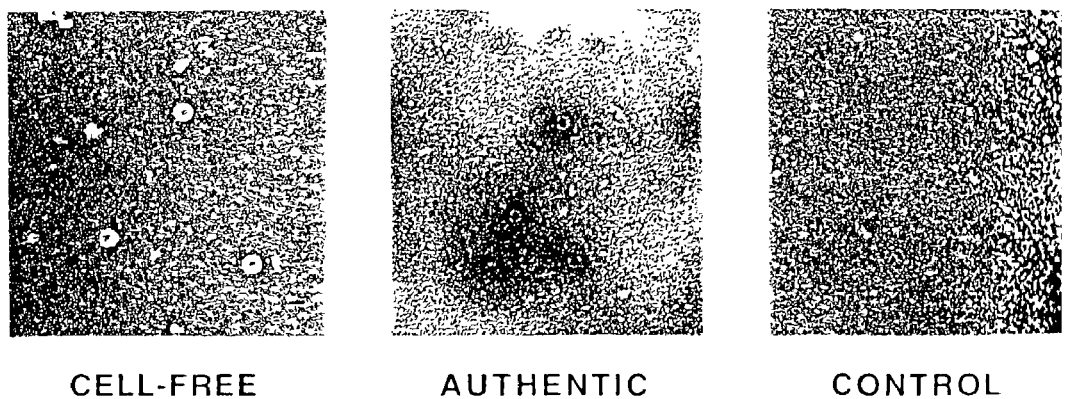
FIG. 27 shows electron micrographs of capsids produced in a cell-free system. Translation of HBV core transcript (CELL-FREE) as well as translation of an unrelated protein (GRP-94 truncated at NcoI, referred to here as CONTROL) were performed for 150 min and these products as well as recombinant capsids (AUTHENTIC) were centrifuged to equilibrium on separate CsCl gradients. Fraction 6 from each gradient was collected and further sedimented in an Airfuge. In single blinded fashion the pellet of each was collected, resuspended, and prepared for EM by negative staining. Identity of samples was correctly determined by the microscopist. No particles resembling capsids were seen in the control samples. Bar, 34 nm.

To confirm the authenticity of the capsids produced in the cell-free system, relevant fractions were examined by EM. The products of cell-free translation of HBV core (FIG. 27, Cell-Free) and of cell-free translation of an unrelated protein (GRP 94) (FIG. 27 Control) as well as recombinant HBV capsids (FIG. 27, authentic) were treated with EDTA to disassemble ribosomes and then centrifuged to equilibrium on CsCl gradients. Fractions 6 and 7 of each of these gradients were collected and concentrated in Airfuge. Electron micrographs of the resuspended pellets examined by a microscopist in single blinded fashion revealed particles indistinguishable from authentic capsids in the products of HBV core cell-free translation. In contrast, no particles resembling capsids were seen in the equivalent fractions of the cell-free translation of an unrelated protein. Thus, by four criteria—velocity sedimentation, buoyant density, protease resistance (data not shown), and electron microscopy—a portion of the HBV core translation products assembles into bona fide HBV capsids.

Figure 22:
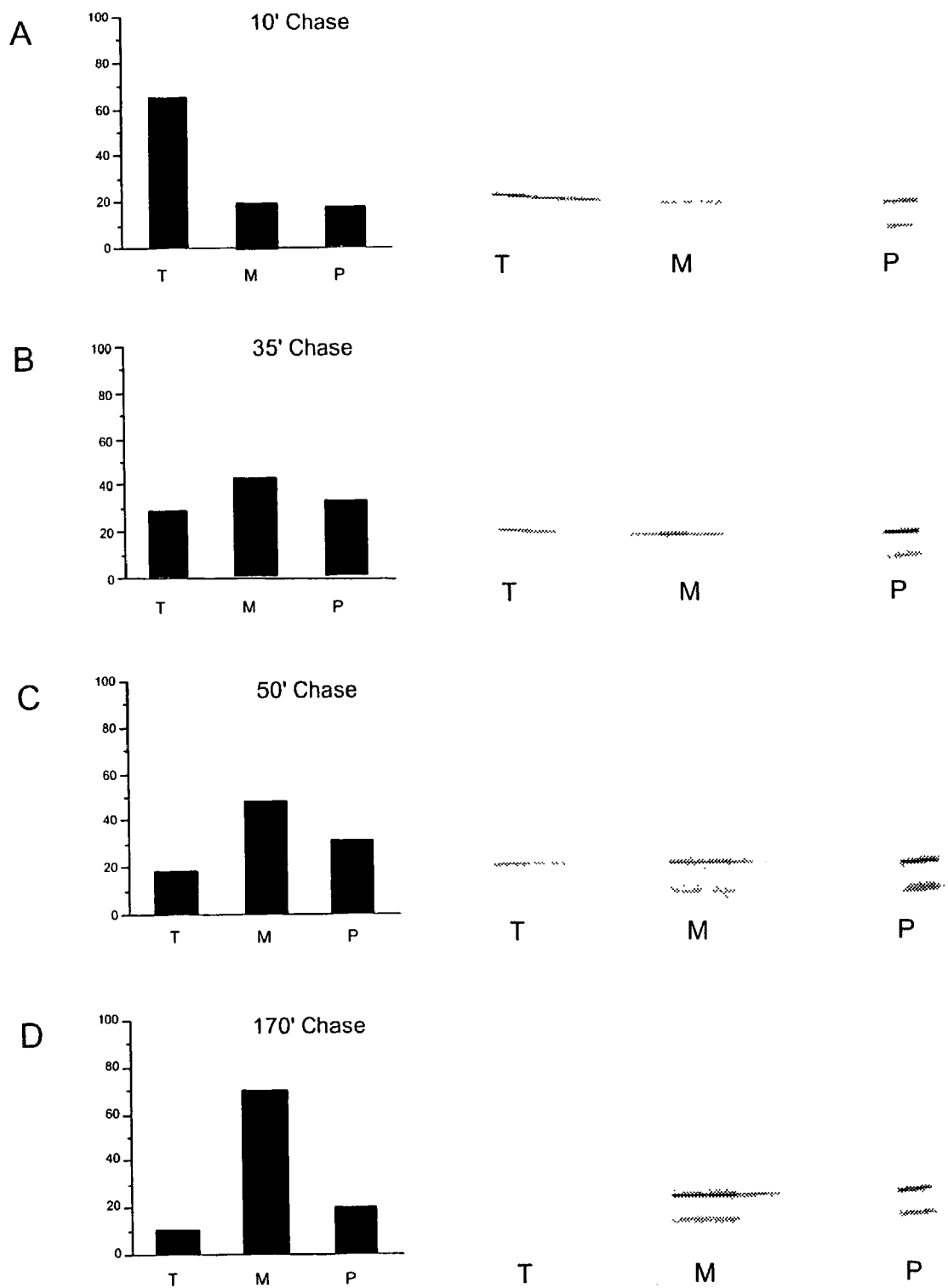
FIG. 22 shows pulse-chase analysis of assembly of HBV core particles. In vitro transcription and translation were performed with an initial 10-min pulse of [35S] cysteine followed by a chase with unlabeled cysteine for either 10 (A), 35 (B), 50 (C), or 170 min (D). Translation products were layered on sucrose gradients, centrifuged, fractionated, and analyzed by SDS-PAGE and autoradiographed as previously described. Autoradiographs are shown to the right of the respective bar graphs that quantitate density of bands present in the top (T), middle (M), and pellet (P) of the respective autoradiographs. The total amount of radiolabeled full-length core polypeptide present at each time point is the same, as determined by quantitation of band densities of 1-microliter aliquots of total translation. Labeled core polypeptides chase from the top to the pellet and finally to the middle of the gradient over time.
Figure 26:
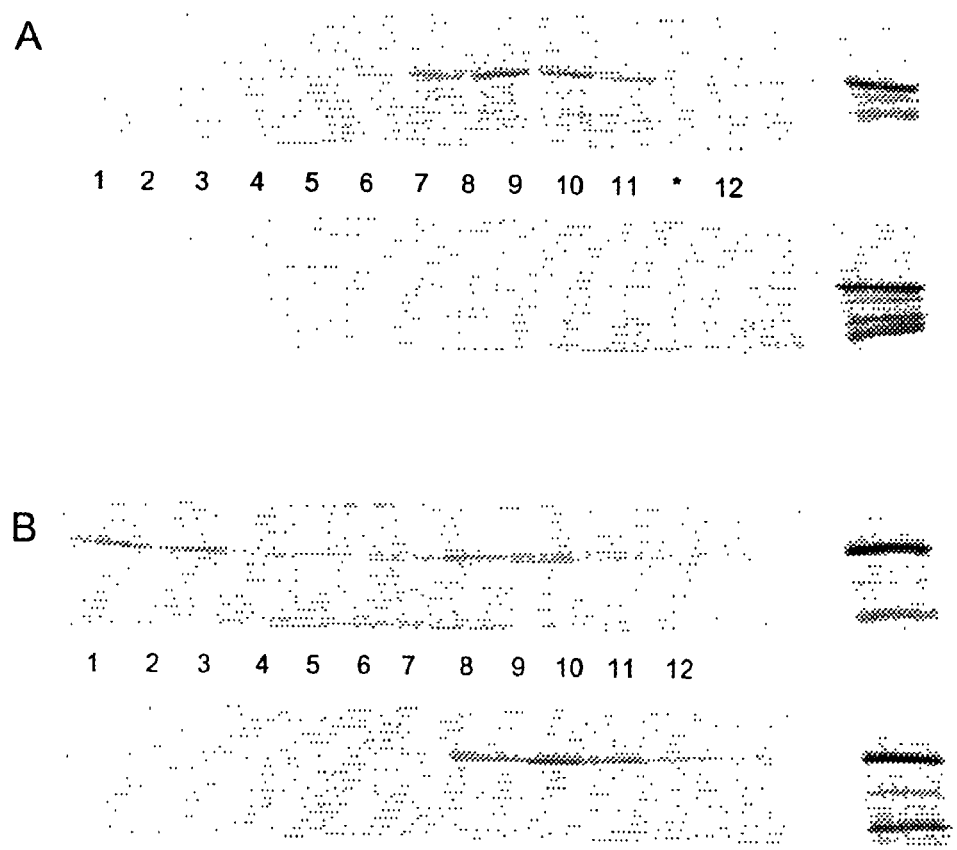
FIG. 26 shows completed capsids are released from the isolated pellet. Following translation of HBV core transcript for 30 min, the translation product was diluted in 0.01% Nikkol buffer and centrifuged on a 10-50% sucrose gradient. The supernatant was removed and the pellet was resuspended in buffer and divided into equal aliquots. To one aliquots was added apyrase (A, top) while the control was incubated in buffer alone (A, bottom). Incubations were done at 25° C. for 90 min. Reaction mixtures were then centrifuged on standard 10-50% sucrose gradients. Fractions were analyzed by SDS-PAGE and autoradiography. In a separate experiment (B) the pellet was isolated and resuspended in identical fashion. To one aliquot was added wheat germ extract as well as unlabeled energy mix. (B, top); to the second aliquot was added wheat germ extract and apyrase (B, bottom). The reactions were incubated at 25° C. for 180 min and centrifuged as described for A. Treatment with apyrase (with or without wheat germ extract) resulted in release of radiolabeled material that migrated in the middle of the gradient. That this material represents complete capsids was confirmed by centrifugation on equilibrium CsCl gradients along with authentic capsid as a control (data not shown). In contrast, treatment with wheat germ extract and energy mix resulted in generation of radiolabeled material that migrated in the top as well as the middle gradient. The material in the middle of these gradients was also shown to include completed capsids by centrifugation on CsCl along with authentic capsids as a marker.

To determine the order of appearance of labeled core polypeptides in top, middle, and pellet fractions of the sucrose gradient described in FIG. 21, cell-free translations were performed using a 10-min pulse of [$^{35}$S]cysteine, followed by a chase for varying lengths of time in the presence of excess unlabeled cysteine. Translation products were sedimented through sucrose gradients and analyzed by SDS-PAGE and autoradiography. After a 10-min chase period, a time at which essentially all of the labeled chains have completed translation, the cohort of chains synthesized in the presence of labeled cystein was found predominantly in the top of the gradient (FIG. 22A). Upon extending the chase period to 35 min, a significant amount of material was found in both the pellet and the middle of the gradient (FIG. 22B). Following a chase period of 50 min, there were very few labeled chains present at the top of the gradient. Rather, increasing amounts of label had accumulated in the pellet and middle fractions (FIG. 22C). After a 170-min chase period, the amount of radiolabeled material in the middle underwent a further increase with a decrease in labeled material in both the pellet and top fractions (FIG. 22D). Quantitation of autoradiographs, shown next to the corresponding gels, confirmed that the labeled material at the top of the gradient diminished dramatically over time. The material in the pellet initially increased and then decreased, while the material in the middle accumulated progressively over the course of the chase period. Thus, the data indicate that newly synthesized core polypeptides chase over time into HBV capsids, and it is likely that they do so, at least in part, by way of a high molecular weight complex contained within the pellet. Definitive confirmation that the pellet contains an intermediate in the formation of completed capsids is presented below (see FIG. 26).

Example 19

CC 60 is Associated with Intermediates in the Assembly of HBV Capsids

A polyclonal rabbit antiserum (anti 60) was raised against a peptide sequence of TCP-1 (FIG. 23A). Studies by others have shown that TCP-1 is a protein of 60 kD that migrates as a so-S particle (Gao et a., 1992; Yaffe et al., 1992). From total extracts of steady state-labeled HeLa cells, our anti 60 antiserum immunoprecipitated a single 60-kD protein under denaturing conditions (FIG. 22B, lane 1). The same 60-kD protein was immunoprecipitated by anti 60 under native conditions (Martin, R., and W. J. Welch, manuscript in preparation). When either rabbit reticulocyte lysate or wheat germ extract was fractionated on a 10-50% sucrose gradient, the ant 60-reactive material migrated as a 20-S particle as revealed by imunoblotting of gradient fractions (FIG. 23C, top and bottom, respectively). Furthermore, a 60-kD polypeptide component of a 20-S particle (purified from reticulocyte lysate) that is known to be recognized by a previously described antibody to TCP-1 (Willison et al., 1989) also reacted to the anti 60 antisera described here (H Sternlicht, personal communication). Mitochondrial hsp 60, in contrast, failed to be recognized by anti 60 (data not shown). The 20-S particle recognized by anti 60 also was recognized by an antibody (provided by J. Trent, Argonne National Laboratory, Argonne, Ill.)(see Trent et al., 1991) against TF 55, the hsp 60 homolog found in the thermophilic archaebacterium *Sulfolobus shibatae* (data not shown). Thus, anti 60 appears to be recognizing either TCP-1 or a closely related eukaryotic cytosolic protein, which we refer to as C 60.

Figure 24:
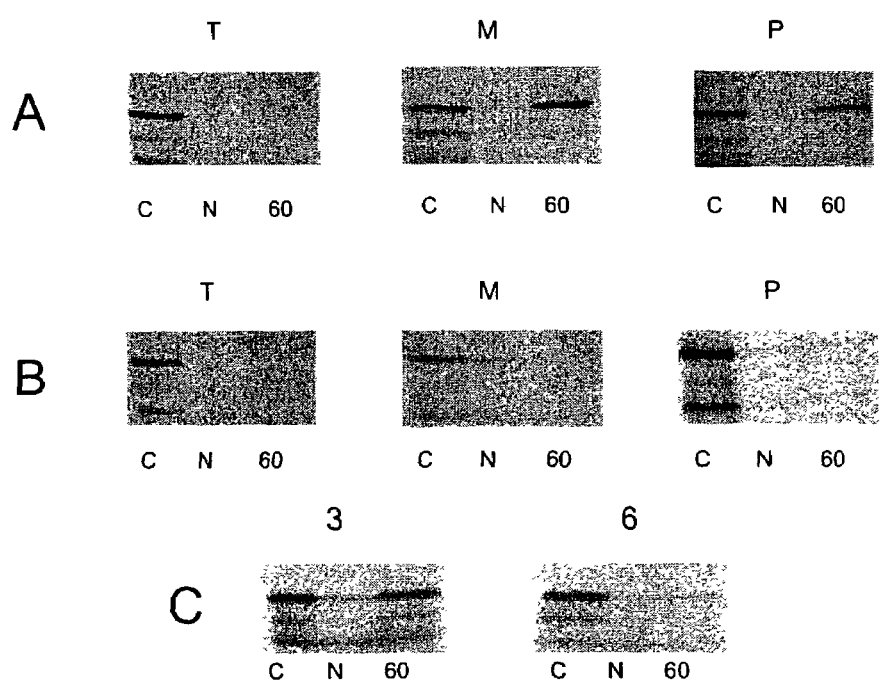
FIG. 24 shows immunoprecipitation of HBV core translation products. HBV core was translated in vitro for 60 min. Translation products were centrifuged on sucrose gradients and fractionated as described in FIG. 21. Fractions from the top ("T"), middle (M) and pellet (P) regions were divided into equal aliquots and immunoprecipitations were performed as described in Materials and Methods under either native (A) or denaturing (B) conditions using either anti-core antiserum (C), nonimmune serum (N), or anti 60 (60). Immunoprecipitated labeled core protein was visualized by SDS-PAGE and autoradiography C shows a separate experiment in which native immunoprecipitations were performed on HBV core translation products following equilibrium density centrifugation. In this experiment, HBV core was translated for 150 min and centrifuged on sucrose gradients as described in FIG. 21. Material from the middle (lanes 6 and 7) of sucrose gradients was pooled and centrifuged on CsCl equilibrium gradients. Fractions 3 and 6 were collected, divided into equal aliquots and immunoprecipitated under native conditions using either anti-core antiserum (C), nonimmune serum (N) or anti 60 (60). Exposure times for autoradiographs were identical for each of the three lanes (C, N, and 60) within a set, but vary between sets.

To determine whether CC 60 is associated with HBV core in the cell-free assembly system, and whether anti 60 (FIG. 24, 60) was able to coprecipitate newly synthesized HBV core polypeptides from various fractions of the sucrose gradients was examined. Control immunoporecipitations were performed using nonimmune serum (FIG. 24, N) as well as polyclonal rabbit antiserum to HBV core polypeptide (FIG. 24C). FIG. 24A shows that under native conditions and 60 coprecipitated radiolabeled core polypeptides present within the middle (M) and the pellet (P) of the sucrose gradients, but did not coprecipitate core polypeptides from the top (T). Similarly, antibody to TF 55 (see above) coprecipitated core polypeptides in the pellet and the middle of the gradients (data not shown). As expected, when immunoprecipitations were performed after denaturation of samples by boiling in SDS, anti 60 no longer coprecipitated core polypeptides from any of these gradient fractions (FIG. 24B). In contrast, antiserum to core polypeptide recognized labeled core protein in all three of these fractions under both native and denaturing conditions (FIGS. 24, A and B). Based on these observations, it appears that CC 60 is not associated with unassembled forms of HBV core protein, but is associated with multimeric forms of the protein. These results raised the possibility that CC 60 plays a role in the assembly of HBV core particles.

If CC 60 were to play a role in assembly, one might expect this chaperonin to dissociate from the multimeric core particle once assembly is complete. To test this hypothesis we performed immunoprecipitations on material from the middle of sucrose gradients that had been further fractionated on a CsCl gradient. Using such an equilibrium centrifugation method we can separate mature capsids (found in fractions 1-4 of the CSCl gradients) and are possibly incomplete assembly intermediates. FIG. 24C shows that under native conditions, anti 60 precipitates HBV core polypeptides present in fraction 3 from CsCl gradients (corresponding to incomplete capsids) but fails to precipitate core polypeptides present in fraction 6 from the same gradients (corresponding to completed capsids). Antiserum to core polypeptide recognizes core protein in both fractions. Thus it appears that CC 60 is associated with partially assembled capsids, but is not associated with mature capsids.

As further confirmation that CC is only transiently associated with core polypeptides in the process of assembly, immunoblots of gradient fractions were performed with antiserum to CC 60 at different times during translation (Lingappa, J. R., W. J. Welch, and V. R. Lingappa, manuscript in preparation). These immunoblots revealed the presence of a large amount of CC 60 in the pellet at early time points during ranslation of HBV core transcript but not during translation of mock transcript. In contrast, at later times during the core translation and assembly reaction, all of the CC 60 was located in the 20-S position with none remaining in the pellet. In these experiments the total amount of CC 60 was essentially unchanged over the course of translation.

Example 20

HBV Core Polypeptide Production can be Uncoupled from Core Particle Assembly

Figure 25:
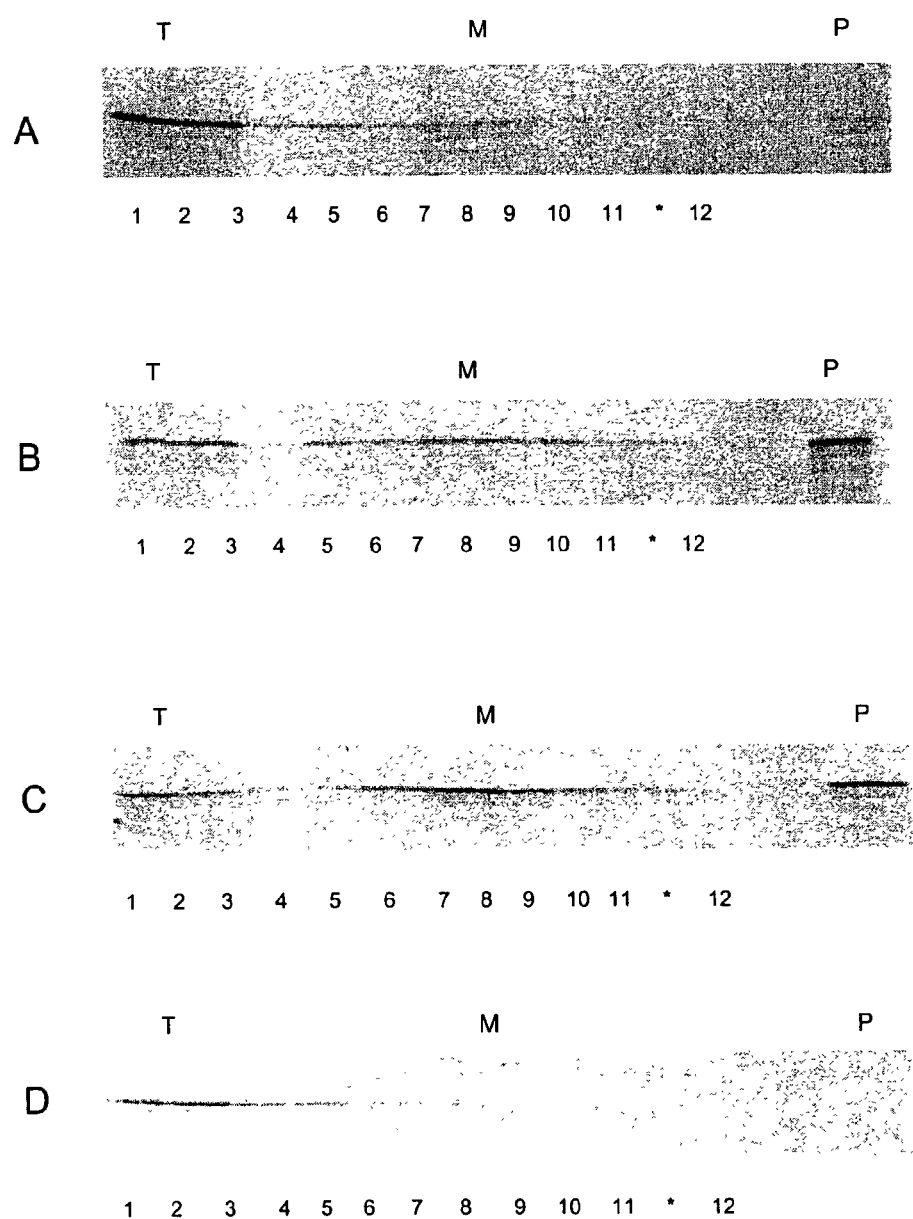
FIG. 25 shows that unassembled core polypeptides can be chased into multimeric particles. HBV core transcript was diluted by 50% with mock transcript, and then translated for 120 min. Translation products were divided into three aliquots. One aliquot was put on ice (A). To a second aliquot was added a translation of HBV core polypeptides that was made using 100% transcript and only unlabeled amino acids that had been incubated for 45 min. This mixture was then further incubated for either 45 (B) or 120 min (C). To a third aliquots was added a translation of mock transcript that had been incubated for 45 min, and this mixture was further incubated for 120-min (D). All four samples were then centrifuged on sucrose gradients and fractions were removed and analyzed by SDS-PAGE and autoradiography as previously described. Unassembled core polypeptides shown in A are found to move first into the pellet and then into the middle over time (B and C, respectively) with the addition of high concentration of (unlabeled) HBV core polypeptide chains. In contrast, with addition of mock translation (D), core polypeptides remain at the top of the gradient.

To distinguish between a role for CC 60 in folding of core monomers versus a role in assembly of multimeters, we attempted to uncouple production of core polypeptides from core particle assembly. In *Xenopus* oocytes, assembly of core particles is known to be exquisitely dependent on the concentration of core polypeptide chains (Seifer et al., 1993). We observed an equally striking concentration dependence in our system. When we decreased the concentration of HBV core transcript to 50% or less of the standard concentration used in our cell-free system, HBV capsid assembly was virtually abolished (FIG. 25A), while total core polypeptide synthesis was diminished in a roughly linear fashion (data not shown). These conditions resulted in the accumulation of a population of unassembled, full-length core polypeptides that migrated at the top of the previously described sucrose gradients (FIG. 25A). Even when incubated for a long time (6 h), these unassembled chains remained at the top of the gradient indicating that assembly does not occur even at a slow rate under these conditions (data not shown). When centrifuged on a 5-25% glycerol gradient for 14 h, the unassembled core polypeptides migrated in the approximate region expected for folded globular dimers of core, based on the position of protein standards (data not shown). Thus, the data indicate that the unassembled material at the top of the gradient does not consist of unfolfed polypeptides. Rather, this material likely represents core polypeptide dimers, or a mixture of monomers and dimers. Dimers are known to be capsid assembly precursors in vivo (Zhou and Standring, 1992).

To determine whether the unassembled core polypeptides present at the top of the gradient are in fact competent for assembly into capsids, we asked if they could be chased into capsids in the presence of excess unlabeled core chains. To do this we added to these unassembled radiolabeled chains an excess of an unlabeled translation mix that had been programmed with 100% core transcript for 45 min. The 45-min time point was chosen because it represents a point at which the newly synthesized core chains are present in roughly equal proportions in the top, middle, and pellet regions of our standard sucrose gradients (data not shown). After mixing the labeled, unassembled chains with the unlabeled translation, incubation was continued at 24° C. for either 45 or 120 min and the mixture was then layered onto sucrose gradients, centrifuged, fractionated, and analyzed by SDS-PAGE and autoradiography as previously described. After a 45-min incubation, the labeled polypeptides were found primarily in the pellet (P) with a small amount in the middle of the gradient (M) (FIG. 25B), while after 120 mins a significant quantity of labeled chains was present in the middle of the gradient (FIG. 25C). When material from the middle of that sucrose gradient (FIG. 25C) was subsequently centrifuged on CsCl, the radiolabeled chains were found to comigrate with authentic core particles confirming that completed capsids were produced during the chase (data not shown).

When an unlabeled mock translation was preincubated for 45 min and added to the unassembled core polypeptides, the radiolabeled core polypeptides at the top of the gradient failed to chase into either the pellet or the middle (FIG. 25D). A similar result was obtained when a translation programmed with bovine prolactin, an unrelated protein, was added to the unassembled core polypeptides. Likewise, when an unlabeled translation of 50% of the standard core transcript was added to the unassembled radiolabeled core polypeptides, the radiolabeled chains remained at the top of the gradient (data not shown). In the latter experiment the concentration of HBV core chains was maintained at 50% of the standard conentration, and thus failed to rise to the necessary threshold for assembly. Thus, under the appropriate conditions, unassembled chains appear to be competent to form mature capsids.

Example 21

Completed Capsids can be Released by Manipulation of the Isolated Pellet

Having found an association of CC 60 with multimeric complexes, we wished to determine whether any of these complexes constitute intermediates in the assembly of the final capsid product and whether energy substrates play a role in the progression of such intermediates. Molecular chaperones are known to be involved in solubilizing aggregates of misfolded protein as well as in facilitating correct folding and assembly of polypeptides as discussed above. Thus, CC 60 could be associated with multimeric complexes in the pellet and middle fractions either because these complexes represent "dead end pathways" consisting of aggregates of misfolded or misassembled protein, or because these complexes represent productive intermediates along the pathway towards assembly of completed capsids. To address this, pellet material was isolated by fractionating the products of a 30-min translation of HBV core on a sucrose gradient and resuspending the pellet in buffer. The resuspended pellet was divided into equal aliquots and treated either with aphyase or with buffer for 90 min at 24° C. Radiolabeled material from the pellet chased to the middle with aphyrase treatment (FIG. 26A, top), but not with incubation in buffer (FIG. 26A, bottom). When fractions 6 and 7 were collected after apyrase treatment and centrifuged to equilibrium on a CsCl gradient, most of the radiolabeled material was found to comigrate with authentic core particles (data not shown). Thus, apyrase treatment of isolated pellet material results in release of completed capsids from the pellet.

When the isolated pellet was treated with the energy mix used in cell-free translations (containing ATP, GTP, and creatine phosphate) along with the wheat germ extract, radiolabeled core polypeptides in the pellet were found to chase into both middle and top fractions (FIG. 26B, top). Once again, when the radiolabeled material in the middle was examined by equilibrium sedimentation, a small portion had a buoyant density identical to that of authentic capsids (data not shown). Treatment of the isolated pellet with either wheat germ extract or energy mix alone resulted in chase of a much smaller amount of radiolabeled material to the middle of the gradient (data not shown). Treatment of the isolated pellet with apyrase and wheat germ extract (FIG. 26B, bottom) produced the same result as treatment with apyrase along (FIG. 26A, top). Thus, the addition of energy substrates results in release of both unassembled core polypeptides as well as assembled capsids from the pellet. Additional data demonstrated that the polysomes do not play a role in the pellet: (a) the protein synthesis inhibitor emetine did not affect the results of treatment of the isolated pellet with energy substrates or apyrase; ad (b) as previously mentioned, treatment of translation products with 10 mM EDTA had no effect on relative distribution of labeled core polypeptides in the top, middle, and pellet regions of the gradients (data not shown). The ability of the pellet to chase into completed capsids with various manipulations of energy substrates indicates that some of the material in the pellet constitutes an intermediate in the pathway to completed capsids.

One universal step in the lifecycle of all viruses is formation of the capsid. As the above results show, for multiple viruses from different families, capsid assembly is not spontaneous but rather is catalysed by the action of host proteins and occurs via assembly intermediates. An obligate, stereotyped, pathway of capsid assembly, distinct in both host factors and assembly intermediates for each different class of viruses studied to date, occurs. The cell-free translation system in which these discoveries were made can be used as a means of diagnosing a virus based on the host protein that forms the assembly intermediates and for screening for compounds that inhibit the process of capsid assembly. Furthermore in that system the assembly intermediates can be detected and enriched. Both the host proteins and the assembly intermediates are promising candidate anti-viral targets, as evidence demonstrates in one case that expression of a dominant negative mutant of one such host protein terminates release of virus from infected cells. Thus, anti-capsid therapy, in the form of small molecule drugs that interfere with those host proteins or the flux of intermediates involved in capsid assembly, are a promising new line of targets for antiviral drugs and can be used even for viruses for which a culture system has not been established. This step of capsid assembly has not previously been the target of antiviral therapy because it had been believed that the capsid was formed spontaneously by "self-assembly" and therefore lacked a specific protein target.

All references cited herein are incorporated herein by reference, as if set forth in their entirety.

Although the foregoing invention has been described in some detail by way of illustration and example for purposes of clarity of understanding, it will be obvious that certain changes and modifications may be practiced within the scope of the appended claims.

What is claimed is:

1. A method for identifying a compound that interferes with capsid assembly of a virus, said method comprising:

expressing at least one conformer of a protein required for said capsid assembly in the presence of a test compound, wherein said expressing is in a cell free translation system programmed with nucleic acid encoding said at least one conformer of such protein, and wherein said cell free translation system produces fully completed capsids in the absence of said test compound; and determining whether there has been a decrease in production of said capsids in the presence of said compound relative to the production of said capsids in the absence of said compound.

2. The method according to claim 1, wherein the virus is HIV.

3. The method according to claim 1, wherein said virus is HCV.

4. The method according to claim 1, wherein said virus is HBV.

5. The method according to claim 1, wherein said test compound is a peptide.

6. The method according to claim 1, wherein said test compound is an antibody.

7. The method according to claim 1, wherein said test compound is an anti-capsid antibody.

8. The method according to claim 1, wherein said test compound is a small molecule.

* * * * *

UNITED STATES PATENT AND TRADEMARK OFFICE
CERTIFICATE OF CORRECTION

PATENT NO. : 7,638,269 B2 Page 1 of 1
APPLICATION NO. : 10/243509
DATED : December 29, 2009
INVENTOR(S) : Lingappa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this

Ninth Day of November, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 1610
<212> TYPE: DNA
<213> ORGANISM: HIV
<220> FEATURE:
<223> OTHER INFORMATION: DNA coding sequence for HIV capsid protein Pr55

<400> SEQUENCE: 1

```
atgggtgcga gagcgtcggt attaagcggg ggagaattag ataaatggga aaaaattcgg      60
ttaaggccag ggggaaagaa aaaatataag ttaaaacata tagtatgggc aagcagggag     120
ctagaacgat tcgcagtcaa tcctggcctg ttagaaacat cagaaggctg cagacaaata     180
ttgggacagc tacagccatc ccttcagaca ggatcagaag aacttagatc attatataat     240
acagtagcaa ccctctattg tgtacatcaa aggatagatg taaaagacac caaggaagct     300
ttagagaaga tagaggaaga gcaaaacaaa agtaagaaaa aggcacagca agcagcagct     360
gcagctggca caggaaacag cagccaggtc agccaaaatt accctatagt gcagaaccta     420 cagggcaaa tggtacatca ggccatatca cctagaactt taaatgcatg ggtaaaagta     480
gtagaagaaa aggctttcag cccagaagta atacccatgt tttcagcatt atcagaagga     540 gccacccac aagatttaaa caccatgcta aacacagtgg ggggacatca agcagccatg     600
caaatgttaa aagagactat caatgaggaa gctgcagaat gggatagagt gcatccagtg     660
catgcagggc ctattgcacc aggccaaatg agagaaccaa ggggaagtga catagcagga     720
actactagta cccttcagga acaaatagga tggatgacaa ataatccacc tatcccagta     780
ggagaaatct ataaaagatg gataatcctg ggattaaata aaatagtaag aatgtatagc     840
cctaccagca ttctggacat aagacaagga ccaaaggaac cctttagaga ttatgtagac     900
cggttctata aaactctaag agccgaacaa gcttcacagg atgtaaaaaa ttggatgaca     960
gaaaccttgt tggtccaaaa tgcaaaccca gattgtaaga ctattttaaa agcattggga    1020
ccagcagcta cactagaaga aatgatgaca gcatgtcagg gagtgggggg acccggccat    1080
aaagcaagag ttttggctga agccatgagc caagtaacaa atccagctaa cataatgatg    1140
cagagaggca attttaggaa ccaaagaaag actgttaagt gtttcaattg tggcaaagaa    1200
gggcacatag ccaaaaattg cagggcccct aggaaaaagg gctgttggag atgtggaagg    1260
gaaggacacc aaatgaaaga ttgcactgag agacaggcta atttttagg gaagatctgg    1320 ccttcctaca agggaaggcc agggaatttt cttcagagca gaccagagcc aacagcccca    1380
ccagaagaga gcttcaggtt tggggaggag aaaacaactc cctctcagaa gcaggagccg    1440
atagacaagg aactgtatcc tttaacttcc ctcagatcac tctttggcaa cgacccctcg    1500
tcacaataag gataggggg caactaaagg aagctctatt agatacagga gcagatgata    1560
cagtattaga agaaatgaat ttgccaggaa aatggaaacc aaaaatgata              1610
```

<210> SEQ ID NO 2
<211> LENGTH: 24
<212> TYPE: PRT

-continued

```
<213> ORGANISM: Triticum aestivum
<220> FEATURE:
<223> OTHER INFORMATION: peptide fragment of host cell (wheat germ)
      protein HP68

<400> SEQUENCE: 2

Pro Arg Pro Tyr Leu Asp Val Lys Gln Arg Leu Lys Ala Ala Arg Val
  1               5                  10                  15

Ile Arg Ser Leu Leu Arg Ser Asn
             20

<210> SEQ ID NO 3
<211> LENGTH: 44
<212> TYPE: DNA
<213> ORGANISM: Artificial Sequence
<220> FEATURE:
<223> OTHER INFORMATION: Degenerate oligonucleotide C-terminal peptide
sequence of WGHP68

<400> SEQUENCE: 3
atgaattcac tgggactgcg gatagattac tggtactggg gatc                      44

<210> SEQ ID NO 4
<211> LENGTH: 42
<212> TYPE: DNA
<213> ORGANISM: Artificial Sequence
<220> FEATURE:
<223> OTHER INFORMATION: Degenerate oligonucleotide C-terminal peptide
      sequence of WGHP68

<400> SEQUENCE: 4
atgaattcac tgggctctga tagattactg gtactgggga tc                        42

<210> SEQ ID NO 5
<211> LENGTH: 604
<212> TYPE: PRT
<213> ORGANISM: Triticum aestivum

<400> SEQUENCE: 5

Met Ala Asp Arg Leu Thr Arg Ile Ala Ile Val Ser Glu Asp Lys Cys
  1               5                  10                  15

Lys Pro Lys Lys Cys Arg Gln Glu Cys Lys Lys Ser Cys Pro Val Val
             20                  25                  30

Lys Thr Gly Lys Leu Cys Ile Glu Val Ser Pro Val Ala Lys Leu Ala
         35                  40                  45

Phe Ile Ser Glu Glu Leu Cys Ile Gly Cys Gly Ile Cys Val Lys Lys
     50                  55                  60

Cys Pro Phe Asp Ala Ile Glu Ile Ile Asn Leu Pro Lys Asp Leu Glu
 65                  70                  75                  80

Lys Asp Thr Thr His Arg Tyr Gly Pro Asn Thr Phe Lys Leu His Arg
                 85                  90                  95

Leu Pro Val Pro Arg Pro Gly Gln Val Leu Gly Leu Val Gly Thr Asn
            100                 105                 110

Gly Ile Gly Lys Ser Thr Ala Leu Lys Val Leu Ala Gly Lys Leu Lys
        115                 120                 125

Pro Asn Leu Gly Arg Phe Lys Asn Pro Pro Asp Trp Gln Glu Ile Leu
    130                 135                 140

Thr Tyr Phe Arg Gly Ser Glu Leu Gln Asn Tyr Phe Thr Arg Ile Leu
145                 150                 155                 160

Glu Asp Asn Leu Lys Ala Ile Ile Lys Pro Gln Tyr Val Asp His Ile
                165                 170                 175
```

-continued

```
Pro Lys Ala Val Gln Gly Asn Val Gly Gln Val Leu Glu Gln Lys Asp
            180                 185                 190

Glu Arg Asp Met Lys Asn Glu Leu Cys Val Asp Leu Glu Leu Asn Gln
        195                 200                 205

Val Ile Asp Arg Asn Val Gly Asp Leu Ser Gly Gly Glu Leu Gln Arg
    210                 215                 220

Phe Ala Ile Ala Val Val Ala Val Gln Ser Ala Glu Ile Tyr Met Phe
225                 230                 235                 240

Asp Glu Pro Ser Ser Tyr Leu Asp Val Lys Gln Arg Leu Lys Ala Ala
                245                 250                 255

Arg Val Ile Arg Ser Leu Leu Arg Ser Asn Ser Tyr Val Ile Val Val
            260                 265                 270

Glu His Asp Leu Ser Val Leu Asp Tyr Leu Ser Asp Phe Ile Cys Cys
        275                 280                 285

Leu Tyr Gly Lys Pro Gly Ala Tyr Gly Val Val Thr Leu Pro Phe Ser
    290                 295                 300

Val Arg Glu Gly Ile Asn Ile Phe Leu Ala Gly Phe Val Pro Thr Glu
305                 310                 315                 320

Asn Leu Arg Phe Arg Asp Glu Ser Leu Thr Phe Lys Ile Ala Glu Thr
                325                 330                 335

Gln Glu Ser Ala Glu Glu Val Ala Thr Tyr Gln Arg Tyr Lys Tyr Pro
            340                 345                 350

Thr Met Ser Lys Thr Gln Gly Asn Phe Lys Leu Ser Val Val Glu Gly
        355                 360                 365

Glu Phe Thr Asp Ser Gln Ile Val Val Met Leu Gly Glu Asn Gly Thr
    370                 375                 380

Gly Lys Thr Thr Phe Ile Arg Met Leu Ala Gly Leu Leu Lys Pro Asp
385                 390                 395                 400

Thr Met Glu Gly Thr Glu Val Glu Ile Pro Glu Phe Asn Val Ser Tyr
                405                 410                 415

Lys Pro Gln Lys Ile Ser Pro Lys Phe Gln His Pro Val Arg His Leu
            420                 425                 430

Leu His Ser Lys Ile Arg Asp Ser Tyr Thr His Pro Gln Phe Val Ser
        435                 440                 445

Asp Val Met Lys Pro Leu Gln Ile Glu Gln Leu Met Asp Gln Glu Val
    450                 455                 460

Ile Asn Leu Ser Gly Gly Glu Leu Gln Arg Val Ala Leu Cys Leu Cys
465                 470                 475                 480

Leu Gly Lys Pro Ala Asp Ile Tyr Leu Ile Asp Glu Pro Ser Ala Tyr
                485                 490                 495

Leu Asp Ser Glu Gln Arg Ile Val Ala Ser Lys Val Ile Lys Arg Phe
            500                 505                 510

Ile Leu His Ala Lys Lys Thr Ala Phe Ile Val Glu His Asp Phe Ile
        515                 520                 525

Met Ala Thr Tyr Leu Ala Asp Lys Val Ile Val Tyr Glu Gly Leu Ala
    530                 535                 540

Ser Ile Asp Cys Thr Ala Asn Ala Pro Gln Ser Leu Val Ser Gly Met
545                 550                 555                 560

Asn Lys Phe Leu Ser His Leu Asp Ile Thr Phe Arg Arg Asp Pro Thr
                565                 570                 575

Asn Tyr Arg Pro Arg Ile Asn Lys Leu Glu Ser Thr Lys Asp Arg Glu
            580                 585                 590
```

-continued

Gln Lys Asn Ala Gly Ser Tyr Tyr Tyr Leu Asp Asp
        595                 600

<210> SEQ ID NO 6
<211> LENGTH: 599
<212> TYPE: PRT
<213> ORGANISM: Homo sapiens

<400> SEQUENCE: 6

Met Ala Asp Lys Leu Thr Arg Ile Ala Ile Val Asn His Asp Lys Cys
1               5                   10                  15

Lys Pro Lys Lys Cys Arg Gln Glu Cys Lys Lys Ser Cys Pro Val Val
            20                  25                  30

Arg Met Gly Lys Leu Cys Ile Glu Val Thr Pro Gln Ser Lys Ile Ala
        35                  40                  45

Trp Ile Ser Glu Thr Leu Cys Ile Gly Cys Gly Ile Cys Ile Lys Lys
    50                  55                  60

Cys Pro Phe Gly Ala Leu Ser Ile Val Asn Leu Pro Ser Asn Leu Glu
65                  70                  75                  80

Lys Glu Thr Thr His Arg Tyr Cys Ala Asn Ala Phe Lys Leu His Arg
                85                  90                  95

Leu Pro Ile Pro Arg Pro Gly Glu Val Leu Gly Leu Val Gly Thr Asn
            100                 105                 110

Gly Ile Gly Lys Ser Ala Ala Leu Lys Ile Leu Ala Gly Lys Gln Lys
        115                 120                 125

Pro Asn Leu Gly Lys Tyr Asp Asp Pro Pro Asp Trp Gln Glu Ile Leu
    130                 135                 140

Thr Tyr Phe Arg Gly Ser Glu Leu Gln Asn Tyr Phe Thr Lys Ile Leu
145                 150                 155                 160

Glu Asp Asp Leu Lys Ala Ile Ile Lys Pro Gln Tyr Val Ala Arg Phe
                165                 170                 175

Leu Arg Leu Ala Lys Gly Thr Val Gly Ser Ile Leu Asp Arg Lys Asp
            180                 185                 190

Glu Thr Lys Thr Gln Ala Ile Val Cys Gln Gln Leu Asp Leu Thr His
        195                 200                 205

Leu Lys Glu Arg Asn Val Glu Asp Leu Ser Gly Gly Glu Leu Gln Arg
    210                 215                 220

Phe Ala Cys Ala Val Val Cys Ile Gln Lys Ala Asp Ile Phe Met Phe
225                 230                 235                 240

Asp Glu Pro Ser Ser Tyr Leu Asp Val Lys Gln Arg Leu Lys Ala Ala
                245                 250                 255

Ile Thr Ile Arg Ser Leu Ile Asn Pro Asp Arg Tyr Ile Ile Val Val
            260                 265                 270

Glu His Asp Leu Ser Val Leu Asp Tyr Leu Ser Asp Phe Ile Cys Cys
        275                 280                 285

Leu Tyr Gly Val Pro Ser Ala Tyr Gly Val Val Thr Met Pro Phe Ser
    290                 295                 300

Val Arg Glu Gly Ile Asn Ile Phe Leu Asp Gly Tyr Val Pro Thr Glu
305                 310                 315                 320

Asn Leu Arg Phe Arg Asp Ala Ser Leu Val Phe Lys Val Ala Glu Thr
                325                 330                 335

Ala Asn Glu Glu Glu Val Lys Lys Met Cys Met Tyr Lys Tyr Pro Gly
            340                 345                 350

Met Lys Lys Lys Met Gly Glu Phe Glu Leu Ala Ile Val Ala Gly Glu
        355                 360                 365

-continued

```
Phe Thr Asp Ser Glu Ile Met Val Met Leu Gly Glu Asn Gly Thr Gly
        370                 375                 380

Lys Thr Thr Phe Ile Arg Met Leu Ala Gly Arg Leu Lys Pro Asp Glu
385                 390                 395                 400

Gly Gly Glu Val Pro Val Leu Asn Val Ser Tyr Lys Pro Gln Lys Ile
                405                 410                 415

Ser Pro Lys Ser Thr Gly Ser Val Arg Gln Leu Leu His Glu Lys Ile
                420                 425                 430

Arg Asp Ala Tyr Thr His Pro Gln Phe Val Thr Asp Val Met Lys Pro
            435                 440                 445

Leu Gln Ile Glu Asn Ile Ile Asp Gln Glu Val Gln Thr Leu Ser Gly
    450                 455                 460

Gly Glu Leu Gln Arg Val Arg Leu Arg Leu Cys Leu Gly Lys Pro Ala
465                 470                 475                 480

Asp Val Tyr Leu Ile Asp Glu Pro Ser Ala Tyr Leu Asp Ser Glu Gln
                485                 490                 495

Arg Leu Met Ala Ala Arg Val Val Lys Arg Phe Ile Leu His Ala Lys
            500                 505                 510

Lys Thr Ala Phe Val Val Glu His Asp Phe Ile Met Ala Thr Tyr Leu
        515                 520                 525

Ala Asp Arg Val Ile Val Phe Asp Gly Val Pro Ser Lys Asn Thr Val
    530                 535                 540

Ala Asn Ser Pro Gln Thr Leu Leu Ala Gly Met Asn Lys Phe Leu Ser
545                 550                 555                 560

Gln Leu Glu Ile Thr Phe Arg Arg Asp Pro Asn Asn Tyr Arg Pro Arg
                565                 570                 575

Ile Asn Lys Leu Asn Ser Ile Lys Asp Val Glu Gln Lys Lys Ser Gly
            580                 585                 590

Asn Tyr Phe Phe Leu Asp Asp
        595
```